United States Patent
Stoessel et al.

(10) Patent No.: US 9,741,942 B2
(45) Date of Patent: Aug. 22, 2017

(54) MATERIALS FOR ORGANIC ELECTROLUMINESCENT DEVICES

(71) Applicant: Merck Patent GmbH, Darmstadt (DE)

(72) Inventors: Philipp Stoessel, Frankfurt am Main (DE); Amir Hossain Parham, Frankfurt am Main (DE); Christof Pflumm, Darmstadt-Arheilgen (DE); Anja Jatsch, Frankfurt am Main (DE); Thomas Eberle, Landau (DE); Jonas Valentin Kroeber, Frankfurt am Main (DE)

(73) Assignee: Merck Patent GmbH, Darmstadt (DE)

(*) Notice: Subject to any disclaimer, the term of this patent is extended or adjusted under 35 U.S.C. 154(b) by 305 days.

(21) Appl. No.: 14/434,460

(22) PCT Filed: Sep. 13, 2013

(86) PCT No.: PCT/EP2013/002748
§ 371 (c)(1),
(2) Date: Apr. 9, 2015

(87) PCT Pub. No.: WO2014/056567
PCT Pub. Date: Apr. 17, 2014

(65) Prior Publication Data
US 2015/0270495 A1    Sep. 24, 2015

(30) Foreign Application Priority Data
Oct. 11, 2012  (EP) ..................... 12007040

(51) Int. Cl.
| | | |
|---|---|---|
| *C07D 455/03* | (2006.01) |
| *H01L 51/00* | (2006.01) |
| *C09K 11/06* | (2006.01) |
| *C07D 471/16* | (2006.01) |
| *C07D 471/22* | (2006.01) |
| *C07D 491/048* | (2006.01) |
| *C07D 495/22* | (2006.01) |
| *C07D 498/14* | (2006.01) |
| *C07D 513/14* | (2006.01) |
| *C09K 11/02* | (2006.01) |
| *H01L 51/50* | (2006.01) |
| *H01L 51/52* | (2006.01) |

(52) U.S. Cl.
CPC ........ *H01L 51/0072* (2013.01); *C07D 455/03* (2013.01); *C07D 471/16* (2013.01); *C07D 471/22* (2013.01); *C07D 491/048* (2013.01); *C07D 495/22* (2013.01); *C07D 498/14* (2013.01); *C07D 513/14* (2013.01); *C09K 11/02* (2013.01); *C09K 11/06* (2013.01); *H01L 51/006* (2013.01); *H01L 51/0052* (2013.01); *H01L 51/0054* (2013.01); *H01L 51/0056* (2013.01); *H01L 51/0061* (2013.01); *H01L 51/0067* (2013.01); *H01L 51/0071* (2013.01); *H01L 51/0073* (2013.01); *H01L 51/0074* (2013.01); *C09K 2211/1011* (2013.01); *C09K 2211/1029* (2013.01); *C09K 2211/1033* (2013.01); *C09K 2211/1037* (2013.01); *C09K 2211/1059* (2013.01); *C09K 2211/1088* (2013.01); *C09K 2211/1092* (2013.01); *H01L 51/0058* (2013.01); *H01L 51/5008* (2013.01); *H01L 51/5012* (2013.01); *H01L 51/5056* (2013.01); *H01L 51/5072* (2013.01); *H01L 51/5092* (2013.01); *H01L 51/5096* (2013.01); *H01L 51/5221* (2013.01); *H01L 2251/301* (2013.01); *H01L 2251/308* (2013.01)

(58) Field of Classification Search
None
See application file for complete search history.

(56) References Cited

U.S. PATENT DOCUMENTS 6,187,786 B1 * 2/2001 Venet .................. C07D 471/06
                                                                  514/224.5
8,501,948 B2    8/2013 Konemann

FOREIGN PATENT DOCUMENTS

| DE | 102005037115 A1 | 2/2007 |
| EP | 0014567 A1 | 8/1980 |
| EP | 0074777 A1 | 3/1983 |

OTHER PUBLICATIONS

Zhang et al. "Free radical reactions for heterocycle synthesis. Part 6: 2-Bromobenzoic acids as building blocks in the construction of nitrogen heterocycles" Tetrahedron, 2003, 59, 3009-3018.*
Hamana et al. "Studies on Tertiary Amine Oxides. XLVII. Reaction of Quinoline 1-Oxide Derivatives with Cyanogen Bromide" Chem. Pharm. Bill. 1974, 22(7), 1506-1518.*
International Search Report for PCT/EP2013/002748 mailed Mar. 11, 2014.

* cited by examiner

*Primary Examiner* — Robert S Loewe
(74) *Attorney, Agent, or Firm* — Drinker Biddle & Reath LLP

(57) ABSTRACT

The present invention relates to compounds according to formula (1), a method for producing these compounds and electronic devices, in particular organic electroluminescent devices containing said compounds.

16 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. §371) of PCT/EP2013/002748, filed Sep. 13, 2013, which claims benefit of European Application No. 12007040.4, filed Oct. 11, 2012, both of which are incorporated herein by reference in their entirety.

The present invention relates to materials for use in electronic devices, in particular in organic electroluminescent devices, and to electronic devices, in particular organic electroluminescent devices comprising these materials.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials employed here are increasingly organometallic complexes which exhibit phosphorescence instead of fluorescence. For quantum-mechanical reasons, an up to four-fold quantum and power efficiency is possible using organometallic compounds as phosphorescence emitters. In general, there is still a need for improvement, for example with respect to efficiency, operating voltage and lifetime, in the case of OLEDs, in particular also in the case of OLEDs which exhibit triplet emission (phosphorescence). This also applies, in particular, to OLEDs which emit in the relatively short-wave region, for example green.

The properties of phosphorescent OLEDs are not determined only by the triplet emitters employed. In particular, the other materials used, such as matrix materials, hole-blocking materials, electron-transport materials, etc., are also of particular importance here. Improvements in these materials may thus also result in significant improvements in the OLED properties. There is also still a need for improvement in the case of these materials for fluorescent OLEDs.

In accordance with the prior art, use is made, inter alia, of lactams, for example in accordance with WO 2011/116865 or WO 2011/137951, as matrix materials for phosphorescent emitters in organic electroluminescent devices. In general, further improvements are desirable here, in particular with respect to the efficiency, the lifetime and the thermal stability of the materials.

The object of the present invention is the provision of compounds which are suitable for use in a fluorescent or phosphorescent OLED, in particular a phosphorescent OLED, for example as matrix material or as electron-transport or hole-blocking material. In particular, the object of the present invention is to provide matrix materials which are suitable for green- and red- and optionally also blue-phosphorescent OLEDs.

Surprisingly, it has been found that the compounds described in greater detail below achieve this object and result in improvements in the organic electroluminescent device, in particular with respect to the lifetime, the efficiency and/or the operating voltage. This applies, in particular, to red- and green-phosphorescent electroluminescent devices, especially on use of the compounds according to the invention as matrix material. The materials are furthermore distinguished by high temperature stability. The present invention therefore relates to electronic devices, in particular organic electroluminescent devices, which comprise compounds of this type.

The present invention relates to a compound of the formula (1),

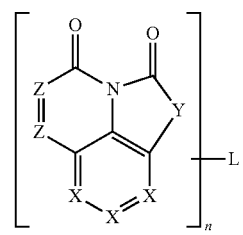

formula (1)

where the following applies to the symbols and indices used:
X is on each occurrence, identically or differently, CR or N; or precisely two adjacent groups X together stand for a group selected from NR, O or S, resulting in the formation of a five-membered ring;
Y is on each occurrence, identically or differently, Z=Z, O, S or NR, where R is not equal to H;
Z is on each occurrence, identically or differently, CR or N or the adjacent groups Z=Z together stand for a group of the formula (2),

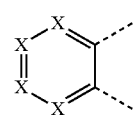

formula (2)

where X has the meanings given above and the dashed bonds indicate the linking of this group;
L is not present for n=1 and is a single bond or a divalent group for n=2 and a trivalent group for n=3 and a tetravalent group for n=4 and a pentavalent group for n=5 and a hexavalent group for n=6; L here is bonded at any desired point of the basic structure instead of a group R;
R is selected on each occurrence, identically or differently, from the group consisting of H, D, F, Cl, Br, I, CN, $NO_2$, $N(Ar^1)_2$, $N(R^1)_2$, $C(=O)Ar^1$, $C(=O)R^1$, $P(=O)(Ar^1)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^1$, where one or more non-adjacent $CH_2$ groups may be replaced by $R^1C=CR^1$, $C\equiv C$, $Si(R^1)_2$, $C=O$, $C=S$, $C=NR^1$, $P(=O)(R^1)$, SO, $SO_2$, $NR^1$, O, S or $CONR^1$ and where one or more H atoms may be replaced by D, F, Cl, Br, I, CN or $NO_2$, an aromatic or heteroaromatic ring system having 5 to 60 aromatic ring atoms, which may in each case be substituted by one or more radicals $R^1$, an aryloxy or heteroaryloxy group having 5 to 60 aromatic ring atoms, which may be substituted by one or more radicals $R^1$, an aralkyl or heteroaralkyl group having 5 to 60 aromatic ring atoms, which may be substituted by one or more radicals $R^1$, or a combination of these systems, where two or more adjacent substituents R may optionally form a monocyclic or polycyclic, aliphatic, aromatic or heteroaromatic ring system, which may be substituted by one or more radicals $R^1$;
$Ar^1$ is on each occurrence, identically or differently, an aromatic or heteroaromatic ring system having 5-30 aromatic ring atoms, which may be substituted by one or more non-aromatic radicals R¹; two radicals Ar¹ here which are bonded to the same N atom or P atom may also be bridged to one another by a single bond or a bridge selected from N(R¹), C(R¹)₂ or O;

R¹ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I, CN or an alkyl group having 1 to 10 C atoms or an alkenyl group having 2 to 10 C atoms, where two or more adjacent substituents R¹ may form a mono- or polycyclic, aliphatic, aromatic or heteroaromatic ring system with one another;

n is 1, 2, 3, 4, 5 or 6;

where the following compound is excluded from the invention:

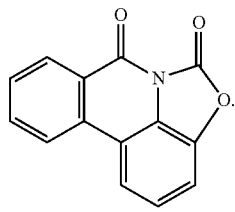 [SMILES: O=c1oc2cccc3c4ccccc4c(=O)n1c23]

An aryl group in the sense of this invention contains 6 to 60 C atoms; a heteroaryl group in the sense of this invention contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (anellated) aryl or heteroaryl group, for example naphthalene, anthracene, phenanthrene, quinoline, isoquinoline, etc. Aromatic groups which are linked to one another by a single bond, such as, for example, biphenyl, are, by contrast, not referred to as aryl or heteroaryl group, but instead as aromatic ring system.

An aromatic ring system in the sense of this invention contains 6 to 80 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which, in addition, a plurality of aryl or heteroaryl groups may be connected by a non-aromatic unit, such as, for example, a C, N or O atom. Thus, for example, systems such as fluorene, 9,9'-spirobifluorene, 9,9-diarylfluorene, triarylamine, diaryl ether, stilbene, etc., are also intended to be taken to be aromatic ring systems for the purposes of this invention, as are systems in which two or more aryl groups are connected, for example, by a short alkyl group.

For the purposes of the present invention, an aliphatic hydrocarbon radical or an alkyl group or an alkenyl or alkynyl group, which may contain 1 to 40 C atoms and in which, in addition, individual H atoms or CH₂ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoro-methyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexynylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups in accordance with the present invention may be straight-chain, branched or cyclic, where one or more non-adjacent CH₂ groups may be replaced by the above-mentioned groups; furthermore, one or more H atoms may also be replaced by D, F, Cl, Br, I, CN or NO₂, preferably F, Cl or CN, further preferably F or CN, particularly preferably CN.

An aromatic or heteroaromatic ring system having 5-60 aromatic ring atoms, which may also in each case be substituted by the above-mentioned radicals R¹ and which may be linked to the aromatic or heteroaromatic ring system via any desired positions, is taken to mean, in particular, groups derived from benzene, naphthalene, anthracene, phenanthrene, pyrene, benzanthracene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, iso-benzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from combination of these systems.

In a preferred embodiment of the invention, Y stands for a group Z═Z. Preference is thus given to a compound of the following formula (3),

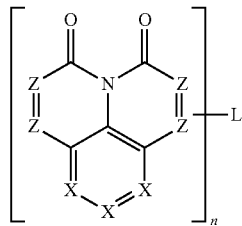

formula (3)

where the symbols and indices used have the meanings given above.

In a further preferred embodiment of the invention, the group Z═Z stands for a group of the formula (2), so that a compound of the following formula (4) arises,

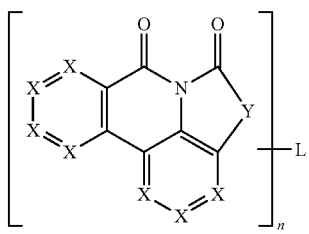

formula (4)

where the symbols and indices used have the meanings given above.

A preferred embodiment of the compounds of the formula (3) and (4) are the compounds of the following formula (5),

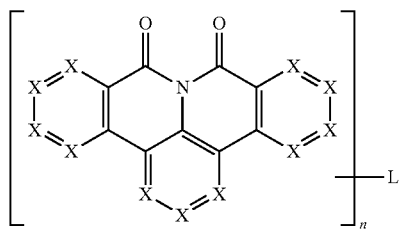

formula (5)

where the symbols and indices used have the meanings given above,

In a further preferred embodiment of the invention, n=1, 2 or 3. For n>1, the group L is preferably bonded in the para-position to the nitrogen. For n>1, it is thus preferably a structure of the following formula (6),

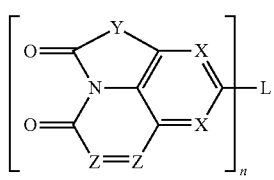

formula (6)

where n=2, 3, 4, 5 or 6 and the other symbols have the meanings given above. In particular, the other symbols have the same meanings as indicated as preferred above.

In a further preferred embodiment of the invention, a maximum of one group X per ring stands for N and the other groups X stand for CR. Particularly preferably, all groups X stand for CR.

Preference is thus given to the compounds of the following formula (7) and (8),

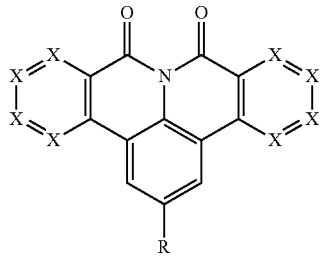

formula (7)

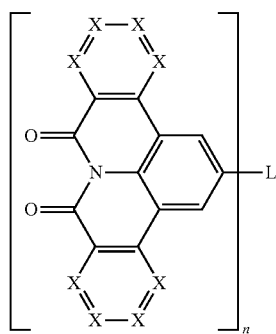

formula (8)

where n stands for 2 or 3, a maximum of one group X per ring stands for N and the other groups X stand for CR and the other symbols used have the meanings given above.

Preferred embodiments of the formulae (7) and (8) are the compounds of the following formulae (7a) and (8a),

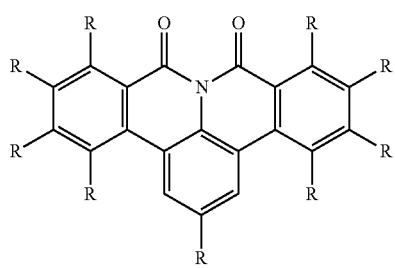

formula (7a)

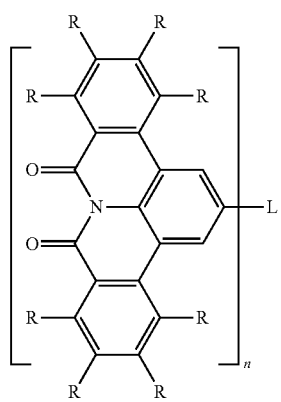

formula (8a)

where the symbols and indices used have the meanings given above.

Preferred embodiments of the formulae (7a) and (8a) are the compounds of the following formulae (7b) and (8b),

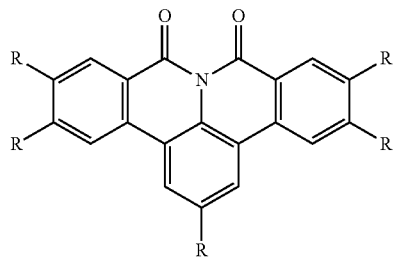

formula (7b)

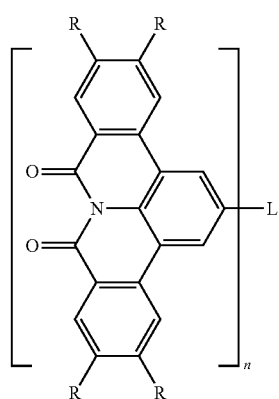

formula (8b)

where the symbols and indices used have the meanings given above.

Particularly preferred embodiments are the compounds of the following formulae (7c) and (8c),

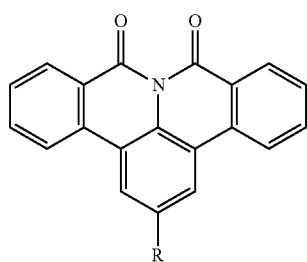

formula (7c)

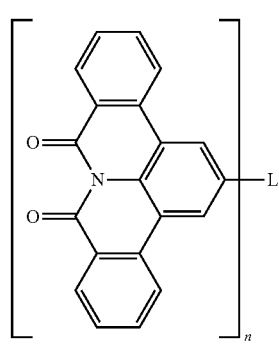

formula (8c)

where the symbols and indices used have the meanings given above,

In a further preferred embodiment of the invention, Y stands for a group NR. A further preferred embodiment of the compounds of the formula (4) are therefore the compounds of the following formula (9),

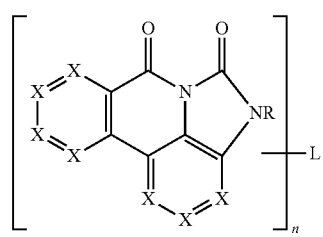

formula (9)

where the symbols and indices used have the meanings given above and the radical R bonded to the nitrogen is not equal to hydrogen.

Preferred embodiments of the compounds of the formula (9) are the compounds of the following formulae (10) and (11),

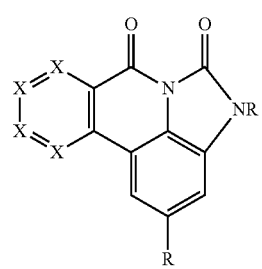

formula (10)

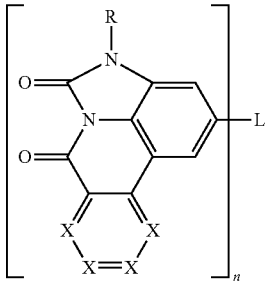

formula (11)

where n stands for 2 or 3, a maximum of one group X stands for N and the other groups X stand for CR, the other symbols used have the meanings given above and the radical R bonded to the nitrogen is not equal to hydrogen.

Preferred embodiments of the formulae (10) and (11) are the compounds of the following formulae (10a) and (11a),

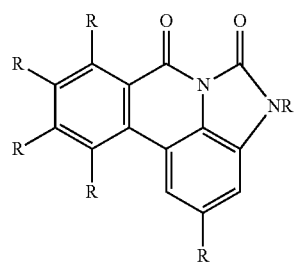

formula (10a)

formula (11a)

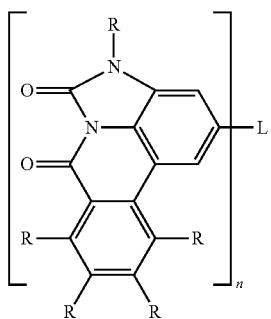

where the symbols and indices used have the meanings given above.

Preferred embodiments of the formulae (10a) and (11a) are the compounds of the following formulae (10b) and (11b), formula (10b)

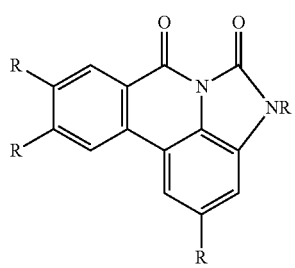

formula (11b)

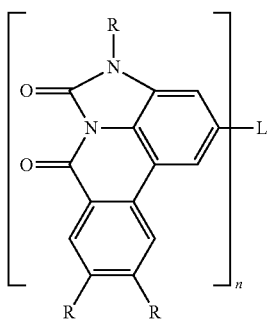

where the symbols and indices used have the meanings given above.

Particularly preferred embodiments are the compounds of the following formulae (10c) and (11c), formula (10c)

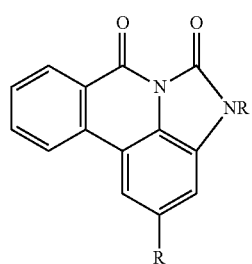

formula (11c)

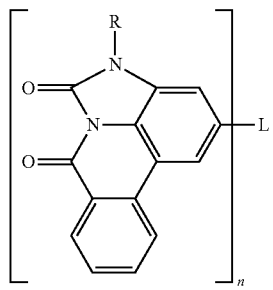

where the symbols and indices used have the meanings given above.

Preference is furthermore given to structures in which the radical R which is bonded to the nitrogen in formula (9) to (11) and (10a) to (11c) stands for a group C(=O)Ar¹, which forms a ring with an adjacent radical R. This then gives access to compounds of the following formulae (12), formula (12)

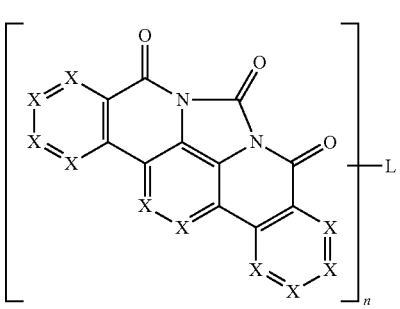

where the symbols and indices used have the same meanings as described above. The same preferences as described above also apply to the symbols and indices used in formula (12).

L in the compounds of the formula (1) or the preferred compounds indicated above preferably stands for a single bond, $CR_2$, O, NR or C(=O) for n=2 or for N for n=3 or for an aromatic or heteroaromatic ring system having 5 to 24 aromatic ring atoms, which may be substituted by one or more radicals R, for n≥2. Suitable aromatic or heteroaromatic ring systems are ortho-, meta- or para-phenylene, fluorene, spirobifluorene, pyridine, pyrimidine, triazine, carbazole, dibenzofuran, triphenylamine or combinations of two or three of these groups. The aromatic or heteroaromatic ring system here is a divalent system for n=2, a trivalent system for n=3, etc. Particularly preferably, n=2, and L stands for a single bond.

The compounds according to the invention preferably contain at least one group R which is not equal to hydrogen or deuterium, and/or it is a compound where n>1.

The radical R that is not equal to hydrogen is preferably selected from the group consisting of an aromatic or heteroaromatic ring system having 5 to 24 aromatic ring atoms, which may be substituted by one or more radicals R¹. This also applies, in particular, to the radical R which is bonded to a nitrogen atom if Y stands for NR. Suitable aryl or heteroaryl groups of which the aromatic ring system are composed are preferably selected from the group consisting of benzene, naphthalene, phenanthrene, triphenylene, pyridine, thiophene, furan, pyrrole, carbazole, fluorene, benzofuran, benzothiophene, dibenzofuran, dibenzothiophene, quinoline, isoquinoline, phenanthridine, phenanthroline, azacarbazole, imidazole and benzimidazole, each of which may be substituted by one or more radicals $R^1$. Furthermore preferred radicals R are aromatic or heteroaromatic amino groups, where the aryl or heteroaryl groups may be substituted by one or more radicals $R^1$.

If the compound according to the invention is employed as matrix material for a phosphorescent emitter, none of the aryl or heteroaryl groups which form the aromatic or heteroaromatic ring system or which are present in the aromatic or heteroaromatic amino group preferably contains more than two aromatic six-membered rings condensed directly onto one another. The radicals R preferably contain absolutely no aromatic six-membered rings condensed directly onto one another. An aryl or heteroaryl group containing not more than two aromatic six-membered rings condensed directly onto one another is taken to mean simple aryl or heteroaryl groups, such as, for example, benzene or pyridine, or aryl or heteroaryl groups containing precisely two aromatic six-membered rings condensed onto one another, such as, for example, naphthalene or quinoline. This is furthermore taken to mean heteroaryl groups in which aromatic five-membered rings and six-membered rings, but not aromatic six-membered rings, are condensed directly onto one another, such as, for example, carbazole, dibenzofuran, dibenzothiophene or benzimidazole. Furthermore, phenanthrene or triphenylene may also be suitable.

Preferred groups R are selected from the group consisting of benzene, biphenyl, in particular ortho-, meta- or para-biphenyl, terphenyl, in particular ortho-, meta-, para- or branched terphenyl, quaterphenyl, in particular ortho-, meta- or para-linked, linear or branched quaterphenyl, fluorene, in particular 1-, 2-, 3- or 4-fluorene, spirobifluorene, in particular 1-, 2-, 3- or 4-spirobifluorene, 1- or 2-naphthalene, pyrrole, furan, thiophene, indole, benzofuran, benzothiophene, carbazole, in particular 1-, 2-, 3- or 4-carbazole or N-carbazole, dibenzothiophene, in particular 1-, 2-, 3- or 4-dibenzothiophene, dibenzofuran, in particular 1-, 2-, 3- or 4-dibenzofuran, 1,3,5-triazine, pyridine, pyrimidine, pyrazine, pyridazine, indenocarbazole, bridged carbazole, indolocarbazole, phenanthrene, triphenylene or combinations of two or three of these groups. These groups may each be substituted by one or more radicals $R^1$.

If R stands for an aromatic or heteroaromatic ring system, this is then preferably selected from the groups of the following formulae (R-1) to (R-33), formula (R-1)

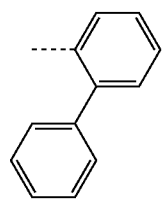

formula (R-2)

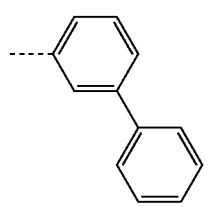

formular (R-3)

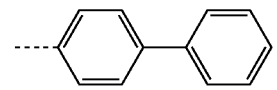

formula (R-4)

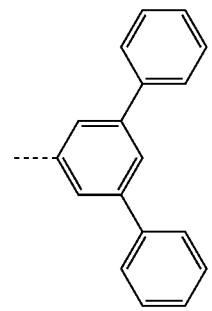

formula (R-5)

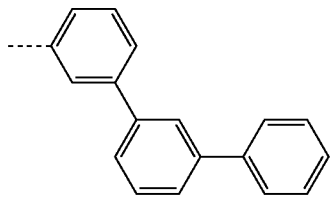

formula (R-6)

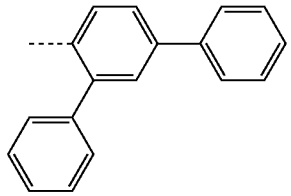

formula (R-7)

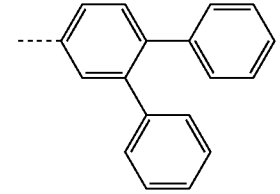

formula (R-8)

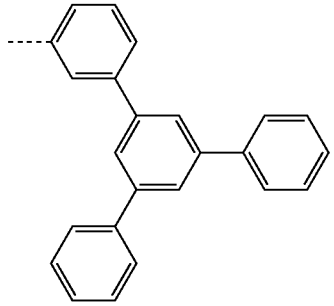

formula (R-9)

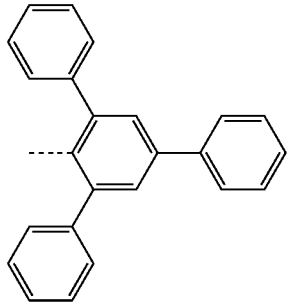

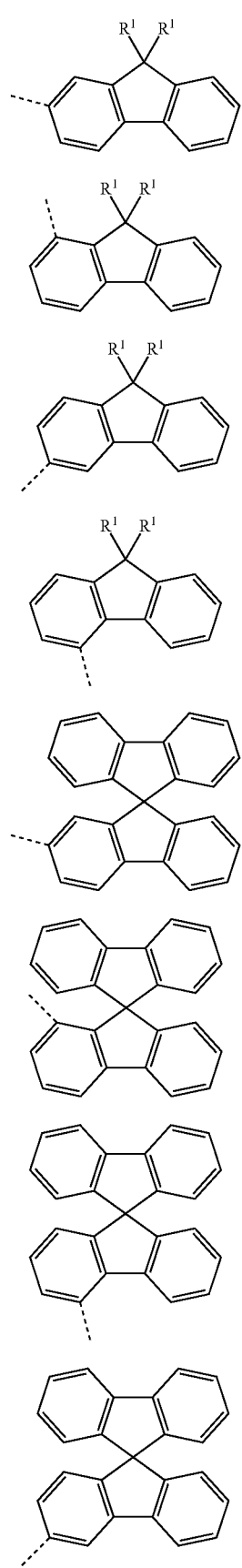
formula (R-10)
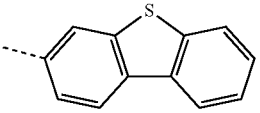
formula (R-11)
formula (R-12)
formula (R-13)
formula (R-14)
formula (R-15)
formula (R-16)
formula (R-17)
formula (R-18)
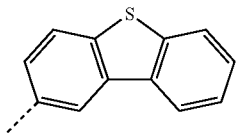
formula (R-19)
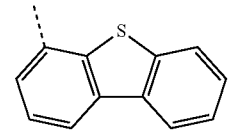
formula (R-20)
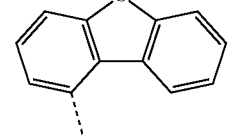
formula (R-21)
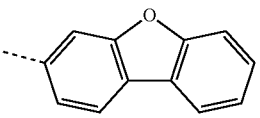
formula (R-22)
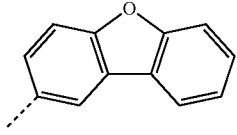
formula (R-23)
formula (R-24)
formula (R-25)
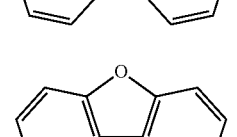
formula (R-26)
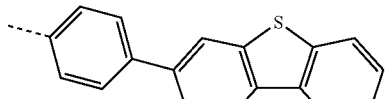
formula (R-27)
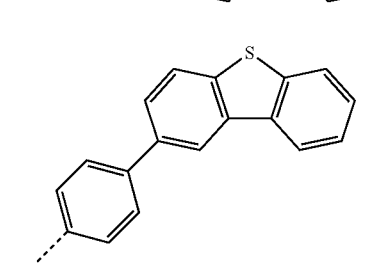

-continued
formula (R-28)
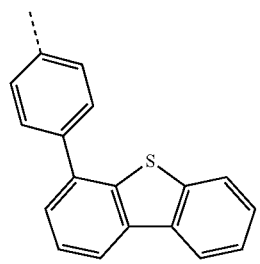
formula (R-29)
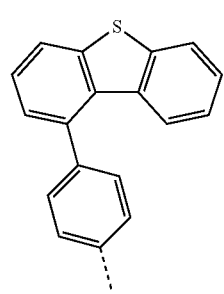
formula (R-30)
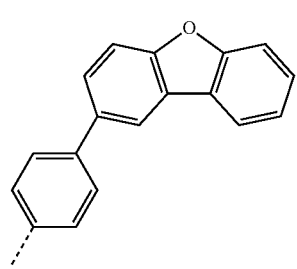
formula (R-31)
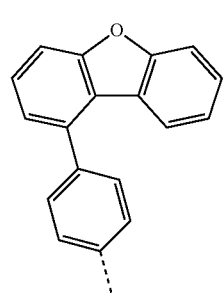
formula (R-32)
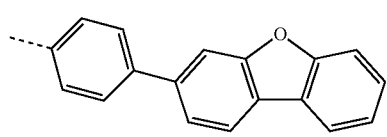
formula (R-33)
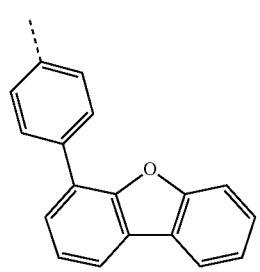
formula (R-34)
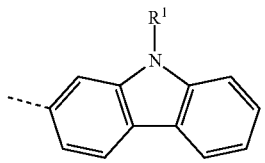
formula (R-35)
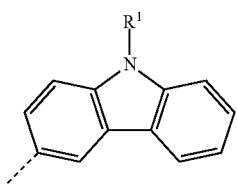
formula (R-36)
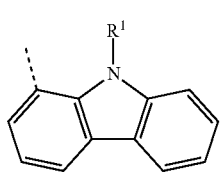
formula (R-37)
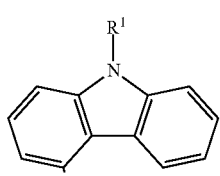
formula (R-38)
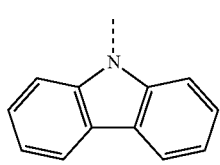
formula (R-39)
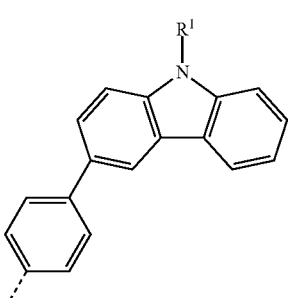
formula (R-40)
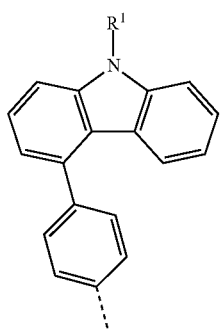

-continued formula (R-41)

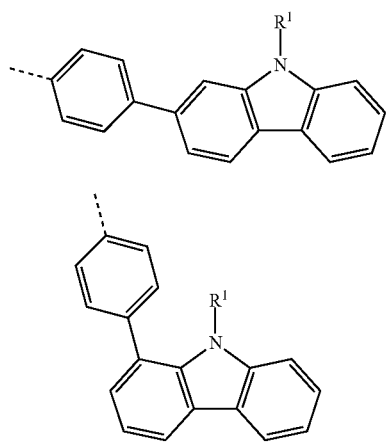

formula (R-42)

where the dashed bond indicates the bonding to the basic structure, and the groups may each be substituted by one or more radicals R¹, but are preferably unsubstituted.

If the compounds according to the invention are used as electron-transport material, it is preferred if at least one of the groups R and/or L stands for an electron-deficient heteroaromatic ring system or —C(═O)Ar¹ or —P(═O)(Ar¹)₂. Electron-deficient heteroaromatic ring systems are, in accordance with the invention, five-membered heteroaromatic ring systems having at least two heteroatoms or six-membered heteroaromatic ring systems, onto which one or more aromatic or heteroaromatic groups may also in each case be condensed, for example substituted or unsubstituted imidazoles, pyrazoles, thiazoles, oxazoles, oxadiazoles, triazoles, pyridines, pyrazines, pyrimidines, pyridazines, triazines, benzimidazoles, etc., in particular those as are shown below. Preferred groups R and/or L are furthermore also substituted or unsubstituted condensed aryl groups, in particular naphthalene, anthracene, pyrene, phenanthrene, triphenylene and benzanthracene.

If the compound according to the invention or the preferred compounds indicated above is employed as matrix material for a phosphorescent emitter or as electron-transport material, it is furthermore preferred if at least one group R represents a simple aromatic group or an electron-deficient group, in particular selected from structures of the following formulae (13) to (16) for R or the formulae (17), (18) or (19) for L, formula (13)

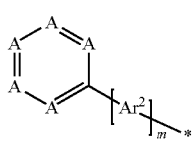

formula (14)

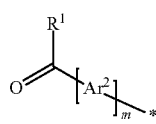

formula (15)

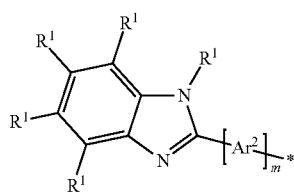

formula (16)

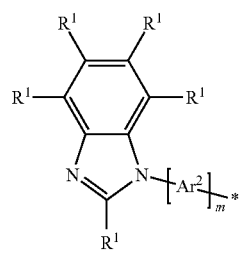

and/or at least one divalent or trivalent group L preferably stands for a group of the following formulae (17) to (19), formula (17)

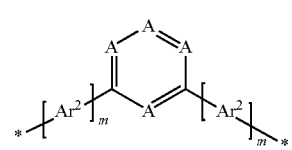

formula (18)

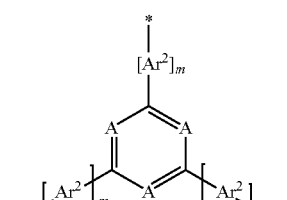

formula (19)

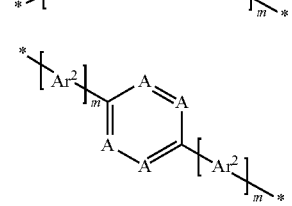

where R¹ has the meaning given above, * indicates the position of the bonding of the group of the formula (13) to (19) and furthermore:

A is on each occurrence, identically or differently, CR¹ or N, with the proviso that no, one, two or three groups A stand for N;

Ar² is, identically or differently on each occurrence, a divalent aromatic or heteroaromatic ring system having 5 to 16 C atoms, which may be substituted by one or more radicals R¹;

m is on each occurrence, identically or differently, 0 or 1.

Preferred as matrix material for phosphorescent emitters are furthermore also in general the aromatic and heteroaromatic ring systems indicated above which are generally indicated as preferred radicals R.

In a particularly preferred embodiment of the invention, at least one substituent R stands for a group of the above-mentioned formula (R-1) to (R-17) or formula (13), and/or at least one group L stands for a group of the above-mentioned formulae (17) to (19), where in each case two or three symbols A stand for N and the other symbols A stand for CR¹. Particularly preferred groups R are therefore the groups of the following formulae (20) to (26), and particularly preferred groups L are the groups of the following formulae (27) to (34),

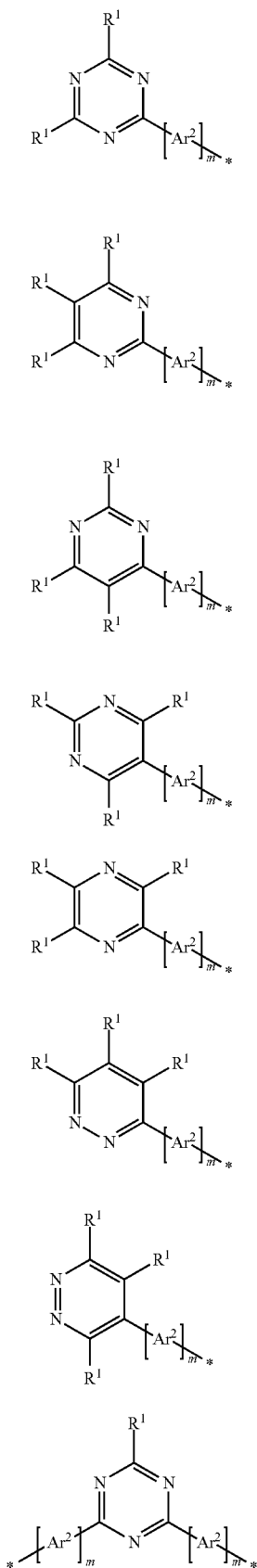
formula (20)
formula (21)
formula (22)
formula (23)
formula (24)
formula (25)
formula (26)
formula (27)
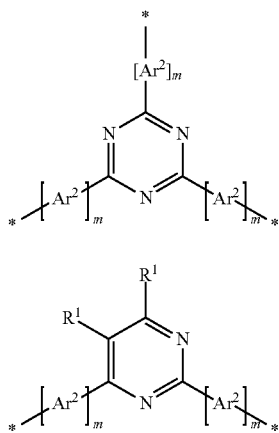
formula (28)
formula (29)
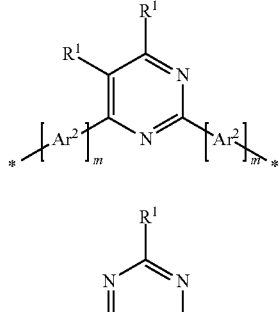
formula (30)
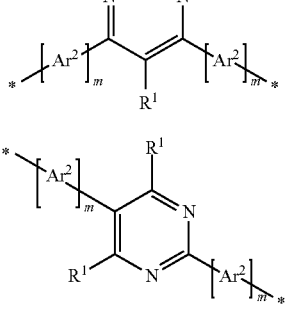
formula (31)
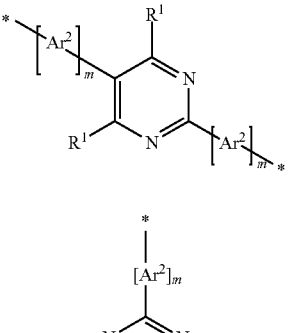
formula (32)
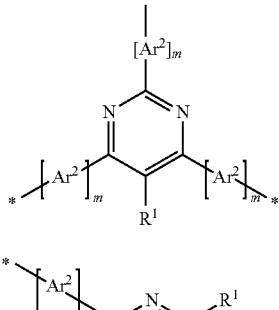
formula (33)
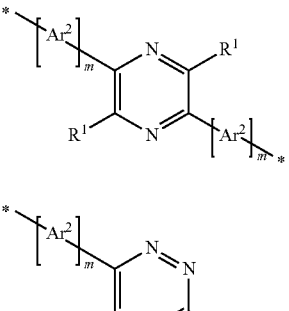
formula (34)
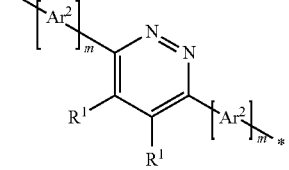
where the symbols and indices used have the meanings given above,
If R stands for a group of the formula (20), $R^1$ in this group then preferably stands for an aromatic or heteroaromatic ring system having 5 to 24 aromatic ring atoms, which may be substituted by one or more alkyl groups having 1 to 10 C atoms, in particular for phenyl, biphenyl, in particular ortho-, meta- or para-biphenyl, terphenyl, in particular ortho-, meta-, para- or branched terphenyl, or quaterphenyl, in particular ortho-, meta-, para- or branched quaterphenyl.

If R stands for a group of the formula (21) to (34), $R^1$ in these groups then preferably stands, identically or differently on each occurrence, for H, D or an aromatic or heteroaromatic ring system having 5 to 24 aromatic ring atoms, which may be substituted by one or more alkyl groups having 1 to 10 C atoms, in particular for H or phenyl, biphenyl, in particular ortho-, meta- or para-biphenyl, terphenyl, in particular ortho-, meta-, para- or branched terphenyl, or quaterphenyl, in particular ortho-, meta-, para- or branched quaterphenyl.

If the compound according to the invention is employed as matrix material for a phosphorescent emitter, it may furthermore be preferred if at least one substituent R is selected from the group consisting of triaryl- or heteroarylamine derivatives, carbazole derivatives, indenocarbazole derivatives, indolocarbazole derivatives, azacarbazole derivatives, indole derivatives, furan derivatives, benzofuran derivatives, dibenzofuran derivatives, thiophene derivatives, benzothiophene derivatives or dibenzothiophene derivatives, each of which may be substituted by one or more radicals $R^1$, or at least one substituent R stands for —N(Ar$^1$)$_2$. These groups are preferably selected from the groups of the following formulae (35) to (59),

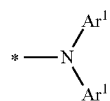
formula (35)

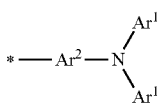
formula (36)

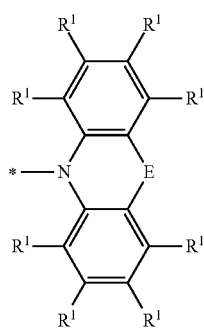
formula (37)

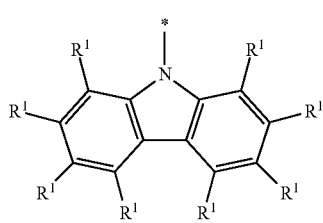
formula (38)

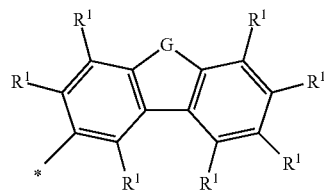
formula (39)

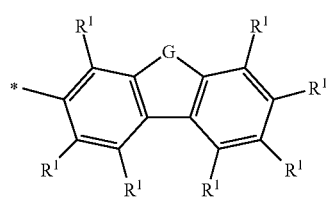
formula (40)

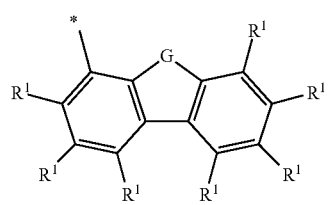
formula (41)

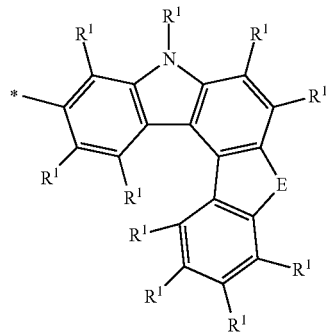
formula (42)

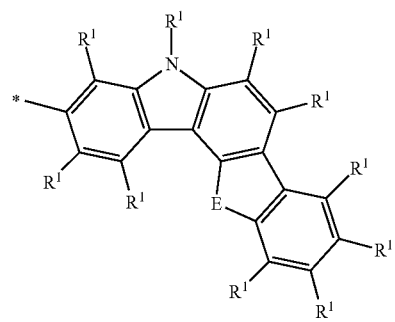
formula (43)

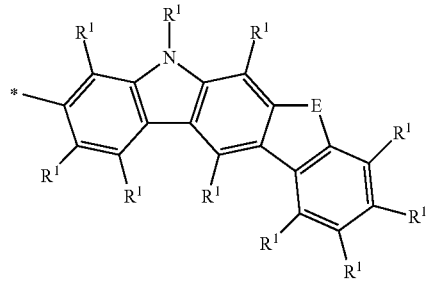
formula (44)

-continued
formula (45)
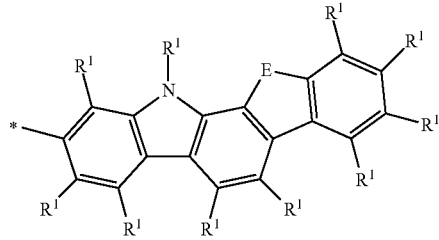
formula (46)
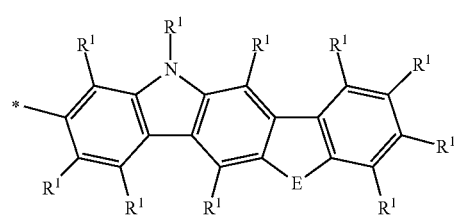
formula (47)
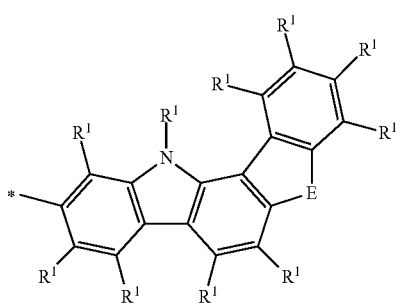
formula (48)
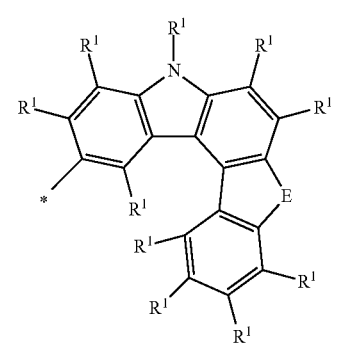
formula (49)
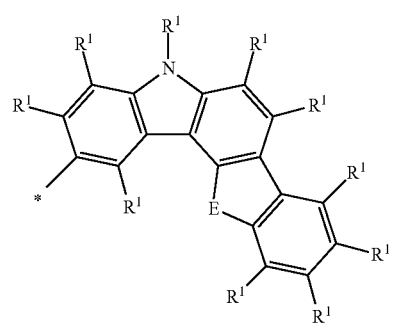
formula (50)
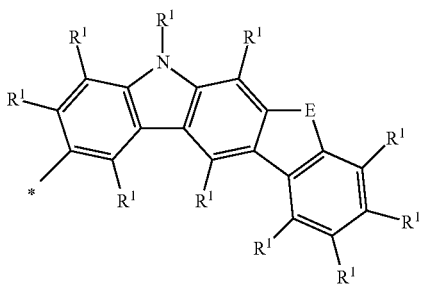
formula (51)
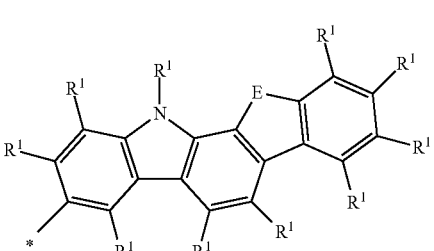
formula (52)
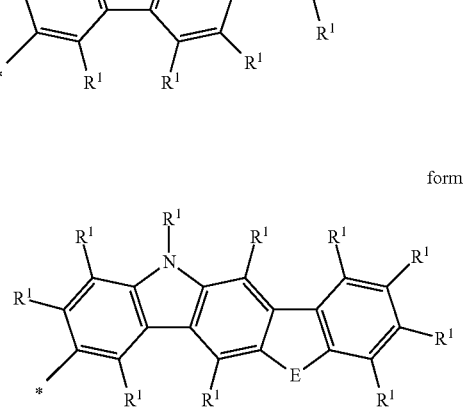
formula (53)
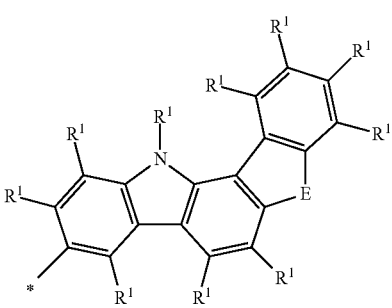
formula (54)
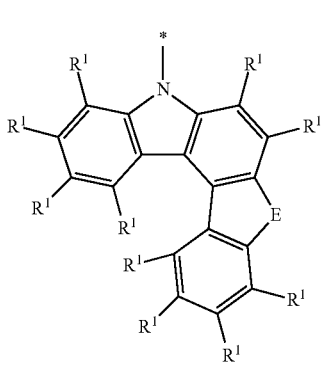

formula (55)
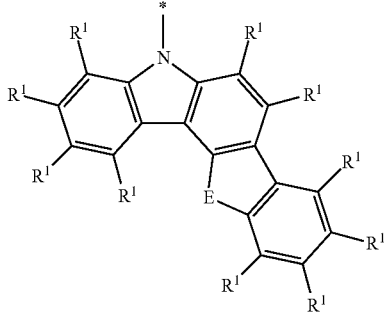

formula (56)
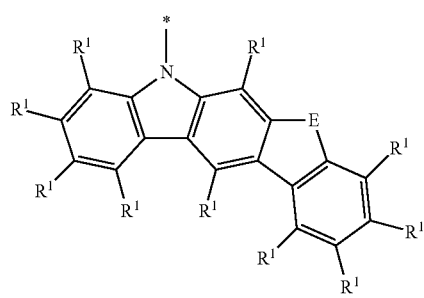

formula (57)
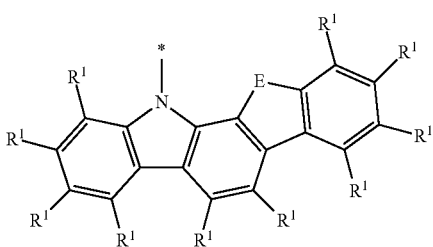

formula (58)
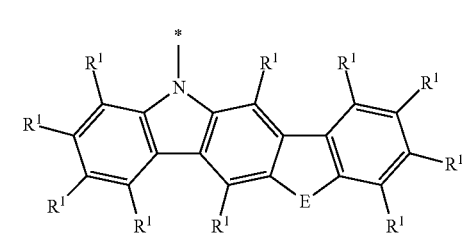

formula (59)
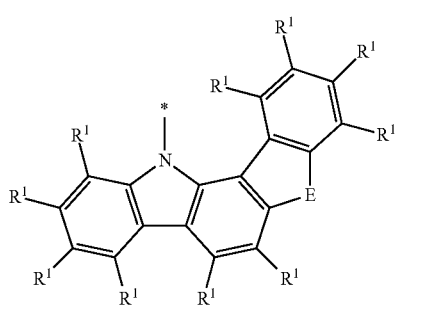

where * indicates the position of the bonding of the group, the symbols used have the meanings given above and furthermore:

E is selected from the group consisting of $C(R^1)_2$, $NR^1$, O or S;

G is selected from the group consisting of $NR^1$, O or S.

The preferred embodiments indicated above can be combined with one another as desired. In a particularly preferred embodiment of the invention, the preferences indicated above arise simultaneously.

If the compounds of the formula (1) or the preferred embodiments are used as matrix material for a fluorescent emitter or as fluorescent emitter, it is preferred if at least one of the radicals R contains a group which is selected from naphthalene, anthracene, phenanthrene, pyrene and/or benzanthracene, each of which may also be substituted by one or more groups $R^1$.

In a preferred embodiment of the invention, the radicals R in the compounds according to the invention which do not stand for the groups indicated above are selected, identically or differently on each occurrence, from the group consisting of H, D, F, CN, $N(Ar^2)_2$, $C(=O)Ar^2$, a straight-chain alkyl or alkoxy group having 1 to 10 C atoms or a branched or cyclic alkyl or alkoxy group having 3 to 10 C atoms or an alkenyl group having 2 to 10 C atoms, each of which may be substituted by one or more radicals $R^2$, where one or more non-adjacent $CH_2$ groups may be replaced by O and where one or more H atoms may be replaced by D or F or an aromatic or heteroaromatic ring system having 5 to 30 aromatic ring atoms, which may in each case be substituted by one or more radicals $R^2$. R is particularly preferably selected, identically or differently on each occurrence, from the group consisting of H, a straight-chain alkyl group having 1 to 10 C atoms or a branched or cyclic alkyl group having 3 to 10 C atoms, each of which may be substituted by one or more radicals $R^2$, or an aromatic or heteroaromatic ring system having 5 to 18 aromatic ring atoms, which may in each case be substituted by one or more radicals $R^2$.

For compounds which are processed by vacuum evaporation, the alkyl groups preferably have not more than five C atoms, particularly preferably not more than 4 C atoms, very particularly preferably not more than 1 C atom. For compounds which are processed from solution, suitable compounds are also those which are substituted by alkyl groups having up to 10 C atoms or which are substituted by oligoarylene groups, for example ortho-, meta-, para- or branched terphenyl or quaterphenyl groups.

In a particularly preferred embodiment of the invention, the preferences indicated above arise simultaneously.

Examples of preferred compounds according to the invention are the compounds depicted in the following table.

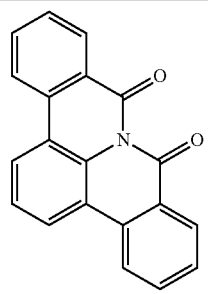 [SMILES: O=c1c2ccccc2c2cccc3c4ccccc4c(=O)n1c23]

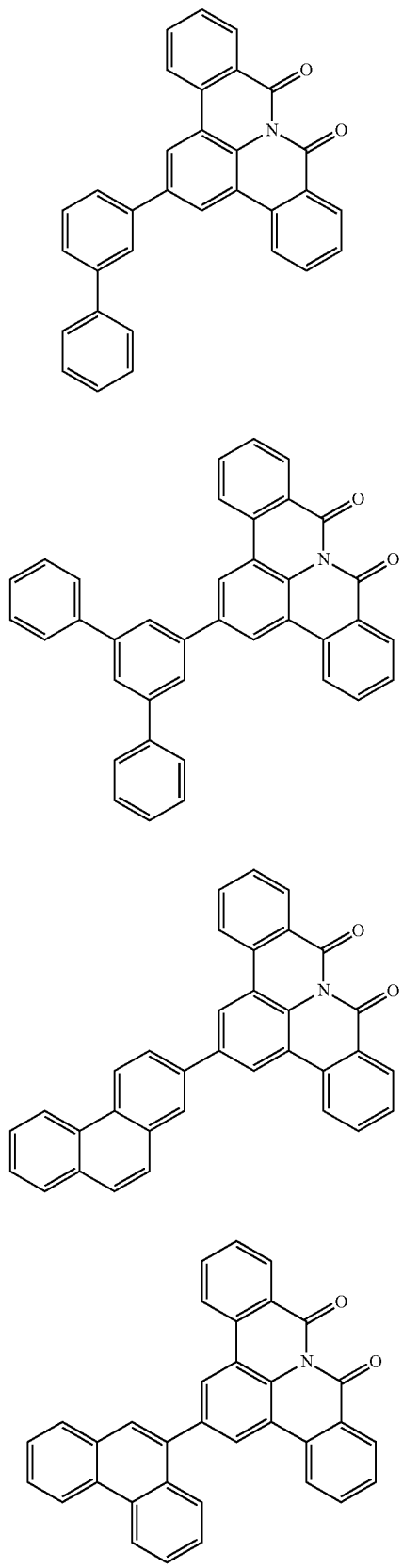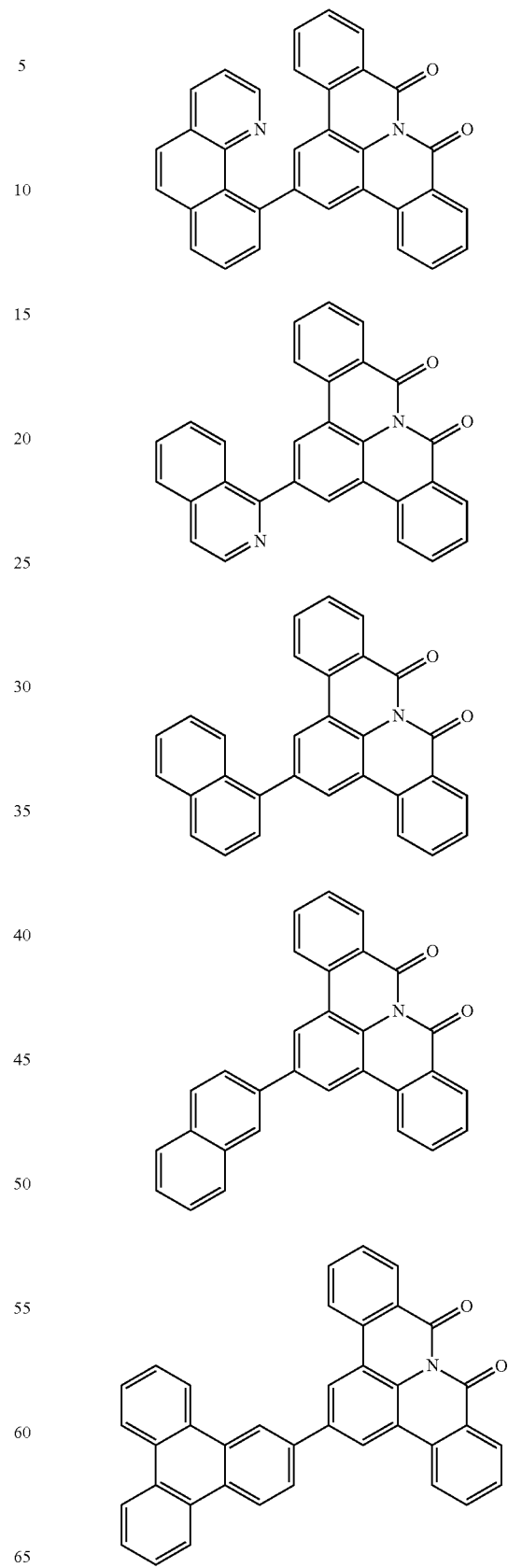

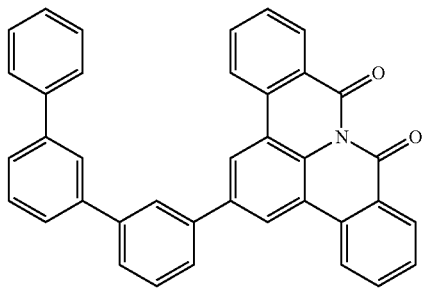 [SMILES: O=c1c2ccccc2c2cc(-c3cccc(-c4cccc(-c5ccccc5)c4)c3)cc3c4ccccc4c(=O)n1c23]
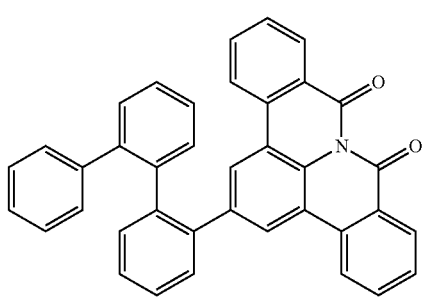 [SMILES: O=c1c2ccccc2c2cc(-c3ccccc3-c3ccccc3-c3ccccc3)cc3c4ccccc4c(=O)n1c23]
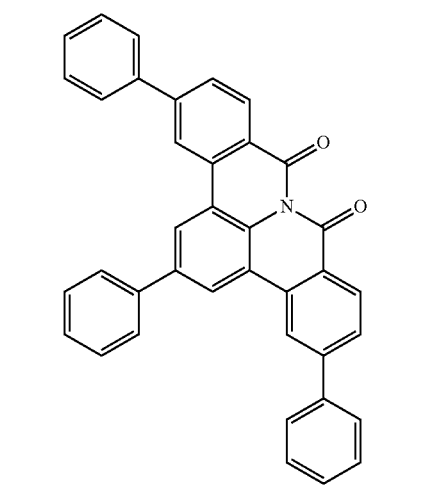 [SMILES: O=c1c2ccc(-c3ccccc3)cc2c2cc(-c3ccccc3)cc3c4cc(-c5ccccc5)ccc4c(=O)n1c23]
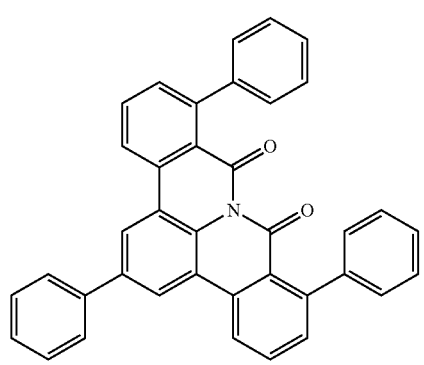 [SMILES: O=c1c2c(-c3ccccc3)cccc2c2cc(-c3ccccc3)cc3c4cccc(-c5ccccc5)c4c(=O)n1c23]
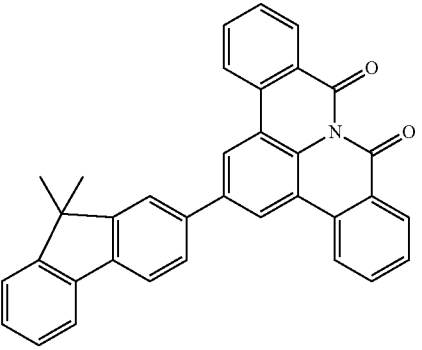 [SMILES: CC1(C)c2ccccc2-c2ccc(-c3cc4c5ccccc5c(=O)n5c(=O)c6ccccc6c(c3)c45)cc21]
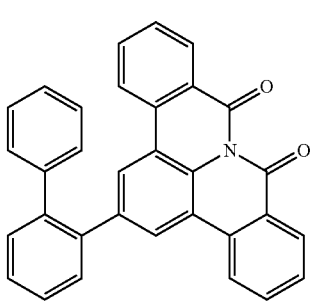 [SMILES: O=c1c2ccccc2c2cc(-c3ccccc3-c3ccccc3)cc3c4ccccc4c(=O)n1c23]
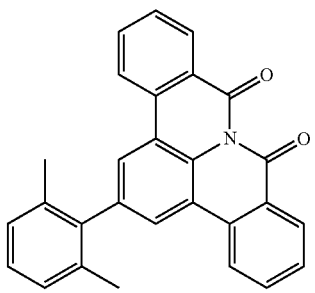 [SMILES: Cc1cccc(C)c1-c1cc2c3ccccc3c(=O)n3c(=O)c4ccccc4c(c1)c23]
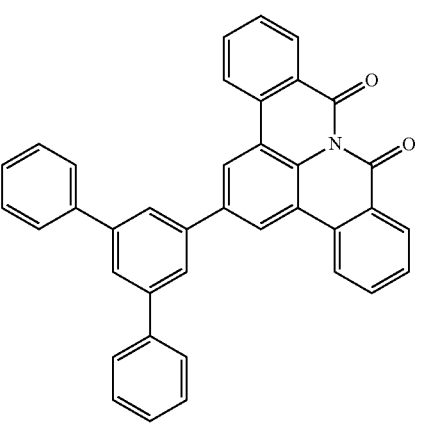 [SMILES: O=c1c2ccccc2c2cc(-c3cc(-c4ccccc4)cc(-c4ccccc4)c3)cc3c4ccccc4c(=O)n1c23]

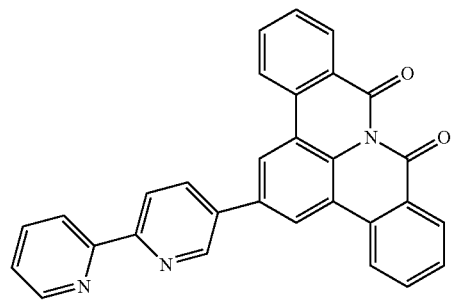 [SMILES: O=c1c2ccccc2c2cc(-c3ccc(-c4ccccn4)nc3)cc3c4ccccc4c(=O)n1c23]
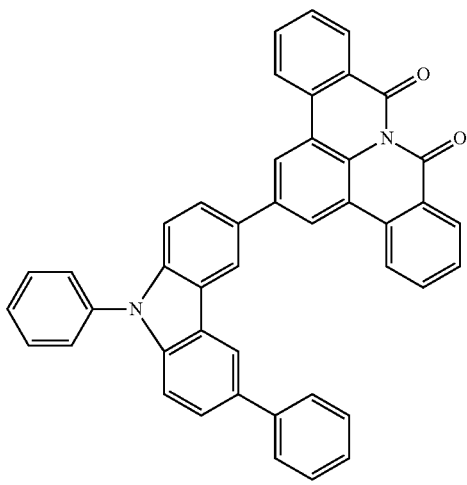
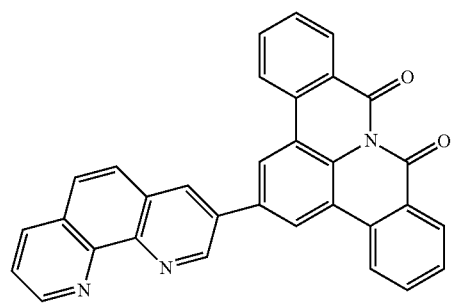 [SMILES: O=c1c2ccccc2c2cc(-c3cnc4c(ccc5cccnc54)c3)cc3c4ccccc4c(=O)n1c23]
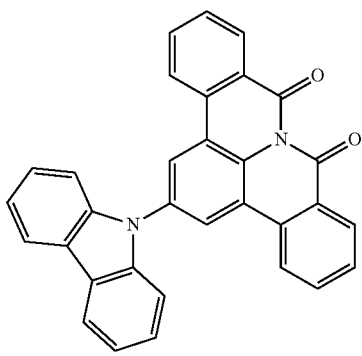
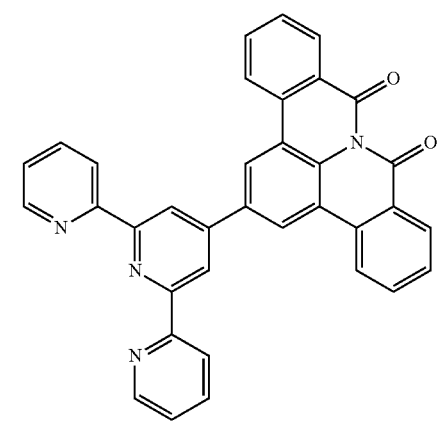 [SMILES: O=c1c2ccccc2c2cc(-c3cc(-c4ccccn4)nc(-c4ccccn4)c3)cc3c4ccccc4c(=O)n1c23]
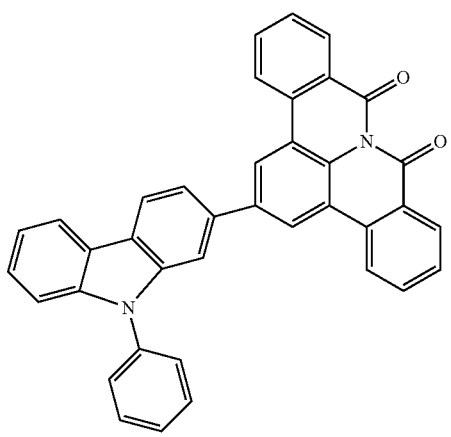
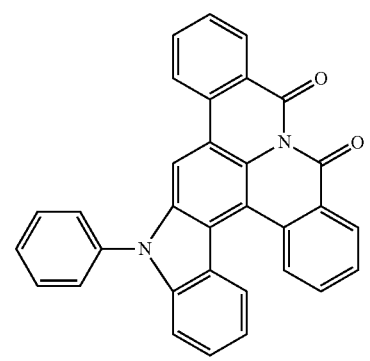 [SMILES: O=c1c2ccccc2c2cc3c(c4ccccc4n3-c3ccccc3)c3c4ccccc4c(=O)n1c23]

33
-continued
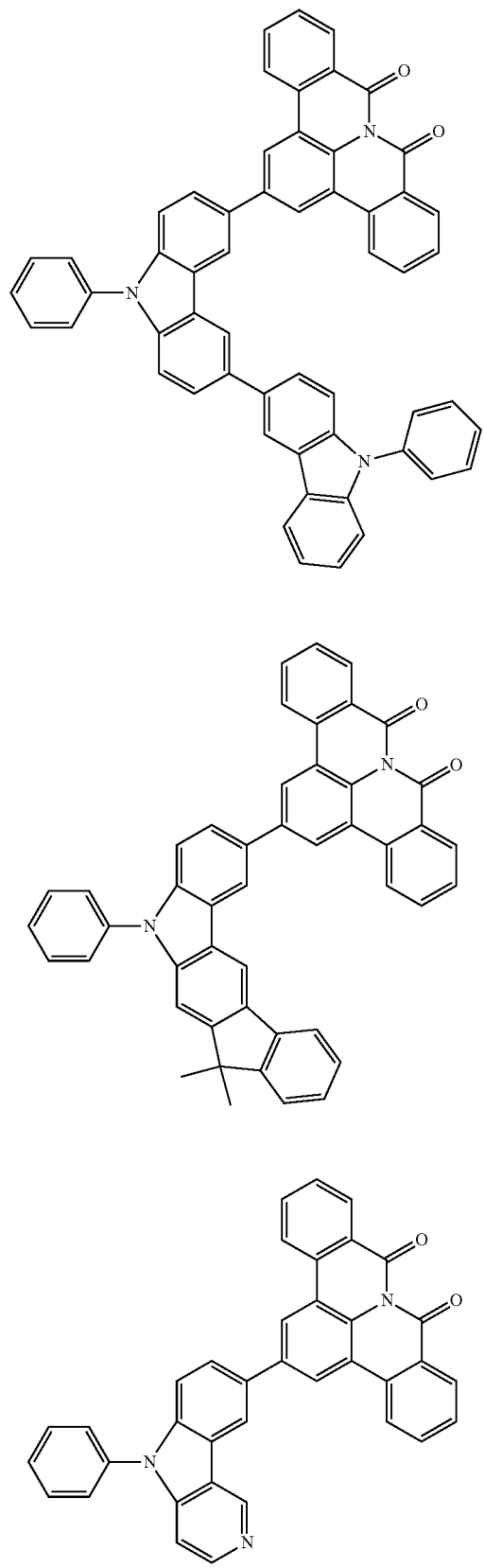
34
-continued
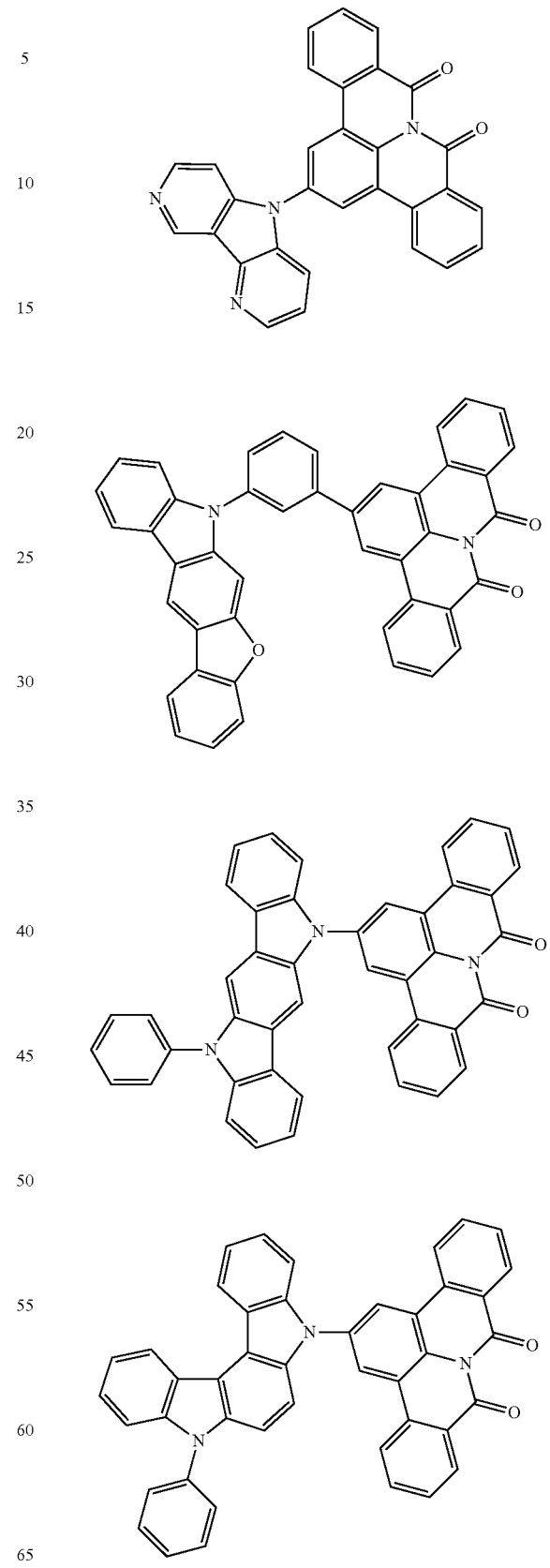

| 35<br>-continued | 36<br>-continued |
|---|---|
| 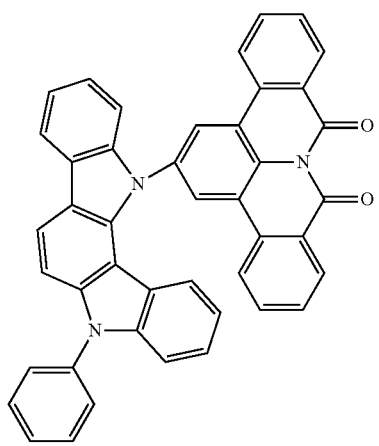 [SMILES: O=c1c2ccccc2c2cc(-n3c4ccccc4c4ccc5c(c6ccccc6n5-c5ccccc5)c43)cc3c4ccccc4c(=O)n1c23] | 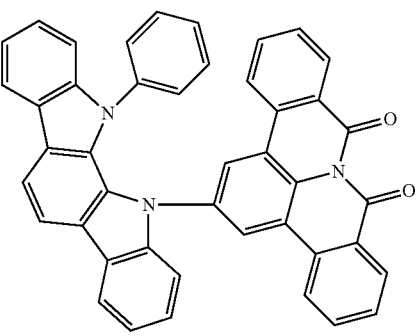 |
| 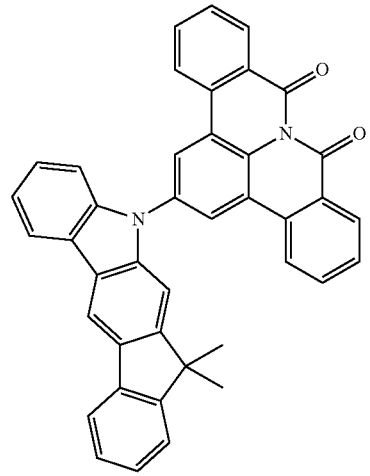 [SMILES: CC1(C)c2ccccc2-c2cc3c4ccccc4n(-c4cc5c6ccccc6c(=O)n6c(=O)c7ccccc7c(c4)c56)c3cc21] | 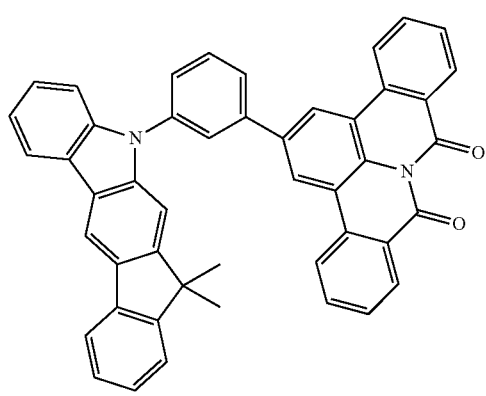 |
| 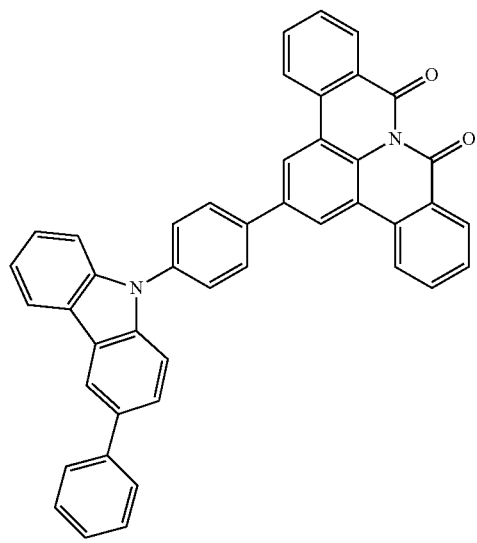 [SMILES: O=c1c2ccccc2c2cc(-c3ccc(-n4c5ccccc5c5cc(-c6ccccc6)ccc54)cc3)cc3c4ccccc4c(=O)n1c23] | 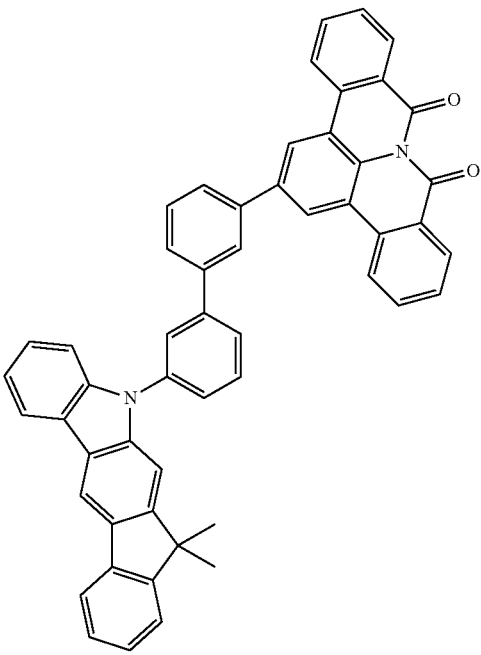 [SMILES: CC1(C)c2ccccc2-c2cc3c4ccccc4n(-c4cccc(-c5cccc(-c6cc7c8ccccc8c(=O)n8c(=O)c9ccccc9c(c6)c78)c5)c4)c3cc21] |

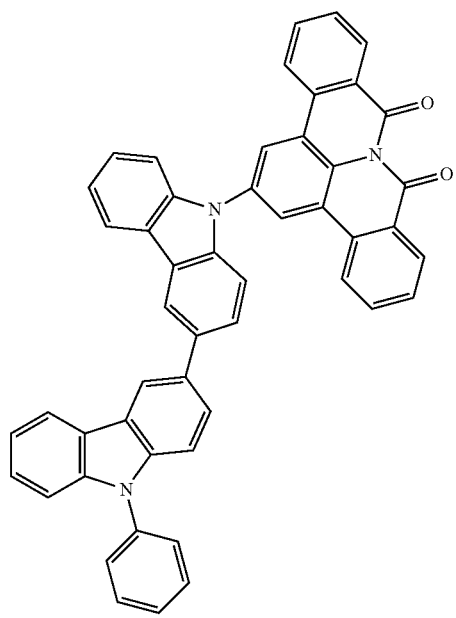 [SMILES: O=c1c2ccccc2c2cc(-n3c4ccccc4c4cc(-c5ccc6c(c5)c5ccccc5n6-c5ccccc5)ccc43)cc3c4ccccc4c(=O)n1c23]
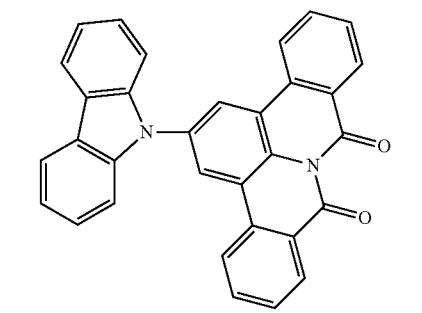 [SMILES: O=c1c2ccccc2c2cc(-n3c4ccccc4c4ccccc43)cc3c4ccccc4c(=O)n1c23]
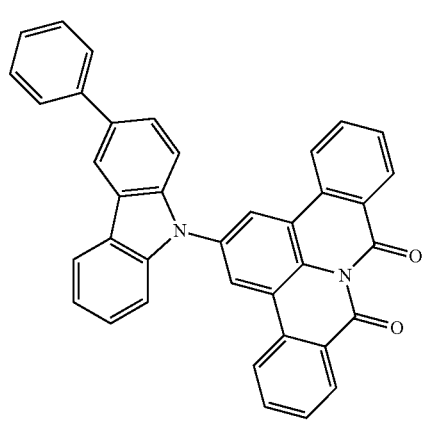 [SMILES: O=c1c2ccccc2c2cc(-n3c4ccccc4c4cc(-c5ccccc5)ccc43)cc3c4ccccc4c(=O)n1c23]
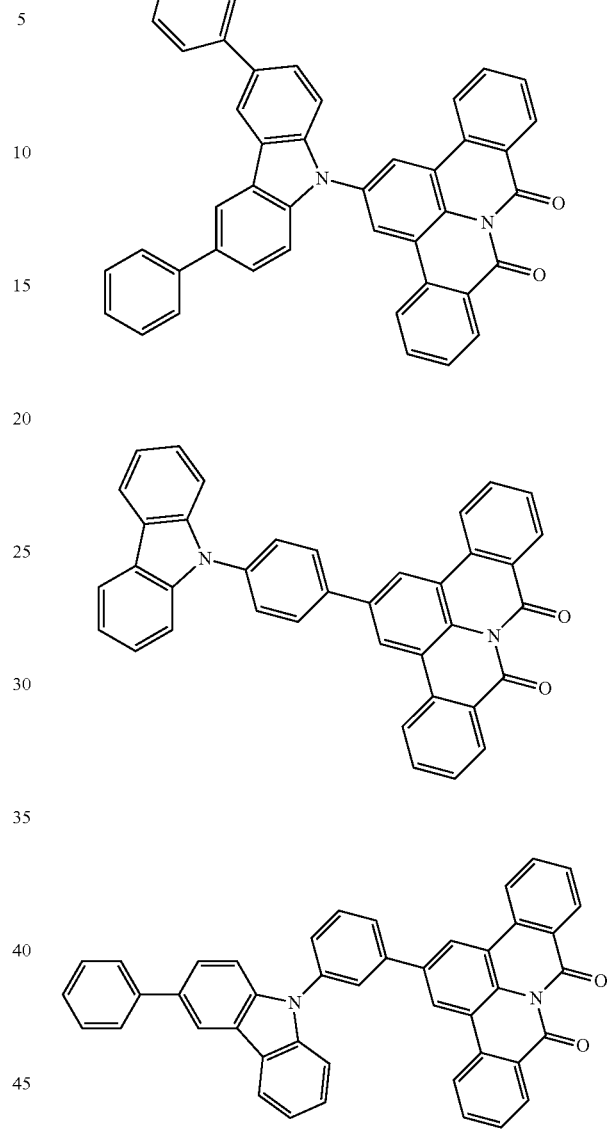
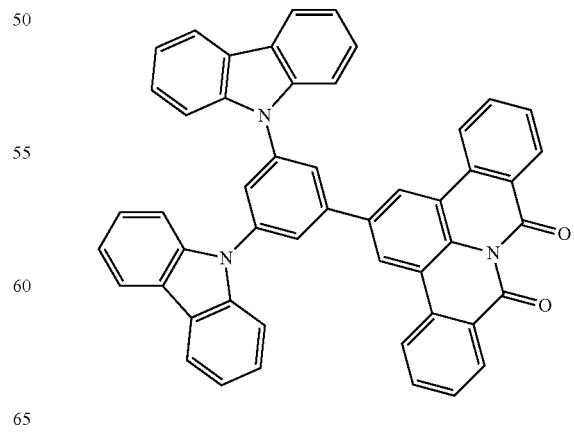

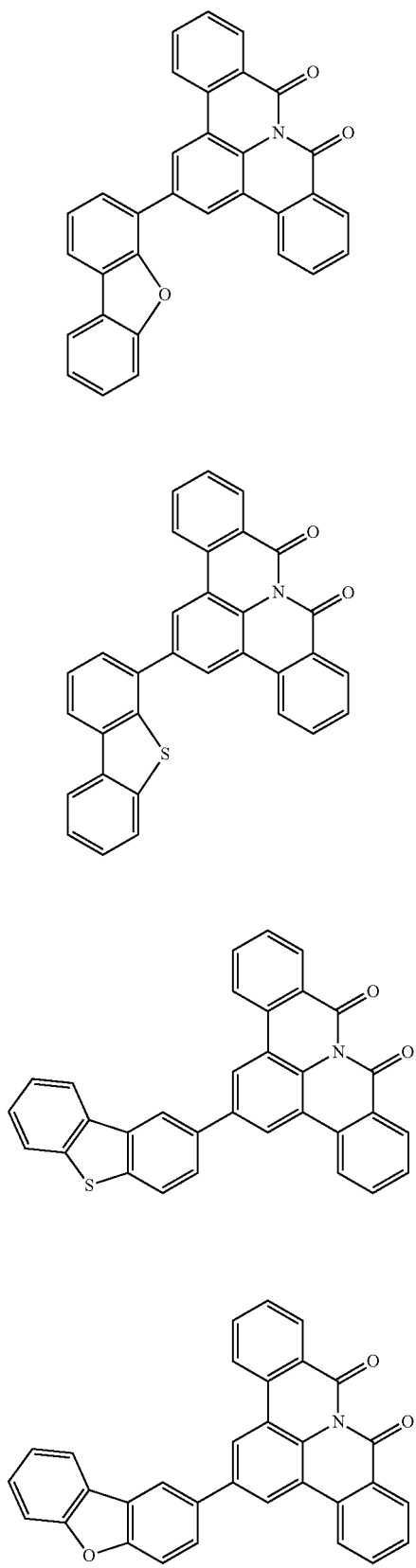
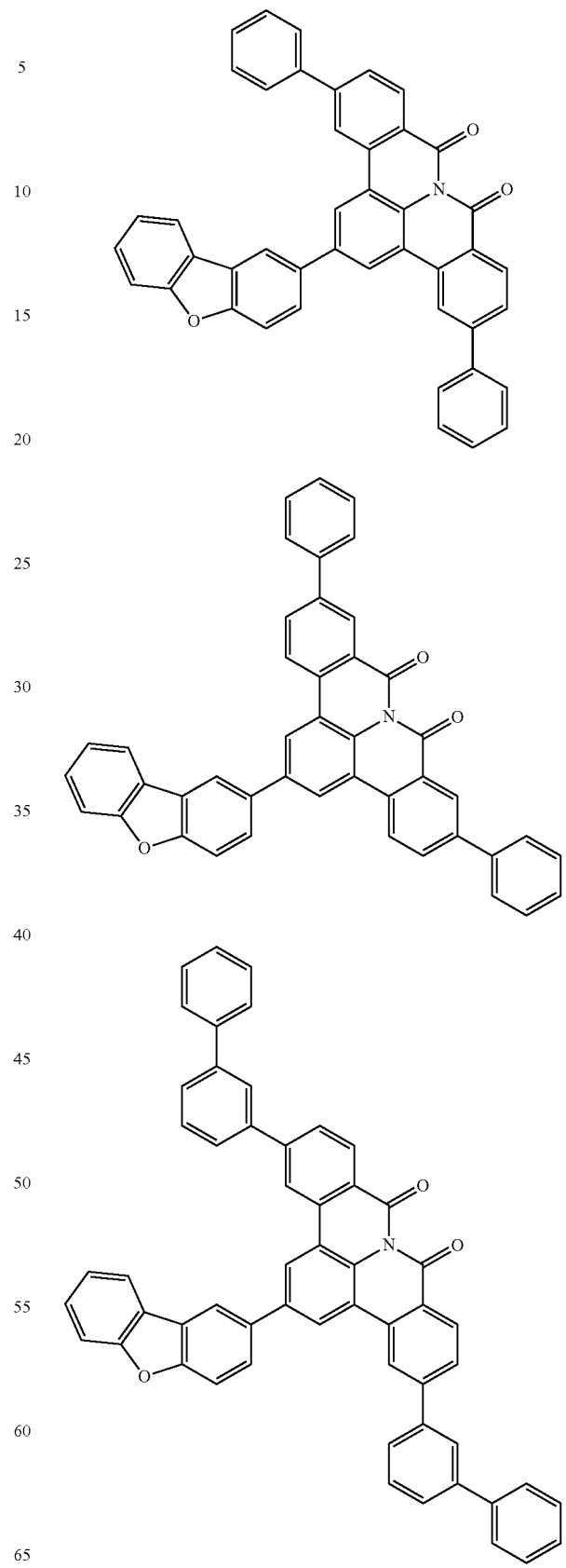

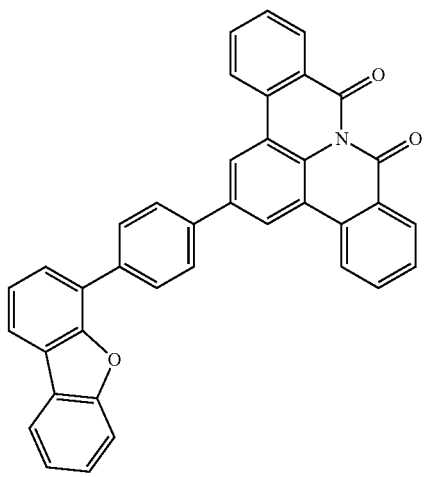 [SMILES: O=c1c2ccccc2c2cc(-c3ccc(-c4cccc5c4oc4ccccc45)cc3)cc3c4ccccc4c(=O)n1c23]
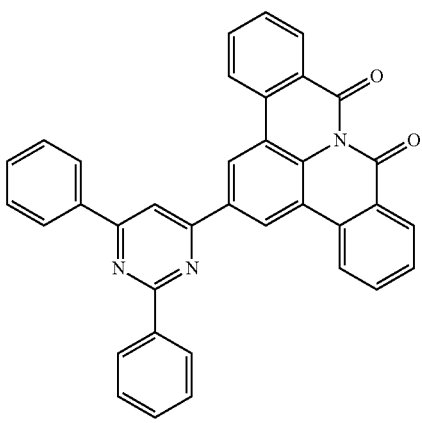
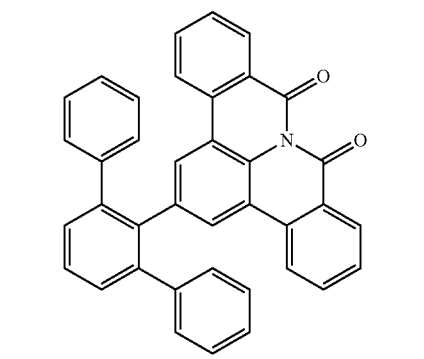 [SMILES: O=c1c2ccccc2c2cc(-c3c(-c4ccccc4)cccc3-c3ccccc3)cc3c4ccccc4c(=O)n1c23]
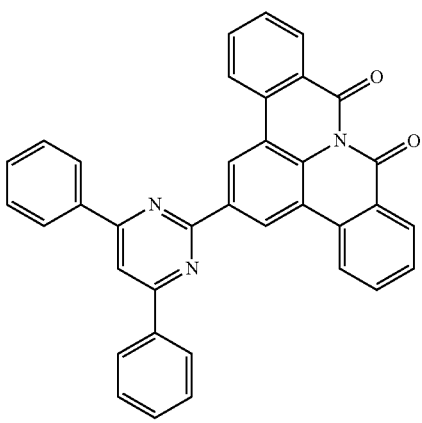
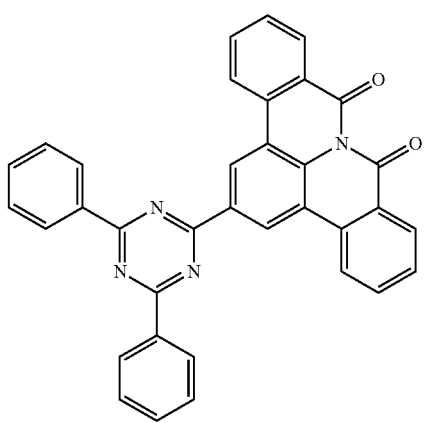 [SMILES: O=c1c2ccccc2c2cc(-c3nc(-c4ccccc4)nc(-c4ccccc4)n3)cc3c4ccccc4c(=O)n1c23]
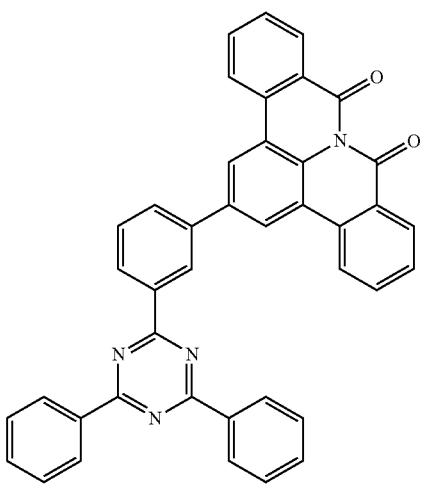 [SMILES: O=c1c2ccccc2c2cc(-c3cccc(-c4nc(-c5ccccc5)nc(-c5ccccc5)n4)c3)cc3c4ccccc4c(=O)n1c23]

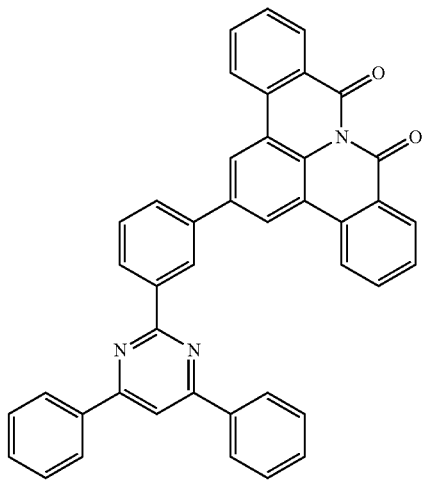 [SMILES: O=c1c2ccccc2c2cc(-c3cccc(-c4nc(-c5ccccc5)cc(-c5ccccc5)n4)c3)cc3c4ccccc4c(=O)n1c23]
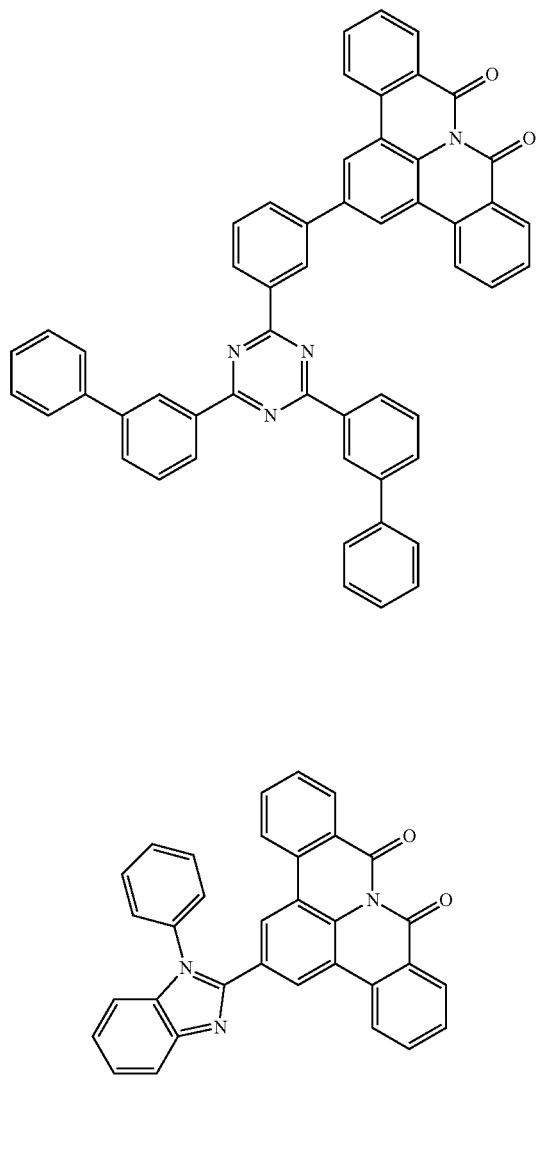
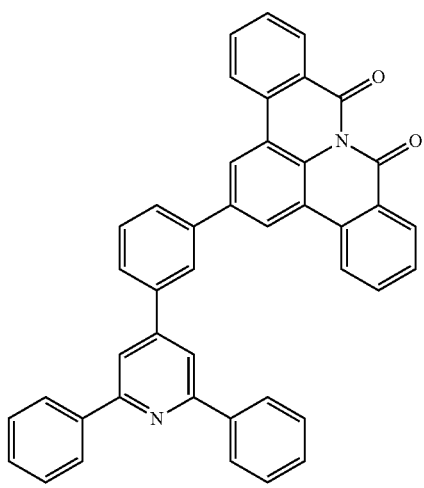 [SMILES: O=c1c2ccccc2c2cc(-c3cccc(-c4cc(-c5ccccc5)nc(-c5ccccc5)c4)c3)cc3c4ccccc4c(=O)n1c23]
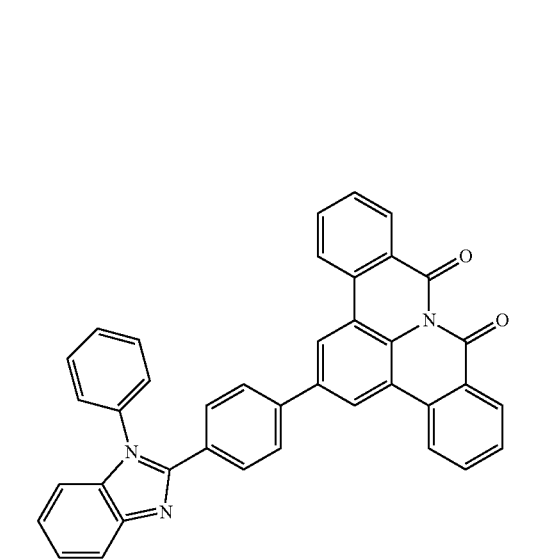
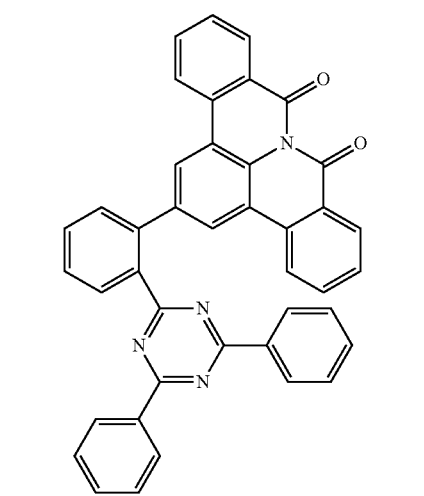 [SMILES: O=c1c2ccccc2c2cc(-c3ccccc3-c3nc(-c4ccccc4)nc(-c4ccccc4)n3)cc3c4ccccc4c(=O)n1c23]

-continued
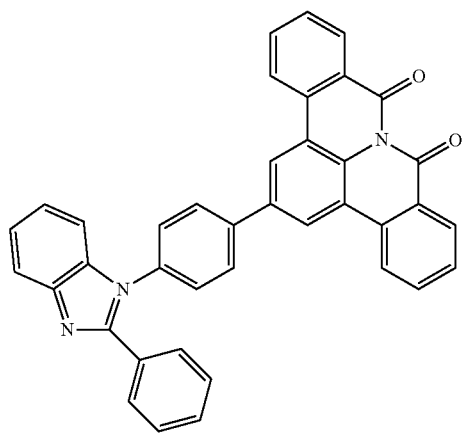
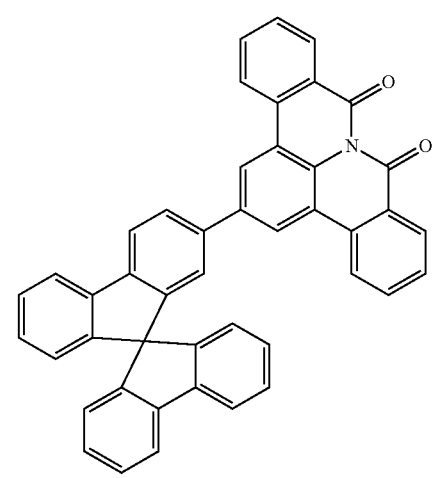 [SMILES: O=c1c2ccccc2c2cc(-c3ccc4c(c3)C3(c5ccccc5-c5ccccc53)c3ccccc3-4)cc3c4ccccc4c(=O)n1c23]
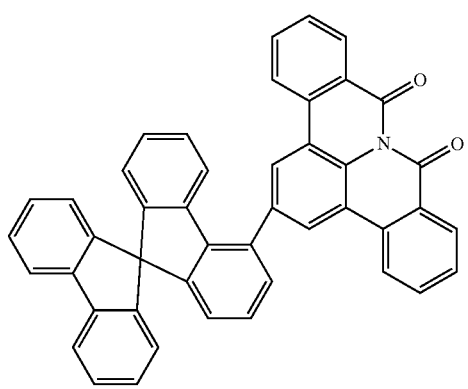 [SMILES: O=c1c2ccccc2c2cc(-c3cccc4c3-c3ccccc3C43c4ccccc4-c4ccccc43)cc3c4ccccc4c(=O)n1c23]
-continued
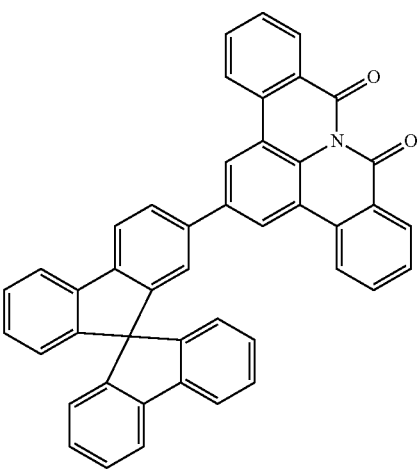 [SMILES: O=c1c2ccccc2c2cc(-c3ccc4c(c3)C3(c5ccccc5-c5ccccc53)c3ccccc3-4)cc3c4ccccc4c(=O)n1c23]
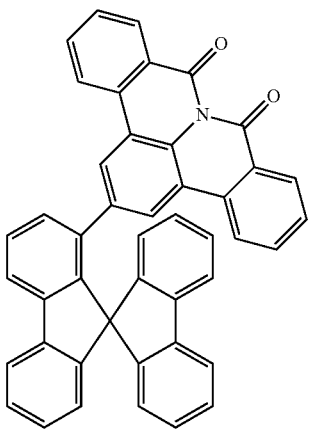 [SMILES: O=c1c2ccccc2c2cc(-c3cccc4c3C3(c5ccccc5-c5ccccc53)c3ccccc3-4)cc3c4ccccc4c(=O)n1c23]
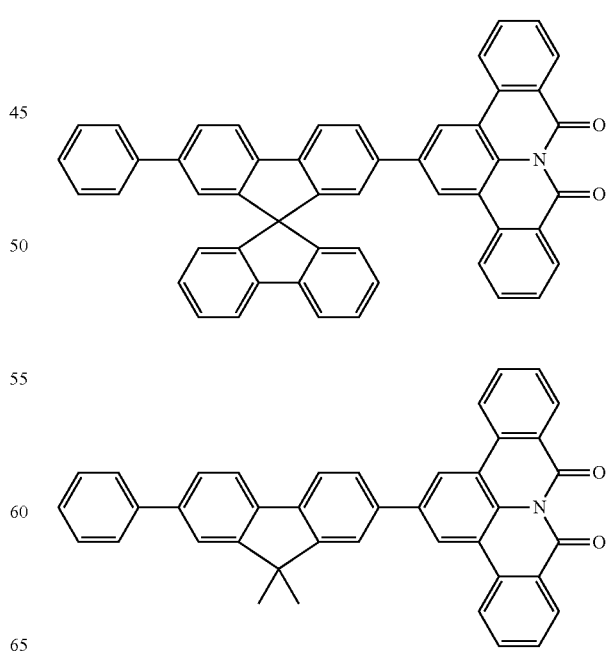

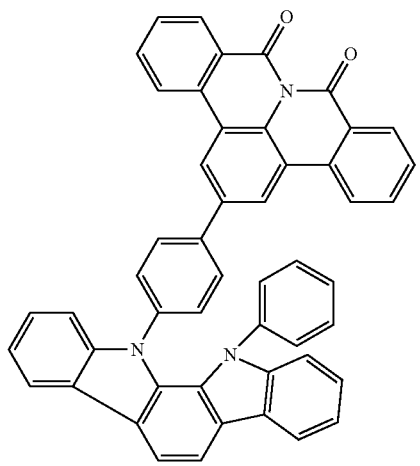 [SMILES: O=c1c2ccccc2c2cc(-c3ccc(-n4c5ccccc5c5ccc6c7ccccc7n(-c7ccccc7)c6c54)cc3)cc3c4ccccc4c(=O)n1c23]
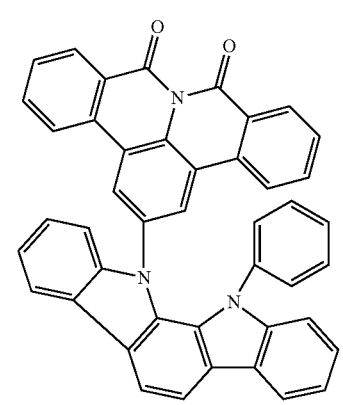 [SMILES: O=c1c2ccccc2c2cc(-n3c4ccccc4c4ccc5c6ccccc6n(-c6ccccc6)c5c43)cc3c4ccccc4c(=O)n1c23]
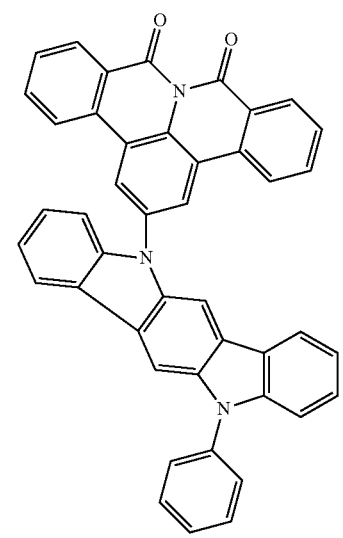 [SMILES: O=c1c2ccccc2c2cc(-n3c4ccccc4c4cc5c(cc43)c3ccccc3n5-c3ccccc3)cc3c4ccccc4c(=O)n1c23]
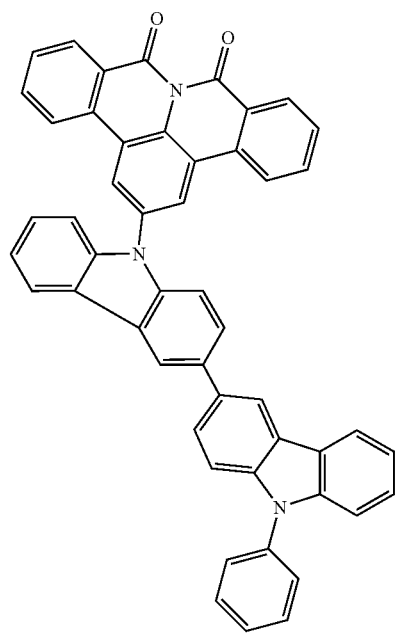 [SMILES: O=c1c2ccccc2c2cc(-n3c4ccccc4c4cc(-c5ccc6c(c5)c5ccccc5n6-c5ccccc5)ccc43)cc3c4ccccc4c(=O)n1c23]
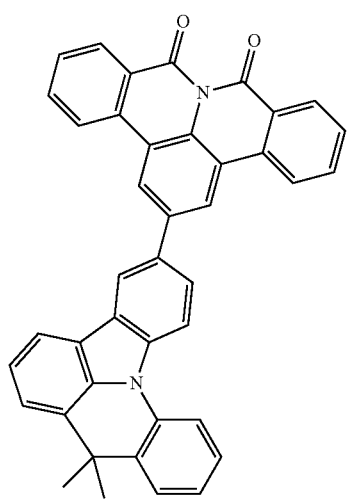 [SMILES: CC1(C)c2ccccc2-n2c3ccc(-c4cc5c6ccccc6c(=O)n6c(=O)c7ccccc7c(c4)c56)cc3c3cccc1c32]
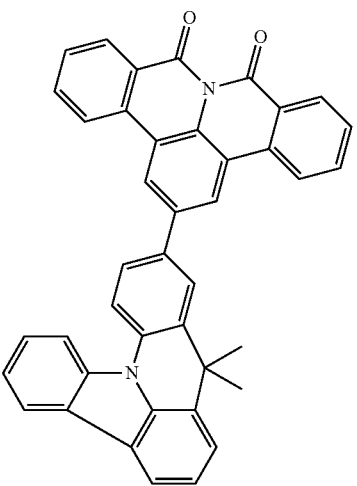 [SMILES: CC1(C)c2cc(-c3cc4c5ccccc5c(=O)n5c(=O)c6ccccc6c(c3)c45)ccc2-n2c3ccccc3c3cccc1c32]

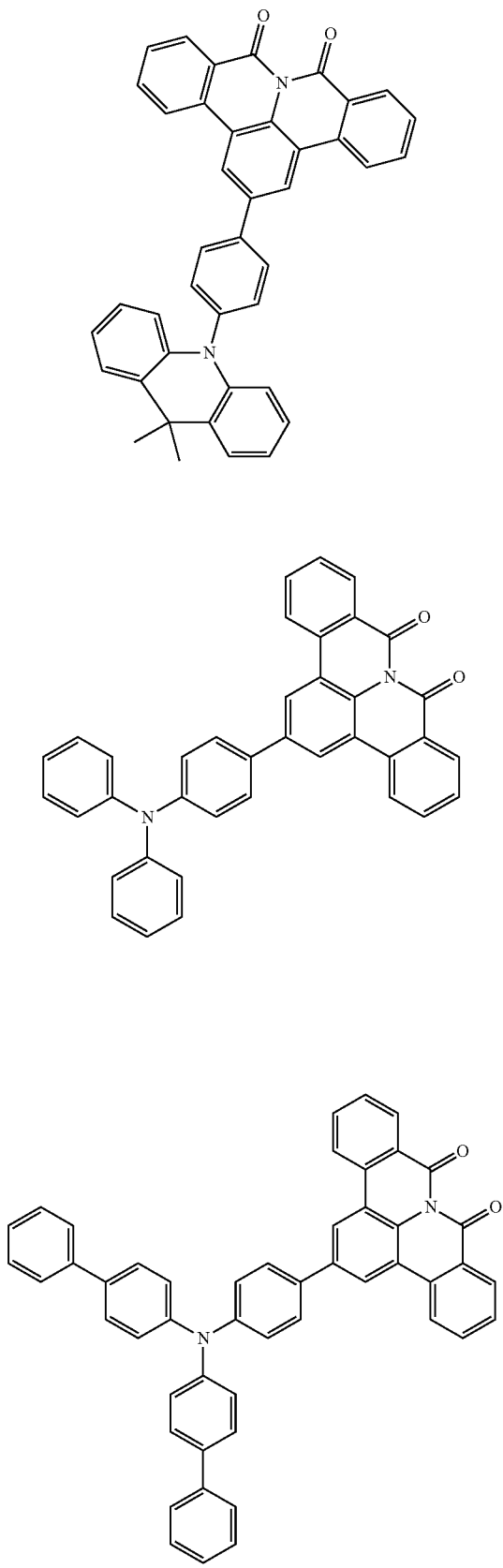
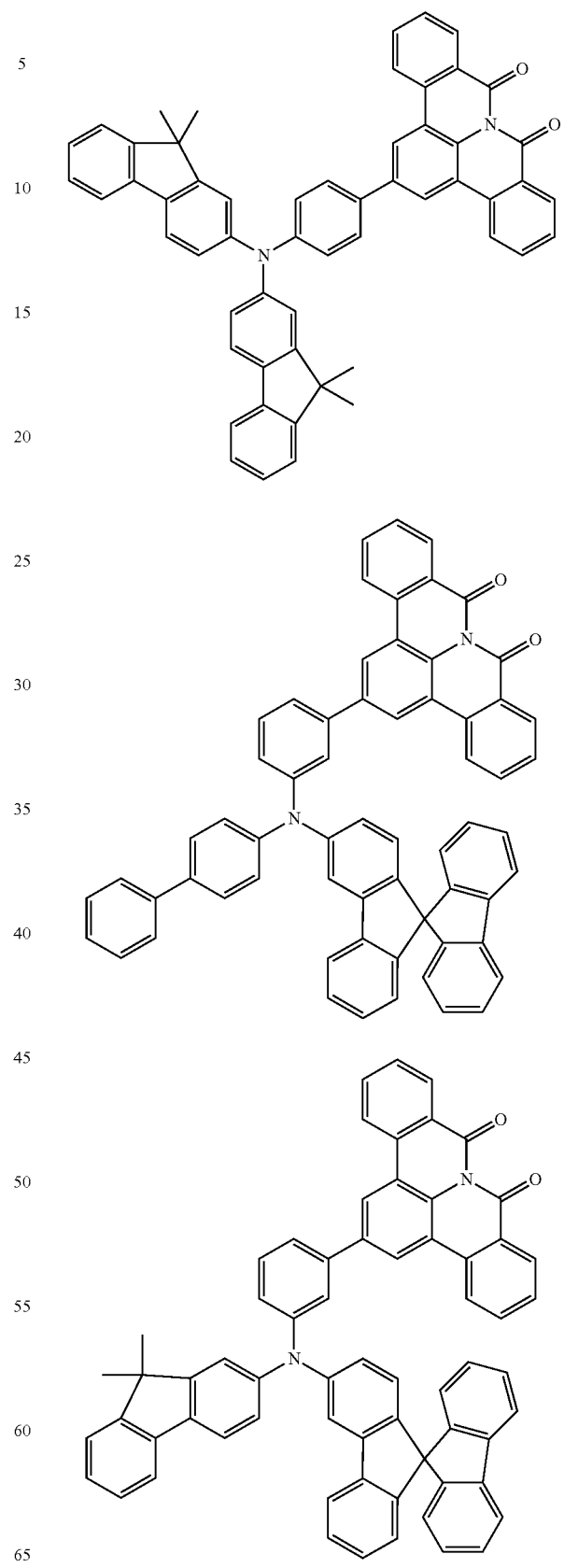

| 51 -continued | 52 -continued |
|---|---|
| 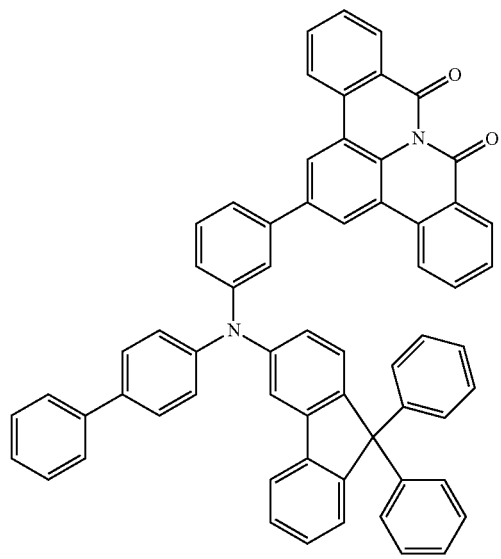 [SMILES: O=c1c2ccccc2c2cc(-c3cccc(N(c4ccc(-c5ccccc5)cc4)c4ccc5c(c4)-c4ccccc4C5(c4ccccc4)c4ccccc4)c3)cc3c4ccccc4c(=O)n1c23] | 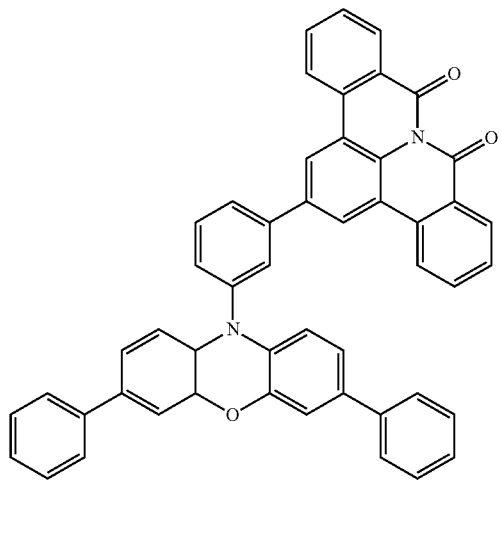 |
| 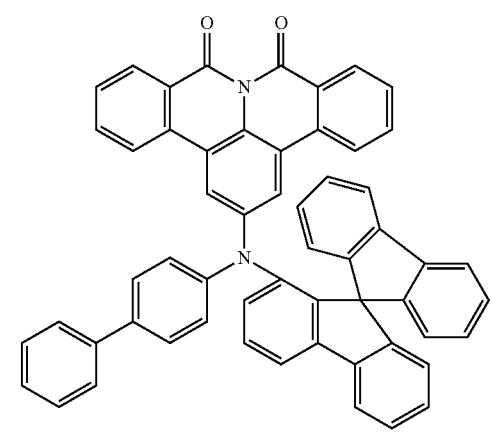 [SMILES: O=c1c2ccccc2c2cc(N(c3ccc(-c4ccccc4)cc3)c3cccc4c3C3(c5ccccc5-c5ccccc53)c3ccccc3-4)cc3c4ccccc4c(=O)n1c23] | 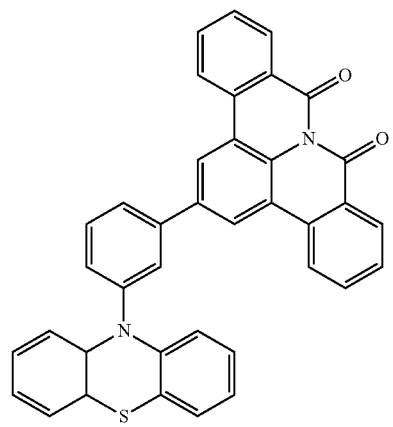 |
| 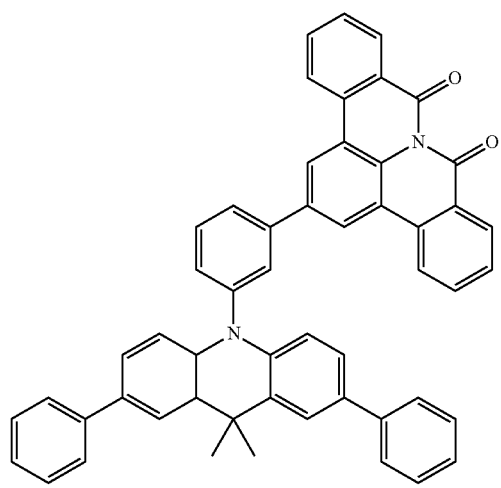 [SMILES: CC1(C)c2cc(-c3ccccc3)ccc2N(c2cccc(-c3cc4c5ccccc5c(=O)n5c(=O)c6ccccc6c(c3)c45)c2)C2C=CC(c3ccccc3)=CC21] | 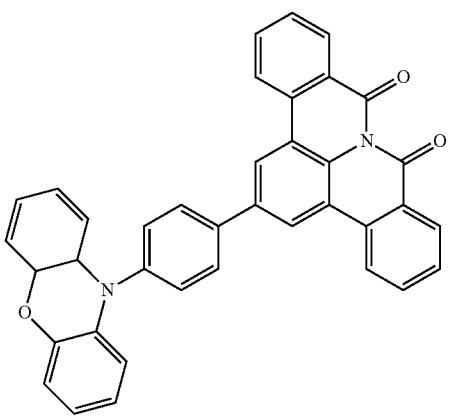 [SMILES: O=c1c2ccccc2c2cc(-c3ccc(N4c5ccccc5OC5C=CC=CC54)cc3)cc3c4ccccc4c(=O)n1c23] |

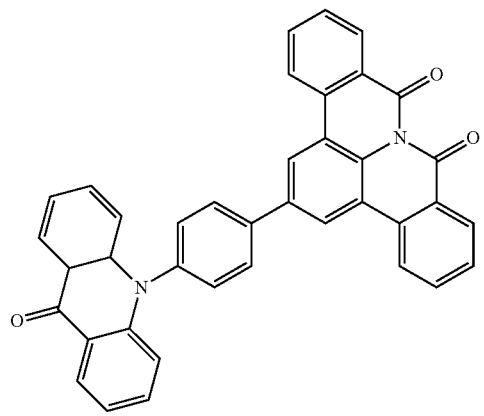 [SMILES: O=C1c2ccccc2N(c2ccc(-c3cc4c5ccccc5c(=O)n5c(=O)c6ccccc6c(c3)c45)cc2)C2C=CC=CC12]
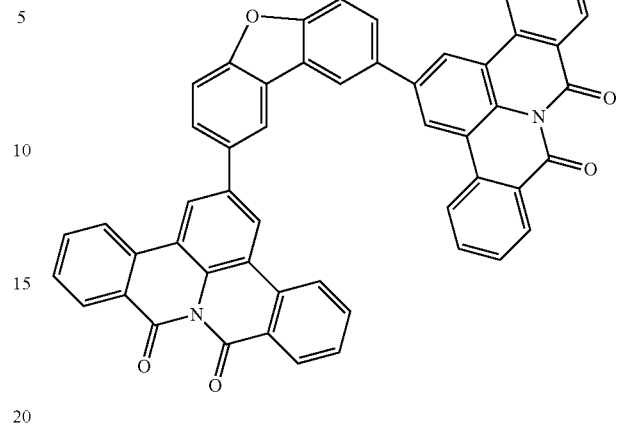
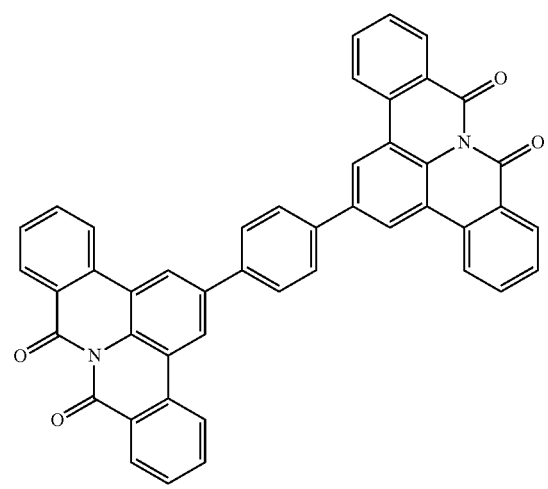 [SMILES: O=c1c2ccccc2c2cc(-c3ccc(-c4cc5c6ccccc6c(=O)n6c(=O)c7ccccc7c(c4)c56)cc3)cc3c4ccccc4c(=O)n1c23]
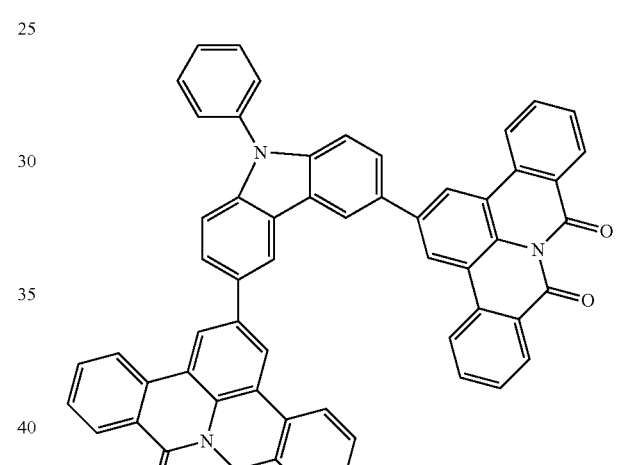
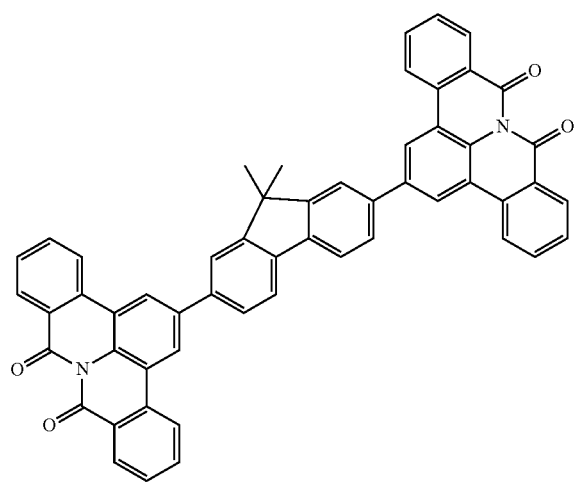 [SMILES: CC1(C)c2cc(-c3cc4c5ccccc5c(=O)n5c(=O)c6ccccc6c(c3)c45)ccc2-c2ccc(-c3cc4c5ccccc5c(=O)n5c(=O)c6ccccc6c(c3)c45)cc21]
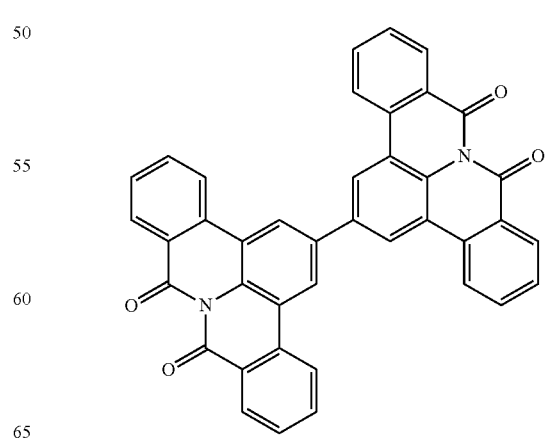

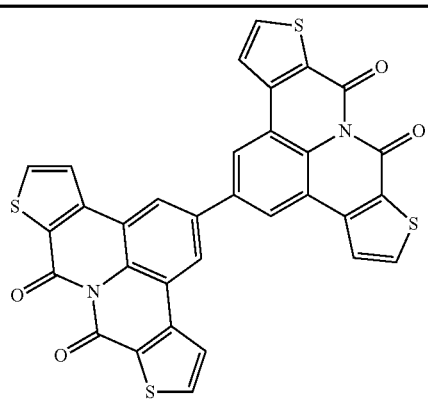
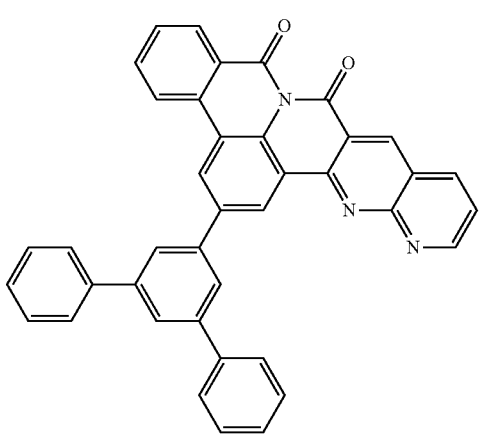
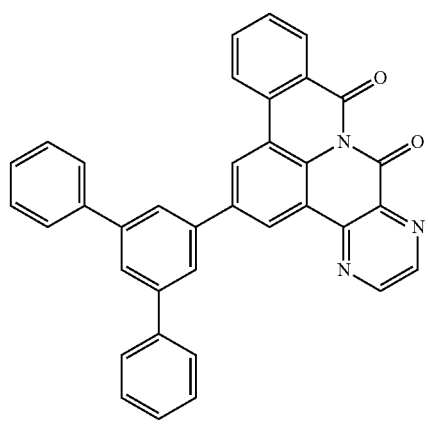 [SMILES: O=c1c2ccccc2c2cc(-c3cc(-c4ccccc4)cc(-c4ccccc4)c3)cc3c4nccnc4c(=O)n1c23]
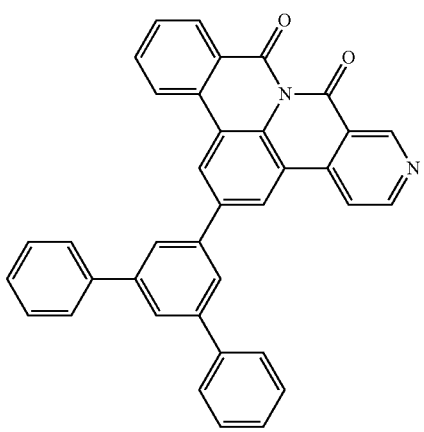
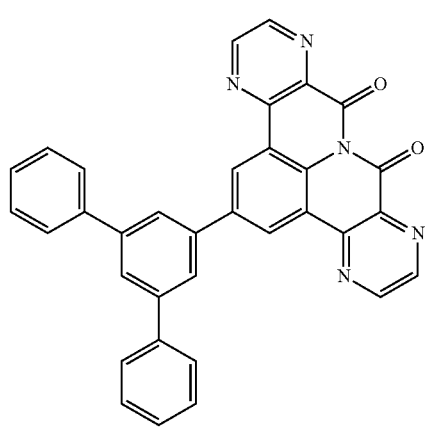 [SMILES: O=c1c2nccnc2c2cc(-c3cc(-c4ccccc4)cc(-c4ccccc4)c3)cc3c4nccnc4c(=O)n1c23]
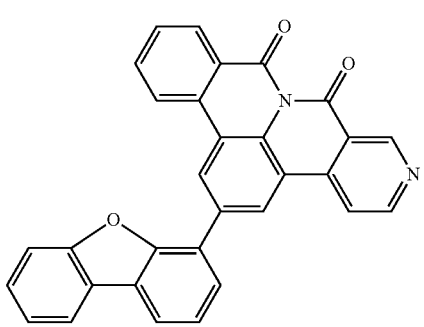
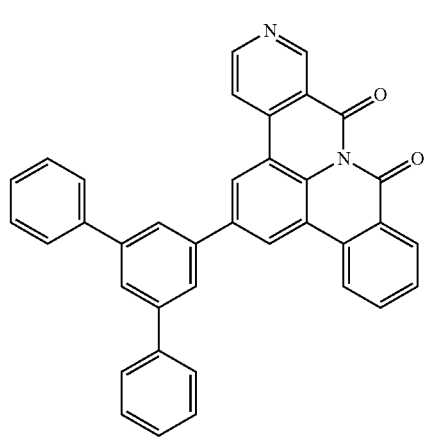 [SMILES: O=c1c2ccccc2c2cc(-c3cc(-c4ccccc4)cc(-c4ccccc4)c3)cc3c4ccncc4c(=O)n1c23]
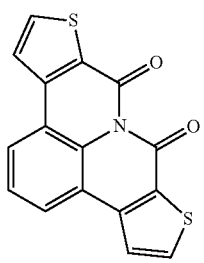 [SMILES: O=c1c2sccc2c2cccc3c4ccsc4c(=O)n1c23]

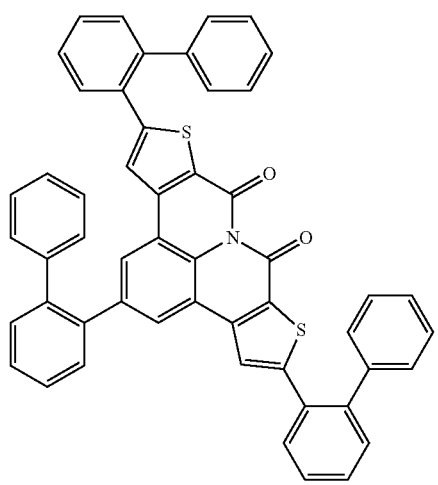 [SMILES: O=c1c2sc(-c3ccccc3-c3ccccc3)cc2c2cc(-c3ccccc3-c3ccccc3)cc3c4cc(-c5ccccc5-c5ccccc5)sc4c(=O)n1c23]
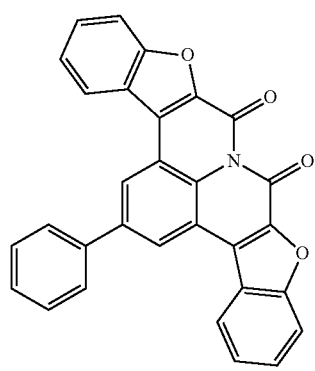 [SMILES: O=c1c2oc3ccccc3c2c2cc(-c3ccccc3)cc3c4c(oc5ccccc54)c(=O)n1c23]
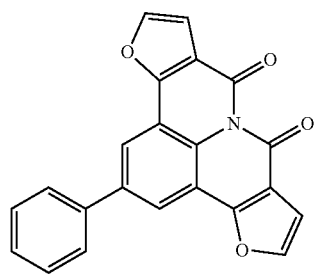 [SMILES: O=c1c2ccoc2c2cc(-c3ccccc3)cc3c4occc4c(=O)n1c23]
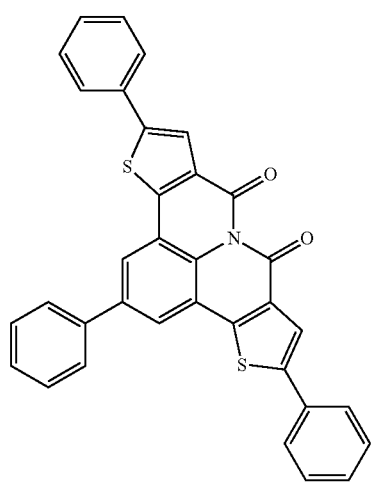 [SMILES: O=c1c2cc(-c3ccccc3)sc2c2cc(-c3ccccc3)cc3c4sc(-c5ccccc5)cc4c(=O)n1c23]
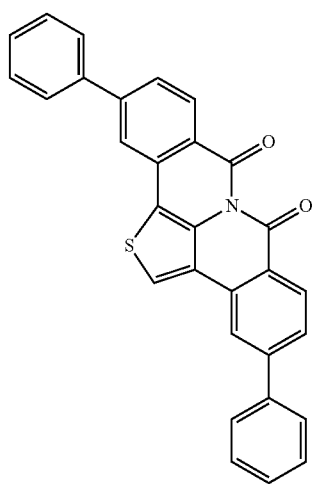 [SMILES: O=c1c2ccc(-c3ccccc3)cc2c2csc3c4cc(-c5ccccc5)ccc4c(=O)n1c23]
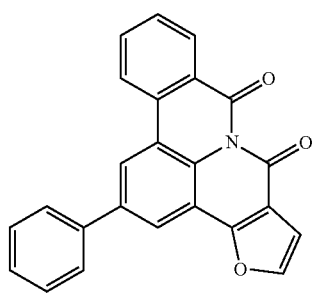 [SMILES: O=c1c2ccccc2c2cc(-c3ccccc3)cc3c4occc4c(=O)n1c23]
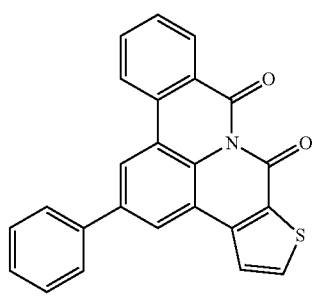 [SMILES: O=c1c2ccccc2c2cc(-c3ccccc3)cc3c4ccsc4c(=O)n1c23]
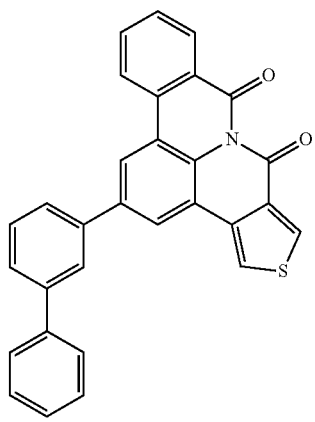 [SMILES: O=c1c2ccccc2c2cc(-c3cccc(-c4ccccc4)c3)cc3c4cscc4c(=O)n1c23]

-continued
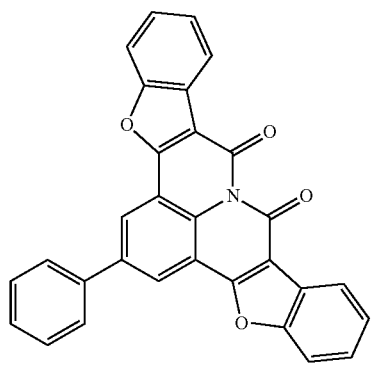 [SMILES: O=c1c2c3ccccc3oc2c2cc(-c3ccccc3)cc3c4oc5ccccc5c4c(=O)n1c23]
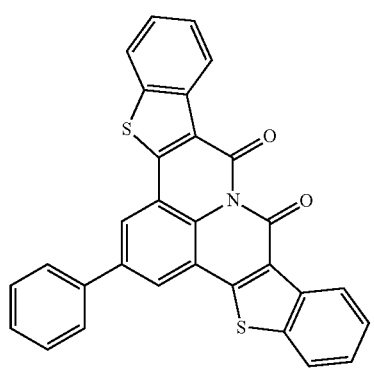 [SMILES: O=c1c2c3ccccc3sc2c2cc(-c3ccccc3)cc3c4sc5ccccc5c4c(=O)n1c23]
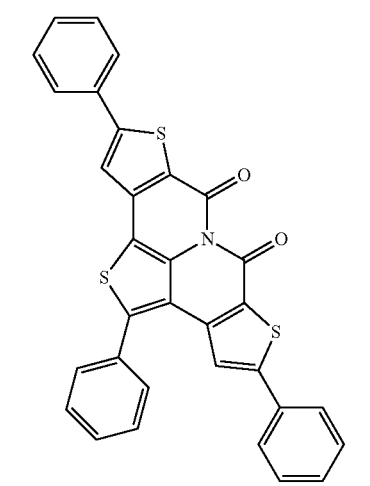 [SMILES: O=c1c2sc(-c3ccccc3)cc2c2sc(-c3ccccc3)c3c4cc(-c5ccccc5)sc4c(=O)n1c23]
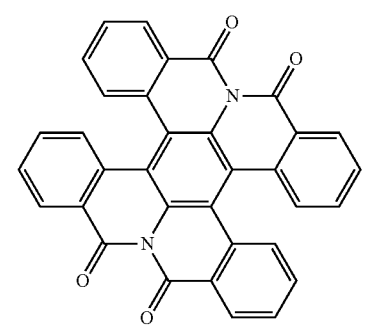 [SMILES: O=c1c2ccccc2c2c3c4ccccc4c(=O)n4c(=O)c5ccccc5c(c5c6ccccc6c(=O)n1c25)c34]
-continued
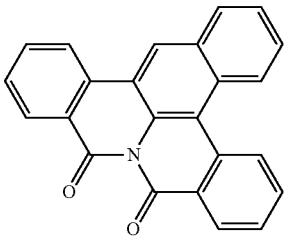 [SMILES: O=c1c2ccccc2c2cc3ccccc3c3c4ccccc4c(=O)n1c23]
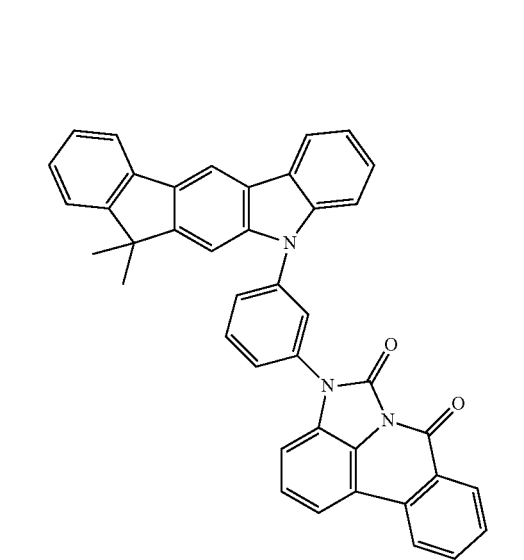 [SMILES: CC1(C)c2ccccc2-c2cc3c4ccccc4n(-c4cccc(-n5c(=O)n6c(=O)c7ccccc7c7cccc5c76)c4)c3cc21]

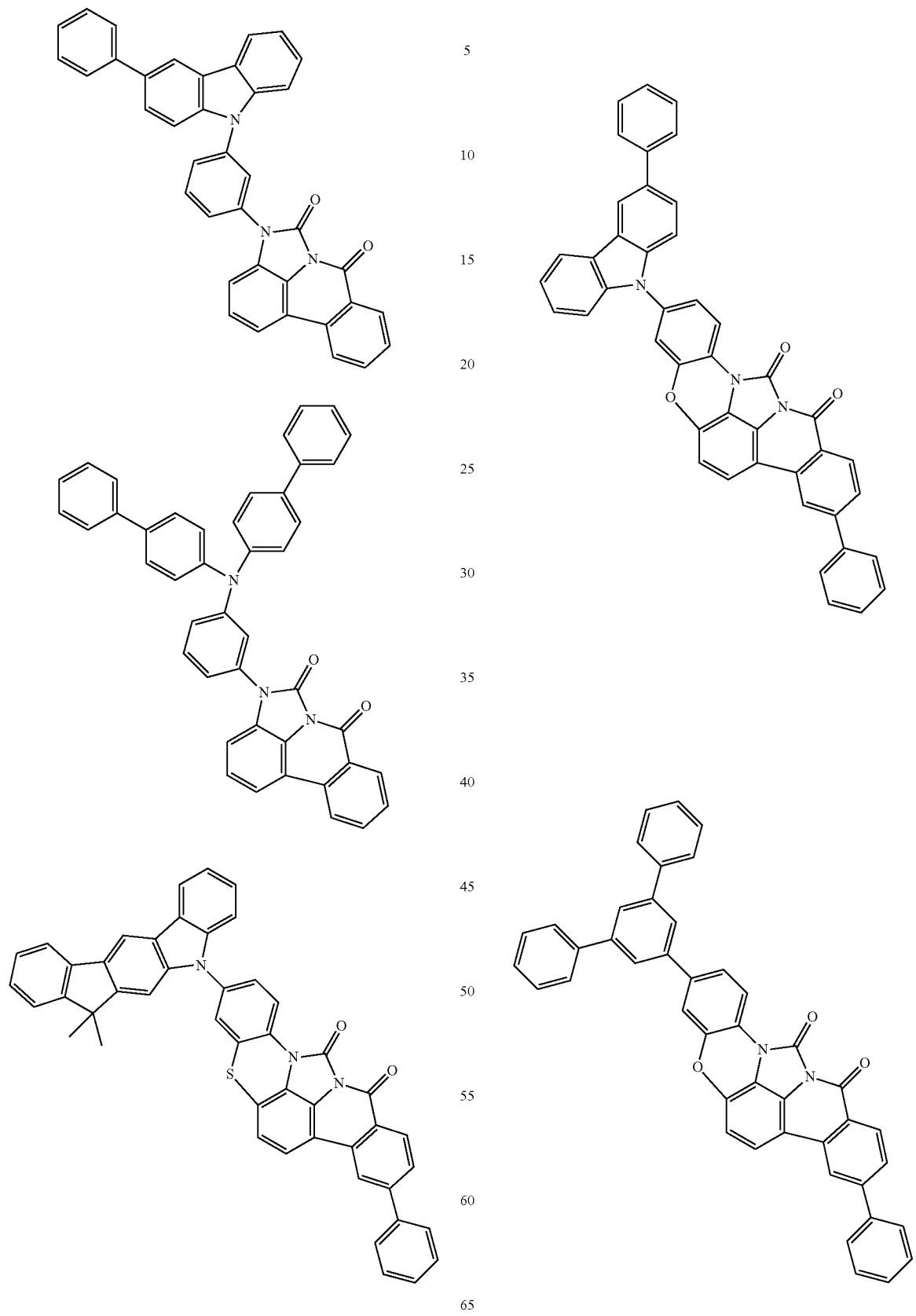

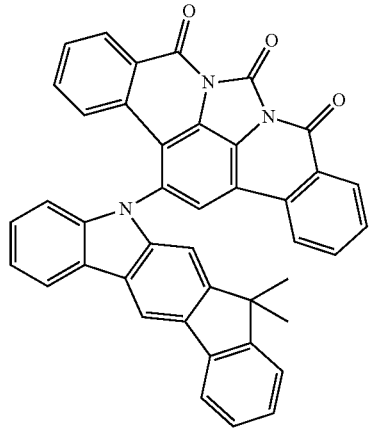 [SMILES: CC1(C)c2ccccc2-c2cc3c4ccccc4n(-c4cc5c6ccccc6c(=O)n6c(=O)n7c(=O)c8ccccc8c4c7c56)c3cc21]
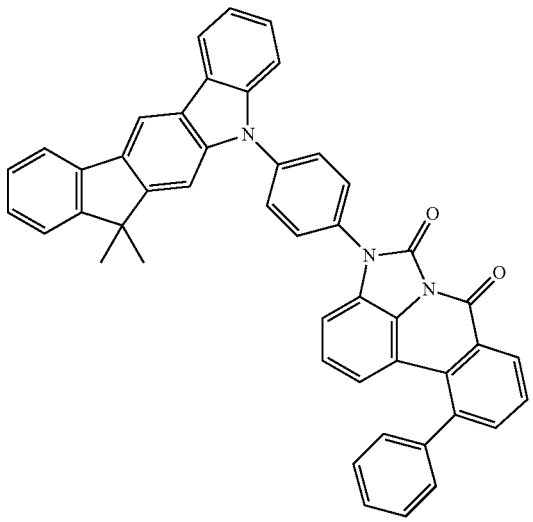
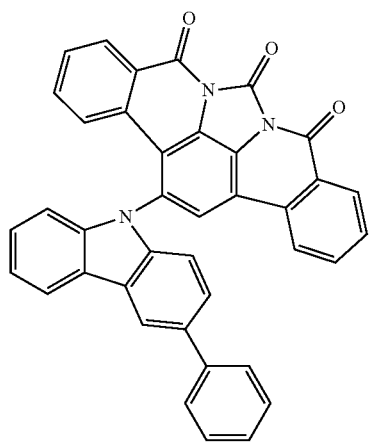 [SMILES: O=c1c2ccccc2c2cc(-n3c4ccccc4c4cc(-c5ccccc5)ccc43)c3c4ccccc4c(=O)n4c(=O)n1c2c34]
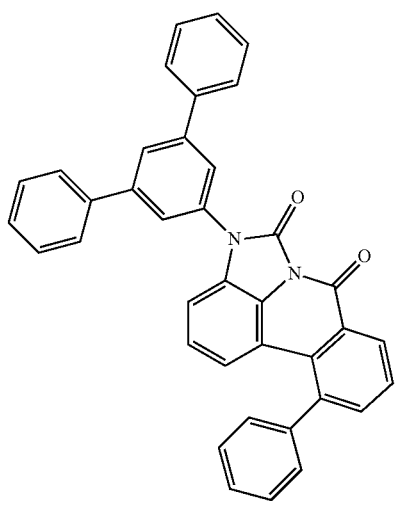
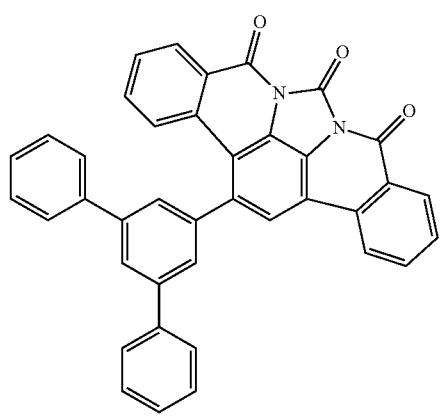 [SMILES: O=c1c2ccccc2c2cc(-c3cc(-c4ccccc4)cc(-c4ccccc4)c3)c3c4ccccc4c(=O)n4c(=O)n1c2c34]
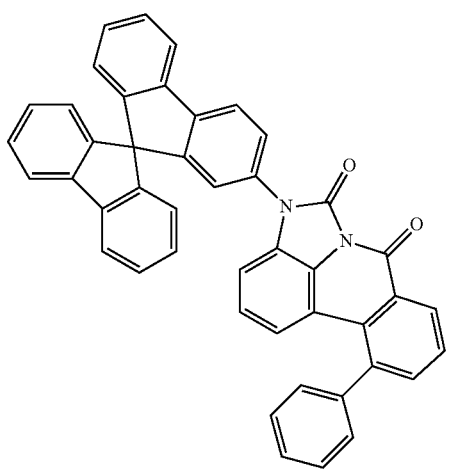 [SMILES: O=c1c2cccc(-c3ccccc3)c2c2cccc3c2n1c(=O)n3-c1ccc2c(c1)C1(c3ccccc3-c3ccccc31)c1ccccc1-2]

-continued

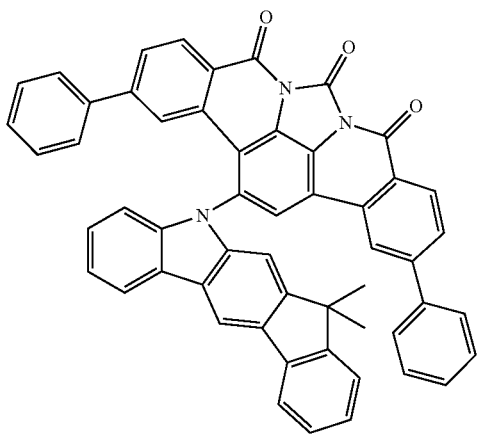 [SMILES: CC1(C)c2ccccc2-c2cc3c4ccccc4n(-c4cc5c6cc(-c7ccccc7)ccc6c(=O)n6c(=O)n7c(=O)c8ccc(-c9ccccc9)cc8c4c7c56)c3cc21]

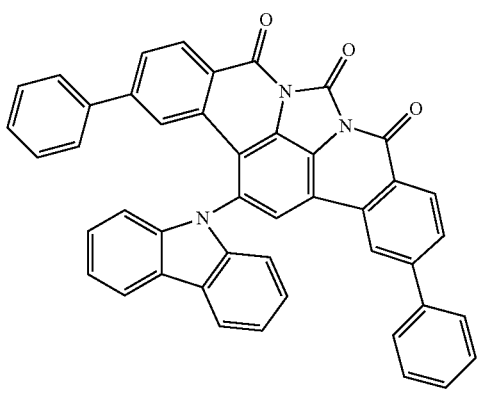 [SMILES: O=c1c2ccc(-c3ccccc3)cc2c2cc(-n3c4ccccc4c4ccccc43)c3c4cc(-c5ccccc5)ccc4c(=O)n4c(=O)n1c2c34]

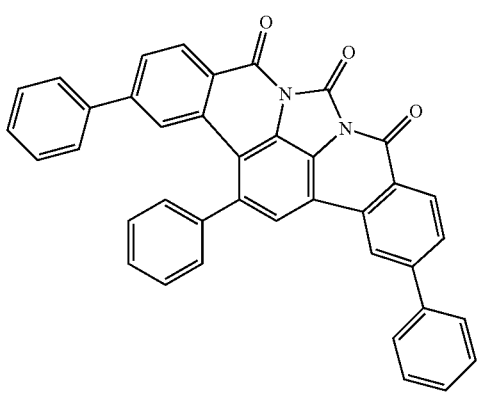 [SMILES: O=c1c2ccc(-c3ccccc3)cc2c2cc(-c3ccccc3)c3c4cc(-c5ccccc5)ccc4c(=O)n4c(=O)n1c2c34]

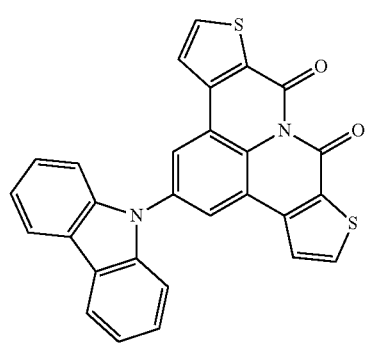 [SMILES: O=c1c2sccc2c2cc(-n3c4ccccc4c4ccccc43)cc3c4ccsc4c(=O)n1c23]

The compounds according to the invention can be prepared by synthesis steps known in principle to the person skilled in the art, as depicted diagrammatically in Scheme 1 and 2.

As depicted in Scheme 1, a Schmidt reaction and subsequent reduction gives the corresponding 5,6-dihydrophenanthridine derivative (a), which is converted into the 8a-azabenzo[fg]naphthacene-8,9-dione using ortho-halogen-substituted carboxylic acid halide and subsequent palladium-cata-lysed intramolecular cyclisation. This basic building block can be halogenated by halogenation, for example bromination using NBS. In a subsequent reaction, conversion can be carried out into the desired derivative using, for example, a Suzuki coupling, a Buchwald or Ullmann reaction.

Scheme 1:

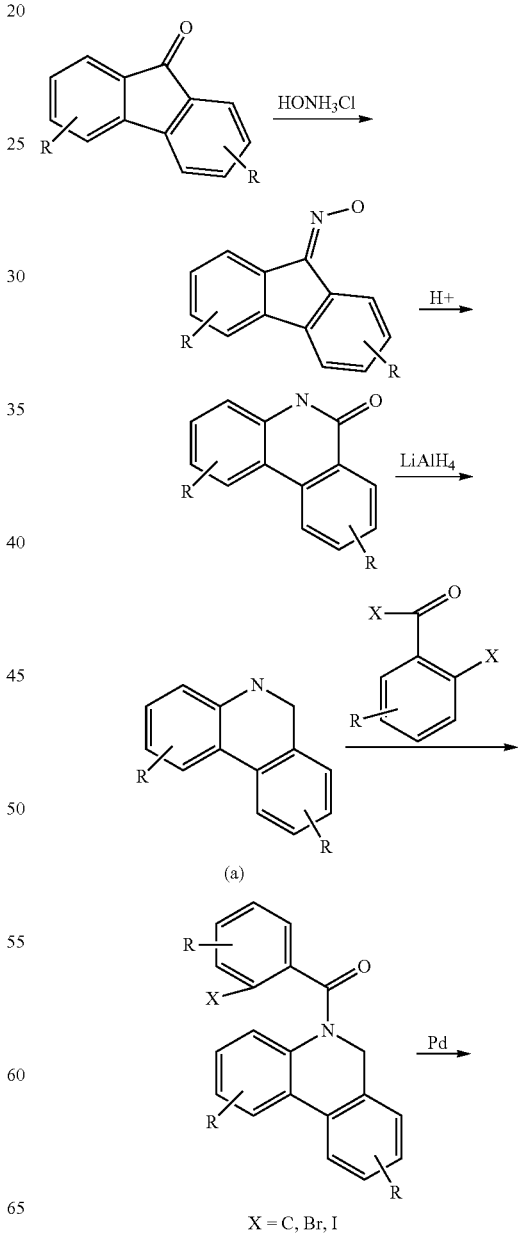

X = C, Br, I

67
-continued
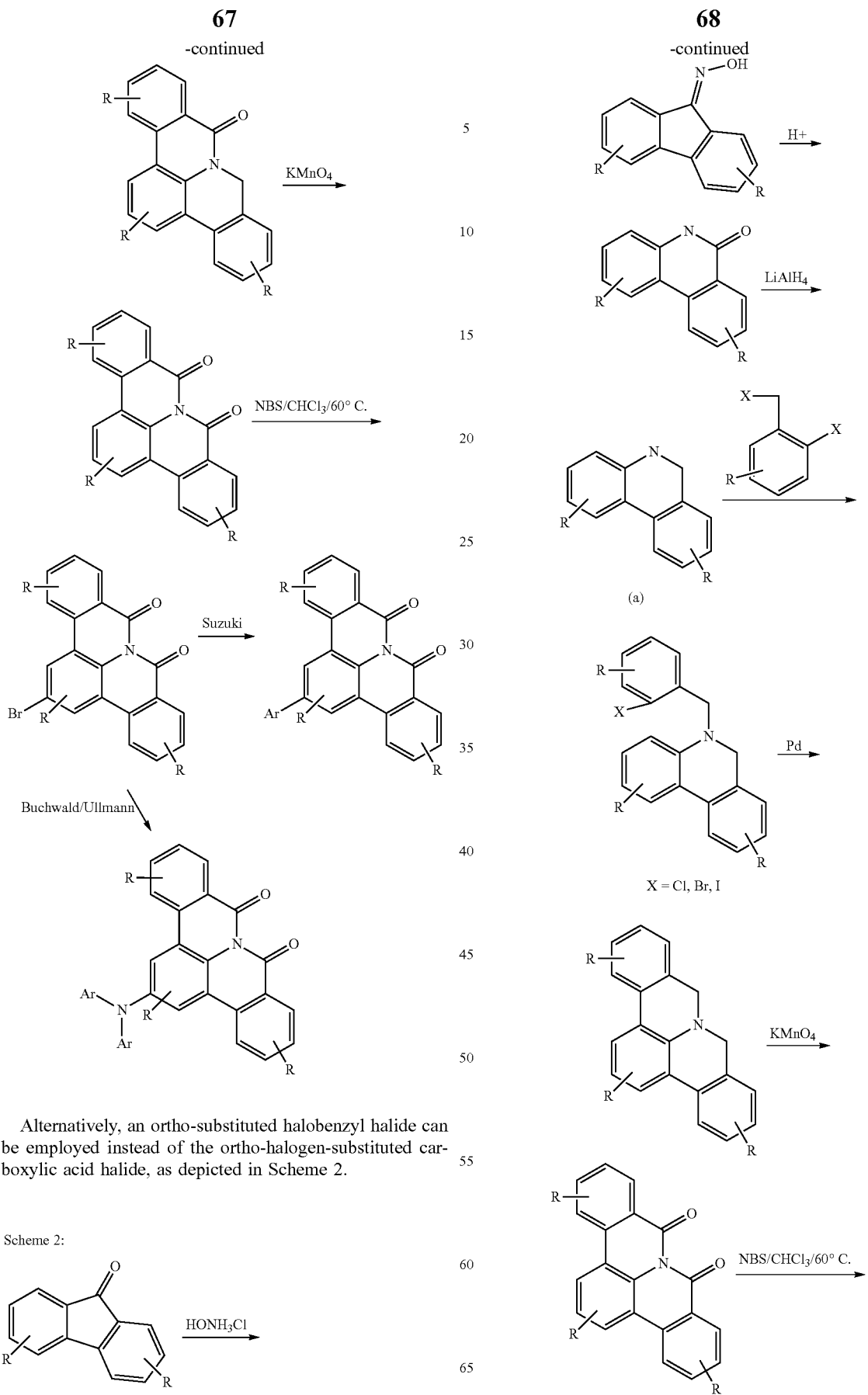
Alternatively, an ortho-substituted halobenzyl halide can be employed instead of the ortho-halogen-substituted carboxylic acid halide, as depicted in Scheme 2.
Scheme 2:

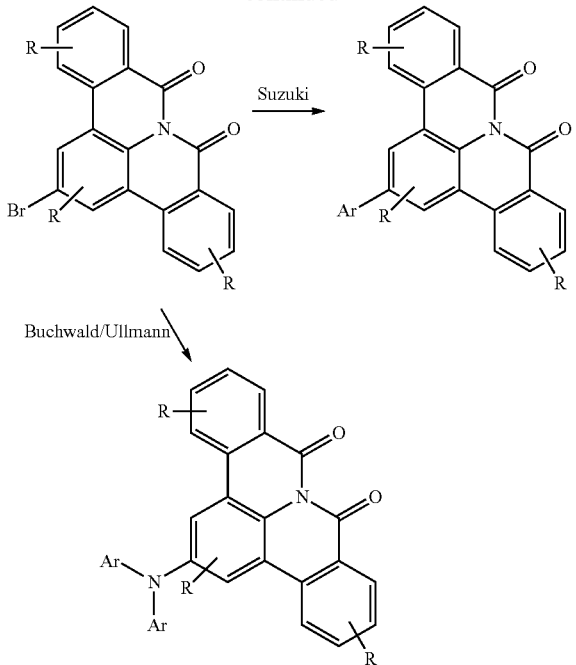

The present invention furthermore relates to a process for the preparation of a compound of the formula (1), comprising the steps:
a) preparation of the halogenated basic structure of the compound of the formula (1), where the halogen is preferably chlorine, bromine or iodine; and
b) introduction of at least one substituent R in the position of the halogen.

Processing of the compounds according to the invention from the liquid phase, for example by spin coating or by printing processes, requires formulations of the compounds according to the invention. These formulations can be, for example, solutions, dispersions or emulsions. It may be preferred to use mixtures of two or more solvents for this purpose. Suitable and preferred solvents are, for example, toluene, anisole, o-, m- or p-xylene, methyl-benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methyl-naphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclo-hexanol, cyclohexanone, cyclohexylbenzene, decalin, dodecylbenzene, ethyl benzoate, indane, methyl benzoate, NMP, p-cymene, phenetole, 1,4-di-isopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-di-methylphenyl)ethane or mixtures of these solvents.

The present invention therefore furthermore relates to a formulation comprising a compound according to the invention and at least one further compound. The further compound can be, for example, a solvent, in particular one of the above-mentioned solvents or a mixture of these solvents. However, the further compound may also be a further organic or inorganic compound which is likewise employed in the electronic device, for example an emitting compound, in particular a phosphorescent compound.

The present invention furthermore relates to the use of the compounds according to the invention in an electronic device, in particular in an organic electroluminescent device.

The organic electroluminescent devices and the light-emitting electrochemical cells can be employed for various applications, for example for monochrome or multicoloured displays, for lighting applications or for medical and/or cosmetic applications, for example in phototherapy.

An electronic device in the sense of the present invention is a device which comprises at least one layer which comprises at least one organic compound. The component here may also comprise inorganic materials or also layers which are built up entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitised solar cells (O-DSSC), organic optical detectors, organic photoreceptors, organic field-quench devices (O-FQDs), light-emitting electrochemical cells (LECs), organic laser diodes (O-lasers) and "organic plasmon emitting devices" (D. M. Koller et al., Nature Photonics 2008, 1-4), preferably organic electroluminescent devices (OLEDs) and particularly preferably phosphorescent OLEDs.

The organic electroluminescent device comprises cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. Interlayers, which have, for example, an exciton-blocking function, may likewise be introduced between two emitting layers. However, it should be pointed out that each of these layers does not necessarily have to be present. The organic electroluminescent device may comprise one emitting layer, or it may comprise a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). Furthermore, white emission can preferably be generated through the use of a blue emission layer and an emission layer which emits red and green, where these two emission layers may be separated from one another by a charge-generation layer.

The compound of the formula (1) can be employed in different layers here, depending on the precise structure. Preference is given to an organic electroluminescent device comprising a compound of the formula (1) or the above-mentioned preferred embodiments as matrix material for fluorescent or phosphorescent emitters, in particular for phosphorescent emitters, and/or in a hole-blocking layer and/or in an electron-transport layer and/or in an electron-blocking or exciton-blocking layer and/or in a hole-transport layer, depending on the precise substitution.

In a further embodiment of the invention, the organic electroluminescent device comprises the compound of the formula (1) or the above-mentioned preferred embodiments in an optical coupling-out layer. An optical coupling-out layer here is taken to mean a layer which is not located between the anode and the cathode, but instead is applied to an electrode outside the actual device, for example between an electrode and a substrate, in order to improve the optical coupling-out.

In a preferred embodiment of the invention, the compound according to the invention is employed as matrix material for a fluorescent or phosphorescent compound, in particular for a phosphorescent compound, in an emitting layer. The organic electroluminescent device here may comprise one emitting layer, or it may comprise a plurality of emitting layers, where at least one emitting layer comprises at least one compound of the formula (1) as matrix material.

If the compound of the formula (1) or the above-mentioned preferred embodiments is employed as matrix material for an emitting compound in an emitting layer, it is preferably employed in combination with one or more phosphorescent materials (triplet emitters). Phosphorescence in the sense of this invention is taken to mean the luminescence from an excited state having spin multiplicity>1, in particular from an excited triplet state. For the purposes of this application, all luminescent complexes with transition metals or lanthanides, in particular all iridium, platinum and copper complexes, are to be regarded as phosphorescent compounds.

The mixture of the compound of the formula (1) or the above-mentioned preferred embodiments and the emitting compound comprises between 99 and 1% by vol., preferably between 98 and 10% by vol., particularly preferably between 97 and 60% by vol., in particular between 95 and 80% by vol., of the compound of the formula (1) or the above-mentioned preferred embodiments, based on the entire mixture of emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the entire mixture of emitter and matrix material. Depending on the choice of matrix material, a lower emitter concentration may also be preferred, as described, for example, in the unpublished application EP 11002816.4.

A further preferred embodiment of the present invention is the use of the compound of the formula (1) or the above-mentioned preferred embodiments as matrix material for a phosphorescent emitter in combination with a further matrix material. A further preferred embodiment of the present invention is the use of the compound of the formula (1) or in accordance with the preferred embodiments as matrix material for a phosphorescent emitter in combination with a further matrix material. Particularly suitable matrix materials which can be employed in combination with the compounds of the formula (1) or in accordance with the preferred embodiments are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109, WO 2011/000455 or WO 2013/041176, azacarbazole derivatives, for example in accordance with EP 1617710, EP 1617711, EP 1731584, JP 2005/347160, bipolar matrix materials, for example in accordance with WO 2007/137725, silanes, for example in accordance with WO 005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with US 2009/0136779, WO 2010/050778, WO 2011/042107, WO 2011/088877 or WO 2012/143080, triphenylene derivatives, for example in accordance with WO 2012/048781, or lactams, for example in accordance with WO 2011/116865 or WO 2011/137951. A further phosphorescent emitter which emits at shorter wavelength than the actual emitter may likewise be present in the mixture as co-host.

Suitable as phosphorescent compound (=triplet emitter) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescence emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

Examples of the emitters described above are revealed by the applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as are used in accordance with the prior art for phosphorescent OLEDs and as are known to the person skilled in the art in the area of organic electroluminescence are suitable, and the person skilled in the art will be able to use further phosphorescent complexes without inventive step.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer as hole-transport or hole-injection material directly adjacent to the emitting layer, as described, for example, in WO 2009/030981.

In a further preferred embodiment of the invention, the compound of the formula (1) or the above-mentioned preferred embodiments is employed as electron-transport material in an electron-transport or electron-injection layer.

The emitting layer here may be fluorescent or phosphorescent. If the compound is employed as electron-transport material, it may be preferred for it to be doped, for example with alkali-metal complexes, such as, for example, LiQ (lithium hydroxyquinolinate).

In still a further preferred embodiment of the invention, the compound of the formula (1) or the above-mentioned preferred embodiments is employed in a hole-blocking layer. A hole-blocking layer is taken to mean a layer which is directly adjacent to an emitting layer on the cathode side.

It is furthermore possible to use the compound of the formula (1) or the above-mentioned preferred embodiments both in a hole-blocking layer or electron-transport layer and also as matrix in an emitting layer.

In still a further embodiment of the invention, the compound of the formula (1) or the above-mentioned preferred embodiments is employed in a hole-transport layer or in an electron-blocking layer or exciton-blocking layer.

In the further layers of the organic electroluminescent device according to the invention, all materials as are usually employed in accordance with the prior art can be used. The person skilled in the art will therefore be able, without inventive step, to employ all materials known for organic electroluminescent devices in combination with the compounds of the formula (1) according to the invention or the above-mentioned preferred embodiments.

Preference is furthermore given to an organic electroluminescent device, characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing, LITI (light induced thermal imaging, thermal transfer printing), ink-jet printing or nozzle printing. Soluble compounds, which are obtained, for example, by suitable substitution, are necessary for this purpose. These processes are also suitable, in particular, for oligomers, dendrimers and polymers.

Also possible are hybrid processes, in which, for example, one or more layers are applied from solution and one or more further layers are applied by vapour deposition.

These processes are generally known to the person skilled in the art and can be applied by him without inventive step to organic electroluminescent devices comprising the compounds according to the invention.

The compounds according to the invention and the organic electroluminescent devices according to the invention are distinguished by one or more of the following surprising advantages over the prior art:
1. The compounds according to the invention, employed as matrix material for fluorescent or phosphorescent emitters, result in very high efficiencies and in long lifetimes. This applies, in particular, if the compounds are employed as matrix material for a red- or green-phosphorescent emitter.
2. The compounds according to the invention have high thermal stability.
3. The compounds according to the invention, employed in organic electroluminescent devices, result in high efficiencies and in steep current/voltage curves with low use voltages.
4. Also when used as electron-transport material, the compounds according to the invention result in very good properties in relation to the efficiency, the lifetime and the operating voltage of organic electroluminescent devices.

These above-mentioned advantages are not accompanied by an impairment of the other electronic properties.

The invention is explained in greater detail by the following examples without wishing to restrict it thereby. The person skilled in the art will be able to carry out the invention throughout the range disclosed on the basis of the descriptions and prepare further compounds according to the invention without inventive step and use them in electronic devices or use the process according to the invention.

EXAMPLES

The following syntheses are carried out, unless indicated otherwise, under a protective-gas atmosphere. The starting materials can be purchased from ALDRICH or ABCR (palladium(II) acetate, tri-o-tolylphosphine, inorganics, solvents). The numbers in the case of the literature-known starting materials are the CAS numbers.

Example 1: 5,6-Dihydrophenanthridine

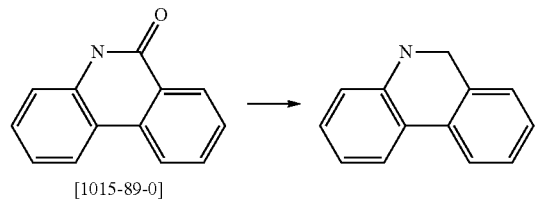 [SMILES: O=c1[nH]c2ccccc2c2ccccc12 ; c1ccc2c(c1)CNc1ccccc1-2]

[1015-89-0]

8.78 g (153 mmol) of LiAlH$_4$ are initially introduced in 1000 ml of THF under protective-gas atmosphere. 30 g (153 mmol) of 5H-phenanthridin-6-one are added in portions and subsequently heated under reflux for 8 h. The solvent is removed in vacuo and employed further without further application. The yield is 27 g (97%).

The following compounds are obtained analogously:

| Ex. | Starting material 1 | Product | Yield |
|---|---|---|---|
| 1a | [1350243-25-2] | | 73% |
| 1b | [630422-69-4] | | 70% |
| 1c | [420849-22-5] | | 75% |

Example 2:
15-(2-Iodobenzoyl)-5H-phenanthridin-6-one

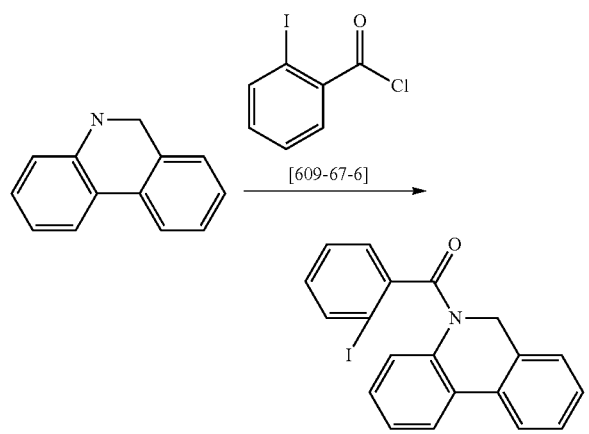

[609-67-6]

20 g (113 mmol) of 5,6-dihydrophenanthridine are dissolved in 500 ml of THF under protective-gas atmosphere and cooled to −25° C. 49.9 g (113 mmol) of 2-iodobenzoyl chloride are dissolved in 300 ml of THF and added dropwise to the reaction mixture at such a rate that the temperature does not exceed −25° C. After 1 h at −25° C., the mixture is allowed to come slowly to room temperature and is then stirred at room temperature for 1 h. After this time, the reaction mixture is poured onto ice and extracted three times with ethyl acetate. The combined organic phases are dried over Na$_2$SO$_4$ and evaporated. The residue is recrystallised from n-heptane. The yield is 40 g (90%).

The following compounds are obtained analogously:

| Ex. | Starting material 1 | Starting material 2 | Product | Yield |
|---|---|---|---|---|
| 2a | [1122399-53-4] | [609-67-6] | | 76% |
| 2b | [928307-79-3] | [609-67-6] | | 87% |
| 2c | [342404-76-6] | [609-67-6] | | 91% |
| 2d | [61686-63-3] | [609-67-6] | | 90% |

| Ex. | Starting material 1 | Starting material 2 | Product | Yield |
|---|---|---|---|---|
| 2e | | [1261446-07-4] | | 87% |
| 2f | | [1367346-08-4] | | 78% |
| 2g | | [75427-00-8] | | 76% |
| 2h | | [75427-00-8] | | 77% |
| 2j | | [609-67-6] | | 73% |

Example 3:
5-(2-Bromobenzyl)-5,6-dihydrophenanthridine

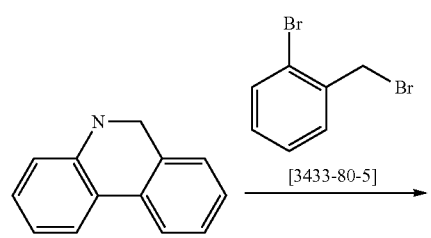

[3433-80-5]

-continued

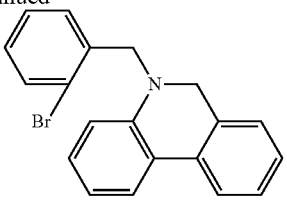

9.7 g (243 mmol) of 60% NaH in mineral oil are dissolved in 500 ml of dimethylformamide under protective-gas atmosphere. 43.9 g (243 mmol) of 5,6-dihydrophenanthridine are dissolved in 500 ml of DMF and added dropwise to the reaction mixture. After 1 h at room temperature, a solution of 60.6 g (242 mmol) of 2-bromobenzyl bromide in 500 ml of DMF is added dropwise. The reaction mixture is then stirred at room temperature for 1 h. After this time, the reaction mixture is poured onto ice and extracted three times with dichloromethane. The combined organic phases are dried over Na$_2$SO$_4$ and evaporated. The residue is extracted with hot toluene and recrystallised from toluene/n-heptane. The yield is 62 g (75%).

The following compounds are obtained analogously:

| Ex. | Starting material 1 | Starting material 2 | Product | Yield |
|---|---|---|---|---|
| 3a | 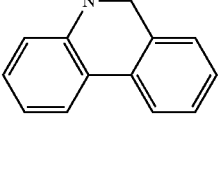 | 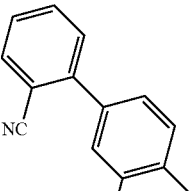 [135689-85-9] | 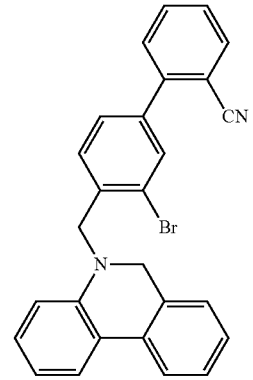 [SMILES: N#Cc1ccccc1-c1ccc(CN2Cc3ccccc3-c3ccccc32)c(Br)c1] | 83% |
| 3b | 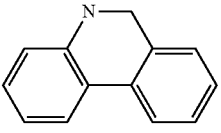 [SMILES: c1ccc2c(c1)CNc1ccccc1-2] | 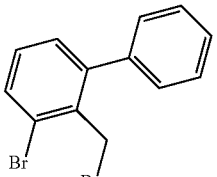 [172976-02-2] | 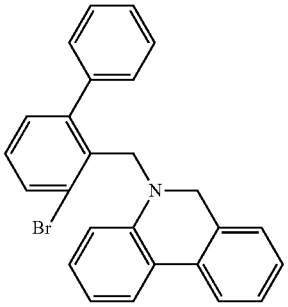 [SMILES: Brc1cccc(-c2ccccc2)c1CN1Cc2ccccc2-c2ccccc21] | 90% |
| 3c | 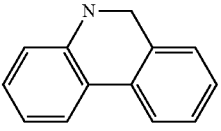 [SMILES: c1ccc2c(c1)CNc1ccccc1-2] | 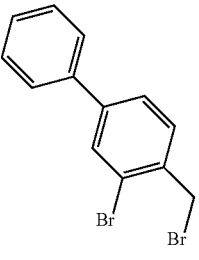 [1396865-04-5] | 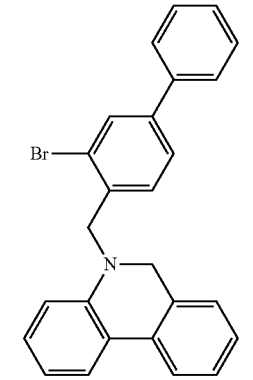 [SMILES: Brc1cc(-c2ccccc2)ccc1CN1Cc2ccccc2-c2ccccc21] | 95% |

Example 4: 8a-Azabenzo[fg]naphthacene-8,9-dione

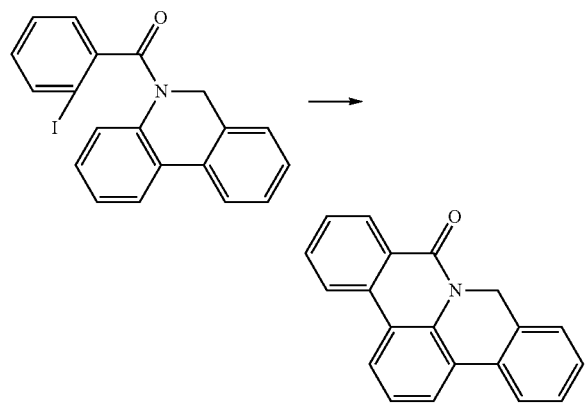

35 g (158 mmol) of 5-(2-bromobenzyl)-5H-phenanthridin-6-one are dissolved in 1000 ml of dimethylformamide under protective-gas atmosphere. 75.7 g (234 mmol) of tetrabutylammonium bromide, 2.15 g (9.5 mmol) of palladium acetate and 10 g (102 mmol) of potassium acetate are added to this solution. The mixture is subsequently stirred at 130° C. for 2 h. After this time, the reaction mixture is cooled to room temperature. The residue is filtered off with suction and washed with EtOH. The residue is recrystallised from n-heptane/toluene. The yield is 17.7 g (74%).

The following compounds are obtained analogously:

| Ex. | Starting material 1 | Product | Yield |
|---|---|---|---|
| 4a | | | 80% |
| 4b | | | 83% |
| 4c | | | 67% |
| 4d | | | 73% |

| Ex. | Starting material 1 | Product | Yield |
|---|---|---|---|
| 4e | | | 79% |
| 4f | | | 82% |
| 4g | | | 77% |
| 4h | | | 78% |
| 4j | | | 73% |
Example 5: 8H,9H-8a-Azabenzo[fg]naphthacene
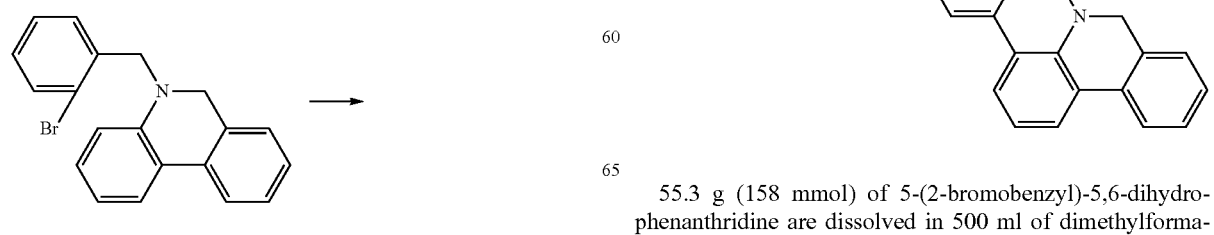
55.3 g (158 mmol) of 5-(2-bromobenzyl)-5,6-dihydrophenanthridine are dissolved in 500 ml of dimethylformamide under protective-gas atmosphere. 17.3 g (75 mmol) of benzyltrimethylammonium bromide and 31.28 g (226 mmol) of potassium carbonate are added to this solution. 5.08 g (22 mmol) of Pd(OAC)₂ is subsequently added under protective gas, and the mixture is stirred at 120° C. for 9 h.

After this time, the reaction mixture is cooled to room temperature and extracted with dichloromethane. The combined organic phases are dried over Na₂SO₄ and evaporated. The residue is recrystallised from n-heptane. The yield is 34 g (81%).

| Ex. | Starting material 1 | Product | Yield |
|---|---|---|---|
| 5a | | | 82% |
| 5b | | | 80% |
| 5c | | | 74% |

Example 6: 8a-Azabenzo[fg]naphthacene-8,9-dione

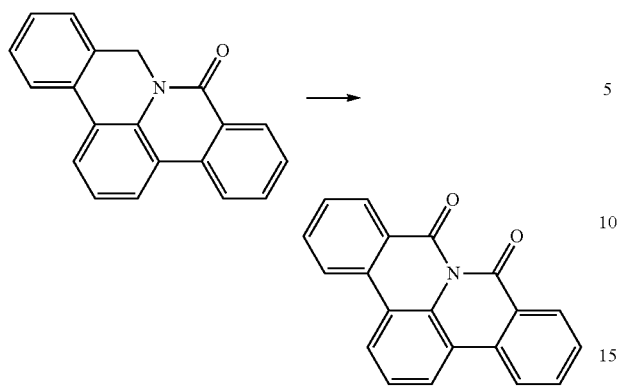

32 g (115 mmol) of 9H-8a-azabenzo[fg]naphthacen-8-one are dissolved in 1500 ml of acetone. 54.7 g (346 mmol) of potassium permanganate are added to this solution in portions and stirred at room temperature for two days. After this time, the remaining potassium permanganate is filtered off, the solution is evaporated and purified by chromatography (eluent:heptane/dichloromethane, 5:1). The residue is recrystallised from n-heptane. The yield is 24 g (73%).

The following compounds are obtained analogously:

| Ex. | Starting material 1 | Product | Yield |
|---|---|---|---|
| 6a |  |  | 60% |
| 6b |  |  | 69% |
| 6c |  |  | 71% |
| 6d |  |  | 65% |

| Ex. | Starting material 1 | Product | Yield |
|---|---|---|---|
| 6e | | | 72% |
| 6f | | | 77% |
| 6g | | | 62% |
| 6h | | | 65% |
| 6j | | | 64% |

The following compounds are obtained analogously using 6 eq. of KMnO₄:

| Ex. | Starting material 1 | Product | Yield |
|---|---|---|---|
| 6i | | | 83% |

| Ex. | Starting material 1 | Product | Yield |
|---|---|---|---|
| 6k | | | 86% |
| 6l | | | 79% |
| 6m | | | 70% |

Example 7:
2-Bromo-8a-azabenzo[fg]naphthacene-8,9-dione

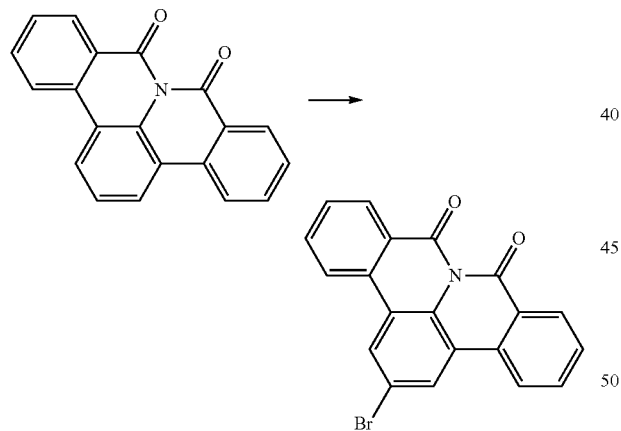

18.6 g (62.5 mmol) of 8a-azabenzo[fg]naphthacene-8,9-dione are initially introduced in 1800 ml of $CH_2Cl_2$. 25.6 (312 mmol) of sodium acetate and 24.9 g (156 mmol) of bromine are subsequently added to the reaction mixture, and the mixture is stirred at 80° C. for 30 h. 150 ml of water and 60 g of NaOH pellets are subsequently added to the mixture, and the solid which precipitates out is filtered off with suction. The product is washed with EtOH and dried. Yield: 19 g (51 mmol), 81% of theory, purity according to $^1$H-NMR about 96%.

The following compounds are obtained analogously:

| Ex. | Starting material 1 | Product | Yield |
|---|---|---|---|
| 7a | | | 83% |

| Ex. | Starting material 1 | Product | Yield |
|---|---|---|---|
| 7b | | | 82% |
| 7c | | | 80% |
| 7d | | | 78% |
| 7e | | | 34% |
| 7f | | | 50% |
| 7h | | | 70% |

-continued

| Ex. | Starting material 1 | Product | Yield |
|---|---|---|---|
| 7j | | | 30% |
| 7i | | | 42% |
| 7k | | | 82% |
| 7l | | | 85% |
| 7m | | | 86% |

| Ex. | Starting material 1 | Product | Yield |
|---|---|---|---|
| 7n | | | 67% |
| 7o | | | 65% |

Example 8: 2-Dibenzofuran-4-yl-8a-azabenzo[fg]naphthacene-8,9-dione

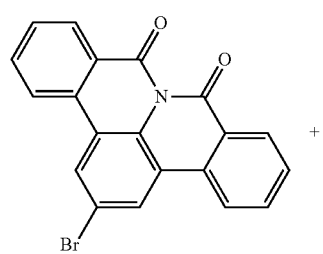

+

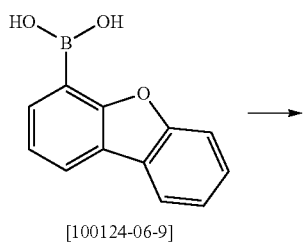

[100124-06-9]

→

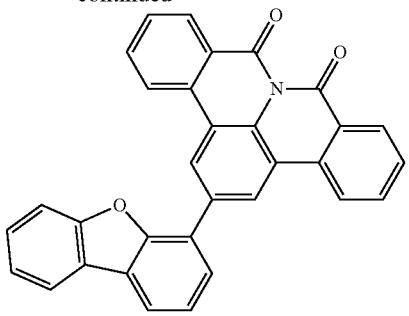

41.3 g (110.0 mmol) of 4-dibenzofuranboronic acid, 38 g (110.0 mmol) of 2-bromo-8a-azabenzo[fg]naphthacene-8,9-dione and 44.6 g (210.0 mmol) of tripotassium phosphate are suspended in 500 ml of toulene, 500 ml of dioxane and 500 ml of water. 913 mg (3.0 mmol) of tri-o-tolylphosphine and then 112 mg (0.5 mmol) of palladium(II) acetate are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene and from dichloromethane/isopropanol and finally sublimed in a high vacuum, purity is 99.9%. The yield is 40 g (88 mmol), corresponding to 80% of theory.

The following compounds are obtained analogously:

| Ex. | Starting material 1 | Starting material 2 | Product | Yield. |
|---|---|---|---|---|
| 8a | | 236389-21-2 | | 82% |
| 8b | | [854952-58-2] | | 81% |
| 8c | | [943036-24-5] | | 84% |

-continued

| Ex. | Starting material 1 | Starting material 2 | Product | Yield. |
|---|---|---|---|---|
| 8e | | [128388-54-5] | | 88% |
| 8f | | [1338488-91-7] | | 67% |
| 8g | | [1001911-63-2] | | 75% |

-continued
| Ex. | Starting material 1 | Starting material 2 | Product | Yield. |
|---|---|---|---|---|
| 8h | 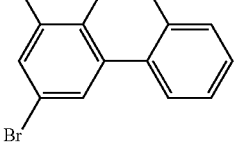 | 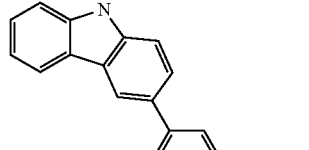\n[854952-60-6] | 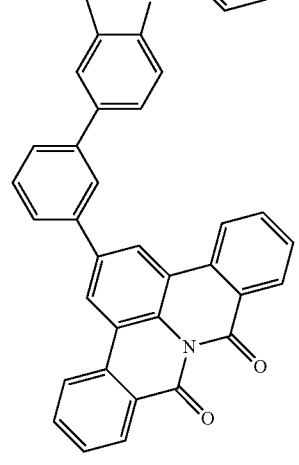 | 76% |
| 8j | 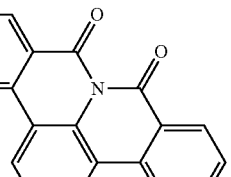 | 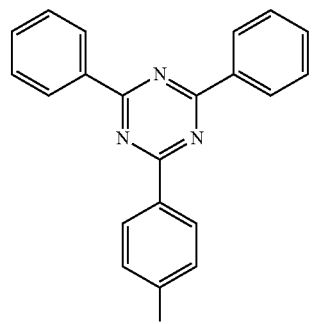\n[1313018-07-3] | 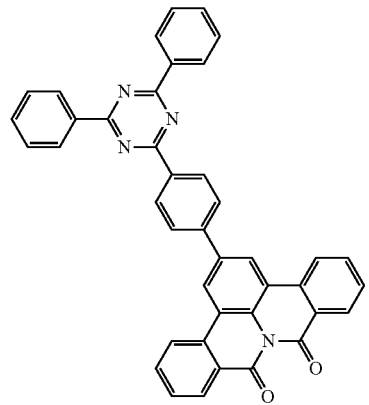 [SMILES: O=c1c2ccccc2c2cc(-c3ccc(-c4nc(-c5ccccc5)nc(-c5ccccc5)n4)cc3)cc3c4ccccc4c(=O)n1c23] | 83% |
| 8i | 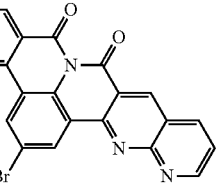 | 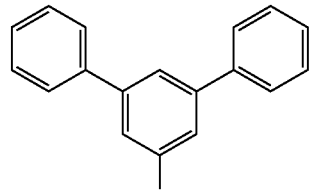\n[128388-54-5] | 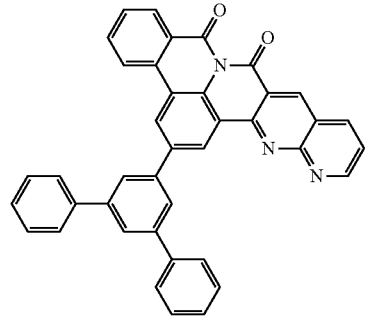 [SMILES: O=c1c2ccccc2c2cc(-c3cc(-c4ccccc4)cc(-c4ccccc4)c3)cc3c4nc5ncccc5cc4c(=O)n1c23] | 85% |

-continued
| Ex. | Starting material 1 | Starting material 2 | Product | Yield. |
|---|---|---|---|---|
| 8k | 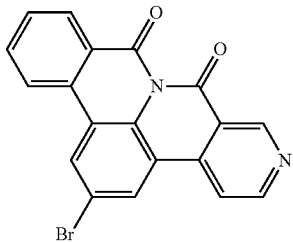 [SMILES: O=c1c2ccccc2c2cc(Br)cc3c4ccncc4c(=O)n1c23] | 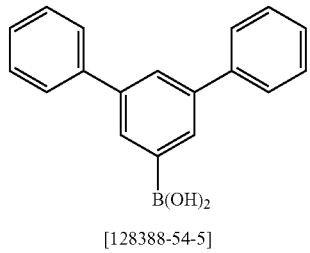 [SMILES: OB(O)c1cc(-c2ccccc2)cc(-c2ccccc2)c1]  [128388-54-5] | 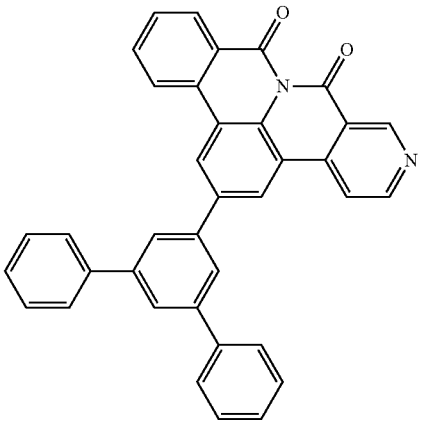 [SMILES: O=c1c2ccccc2c2cc(-c3cc(-c4ccccc4)cc(-c4ccccc4)c3)cc3c4ccncc4c(=O)n1c23] | 80% |
| 8l | 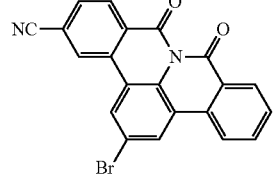 | 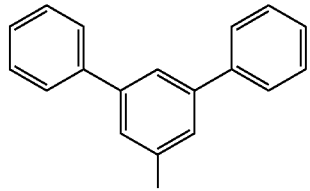  [128388-54-5] | 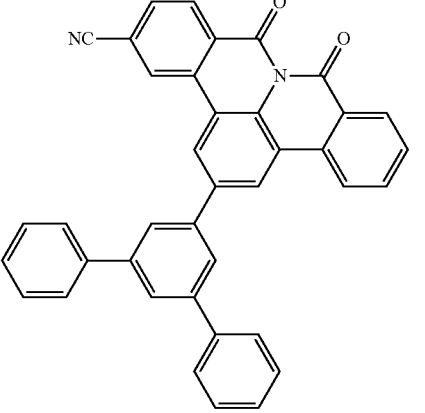 | 89% |
| 8m | 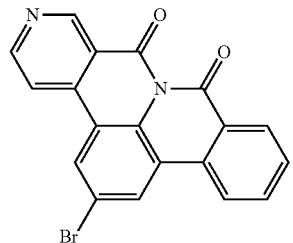 [SMILES: O=c1c2ccccc2c2cc(Br)cc3c4ccncc4c(=O)n1c23] | 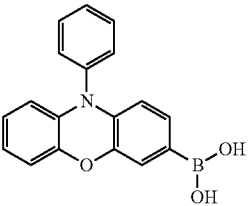  [1314019-67-4] | 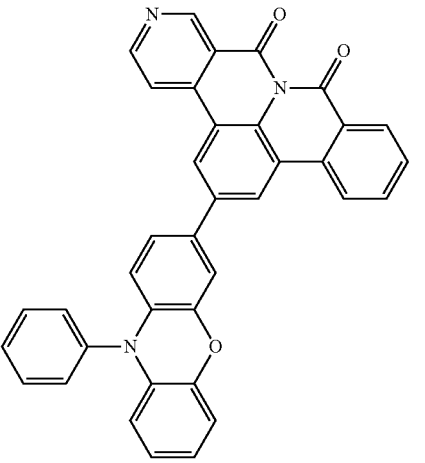 [SMILES: O=c1c2ccccc2c2cc(-c3ccc4c(c3)Oc3ccccc3N4c3ccccc3)cc3c4ccncc4c(=O)n1c23] | 88% |

-continued
| Ex. | Starting material 1 | Starting material 2 | Product | Yield. |
|---|---|---|---|---|
| 8n | 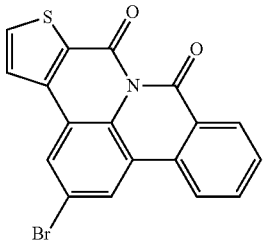 [SMILES: O=c1c2ccccc2c2cc(Br)cc3c4ccsc4c(=O)n1c23] | 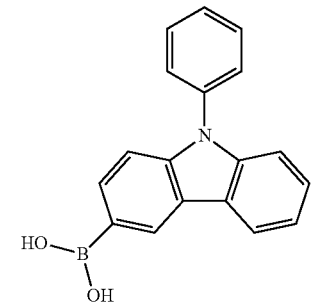 [854952-58-2] | 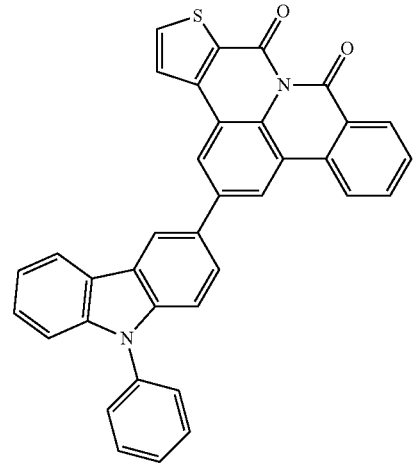 [SMILES: O=c1c2ccccc2c2cc(-c3ccc4c(c3)c3ccccc3n4-c3ccccc3)cc3c4ccsc4c(=O)n1c23] | 86% |
| 8o | 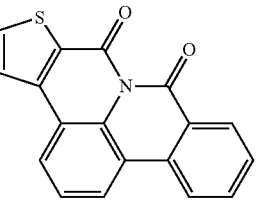 | 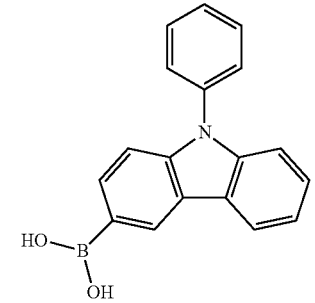 [854952-58-2] | 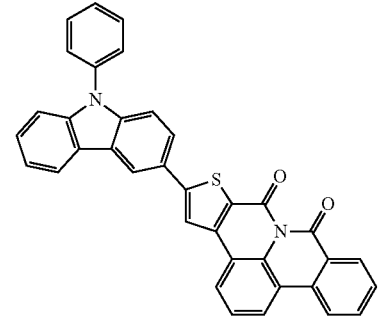 [SMILES: O=c1c2ccccc2c2cccc3c4cc(-c5ccc6c(c5)c5ccccc5n6-c5ccccc5)sc4c(=O)n1c23] | 82% |
| 8p | 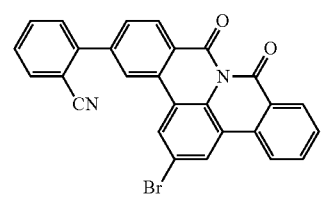 [SMILES: N#Cc1ccccc1-c1ccc2c(=O)n3c(=O)c4ccccc4c4cc(Br)cc(c2c1)c43] | 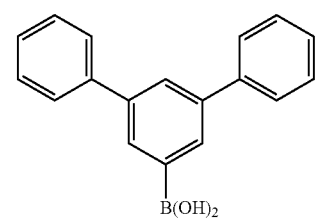 [128388-54-5] | 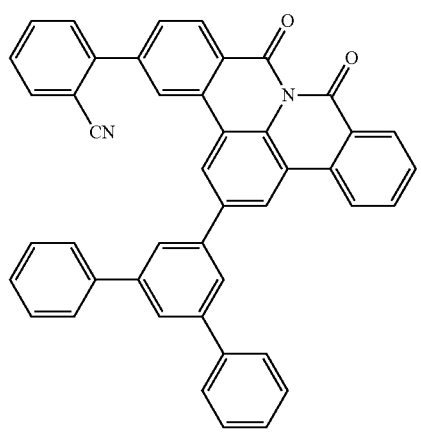 [SMILES: N#Cc1ccccc1-c1ccc2c(=O)n3c(=O)c4ccccc4c4cc(-c5cc(-c6ccccc6)cc(-c6ccccc6)c5)cc(c2c1)c43] | 86% |

-continued

| Ex. | Starting material 1 | Starting material 2 | Product | Yield. |
|---|---|---|---|---|
| 8q | | [854952-58-2] | | 87% |
| 8r | | [854952-58-2] | | 81% |
| 8s | | [1251825-65-8] | | 79% |

| Ex. | Starting material 1 | Starting material 2 | Product | Yield. |
|---|---|---|---|---|
| 8t | 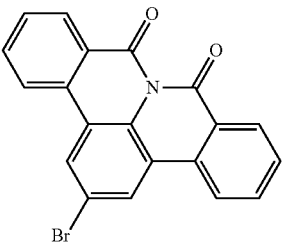 [SMILES: O=c1c2ccccc2c2cc(Br)cc3c4ccccc4c(=O)n1c23] | 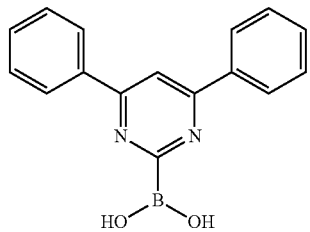
[1314221-56-1] | 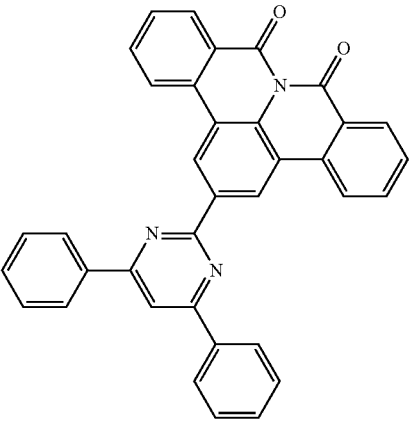 | 86% |
| 8u | 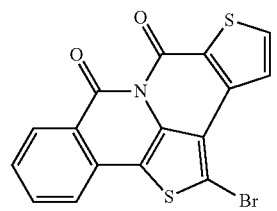 [SMILES: O=c1c2ccccc2c2sc(Br)c3c4ccsc4c(=O)n1c23] | 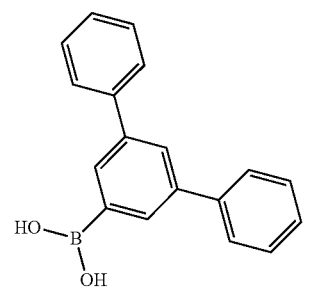
[128388-54-5] | 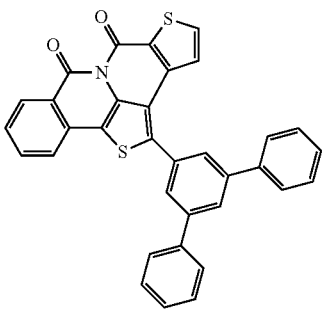 [SMILES: O=c1c2ccccc2c2sc(-c3cc(-c4ccccc4)cc(-c4ccccc4)c3)c3c4ccsc4c(=O)n1c23] | 87% |
| 8v | 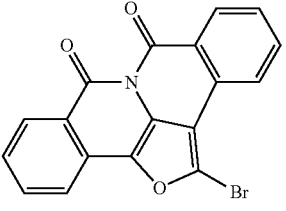 [SMILES: O=c1c2ccccc2c2oc(Br)c3c4ccccc4c(=O)n1c23] | 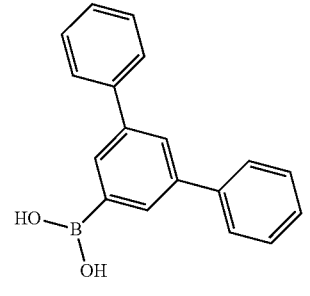
[128388-54-5] | 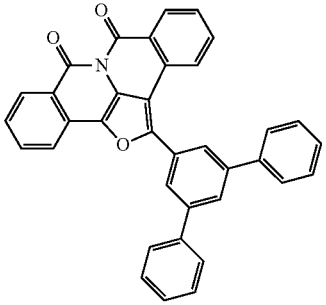 [SMILES: O=c1c2ccccc2c2oc(-c3cc(-c4ccccc4)cc(-c4ccccc4)c3)c3c4ccccc4c(=O)n1c23] | 80% |

-continued
| Ex. | Starting material 1 | Starting material 2 | Product | Yield. |
|---|---|---|---|---|
| 8w | 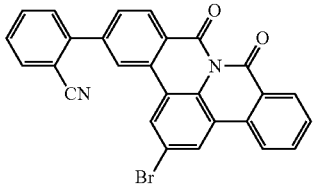 [SMILES: N#Cc1ccccc1-c1ccc2c(=O)n3c(=O)c4ccccc4c4cc(Br)cc(c2c1)c43] | 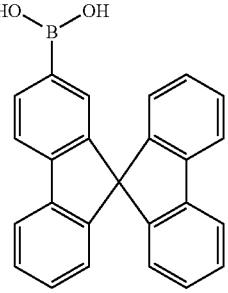
236389-21-2 | 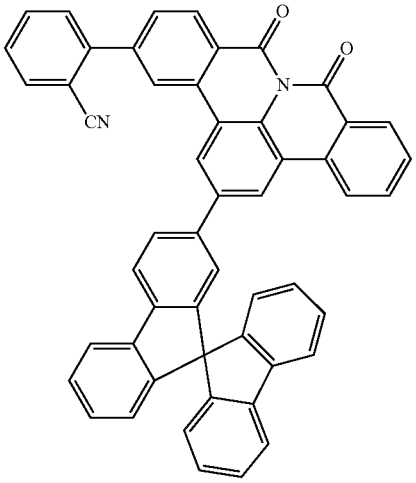 [SMILES: N#Cc1ccccc1-c1ccc2c(=O)n3c(=O)c4ccccc4c4cc(-c5ccc6c(c5)C5(c7ccccc7-c7ccccc75)c5ccccc5-6)cc(c2c1)c43] | 81% |
| 8y | 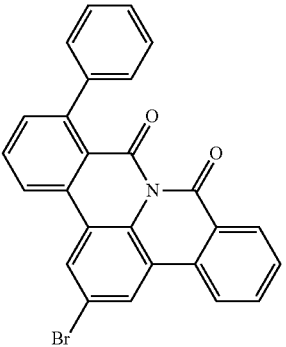 [SMILES: O=c1c2ccccc2c2cc(Br)cc3c4cccc(-c5ccccc5)c4c(=O)n1c23] | 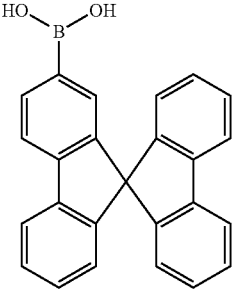
236389-21-2 | 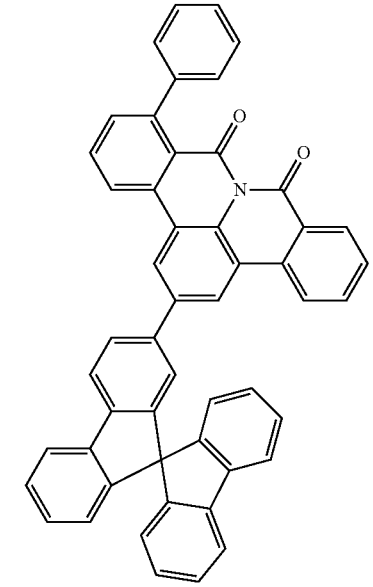 [SMILES: O=c1c2ccccc2c2cc(-c3ccc4c(c3)C3(c5ccccc5-c5ccccc53)c3ccccc3-4)cc3c4cccc(-c5ccccc5)c4c(=O)n1c23] | 83% |
| 8z | 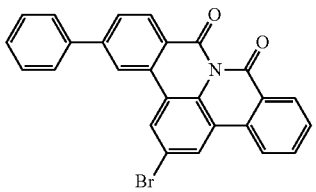 [SMILES: O=c1c2ccccc2c2cc(Br)cc3c4cc(-c5ccccc5)ccc4c(=O)n1c23] | 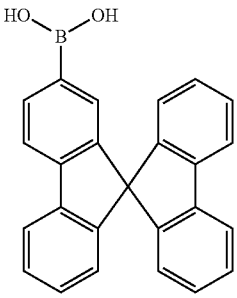
236389-21-2 | 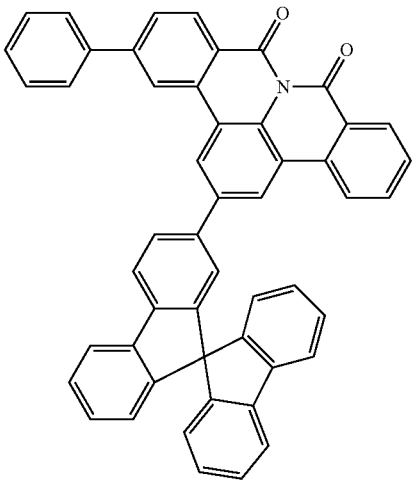 [SMILES: O=c1c2ccccc2c2cc(-c3ccc4c(c3)C3(c5ccccc5-c5ccccc53)c3ccccc3-4)cc3c4cc(-c5ccccc5)ccc4c(=O)n1c23] | 84% |

The following compounds are obtained analogously using 0.5 eq. of bromine:

| Ex. | Starting material 1 | Starting material 2 | Product | Yield |
|---|---|---|---|---|
| 8w | (bromo-dibenzo phenanthridinone) | benzene-1,4-diboronic acid [4612-26-4] | bis(dibenzo phenanthridinone)-phenylene | 86% |
| 8y | (bromo-dibenzo phenanthridinone) | 9-phenylcarbazole-3,6-diboronic acid [1135916-40-3] | bis(dibenzo phenanthridinone)-(9-phenylcarbazole) | 81% |

Example 9: 2-{3-Phenyl-6-[(E)-((Z)-1-propenyl)buta-1,3-dienyl]carbazol-9-yl}-8a-azabenzo[fg]naphthacene-8,9-dione

Example 10: 2-(Bisbiphenyl-4-ylamino)-8a-azabenzo[fg]naphthacene-8,9-dione

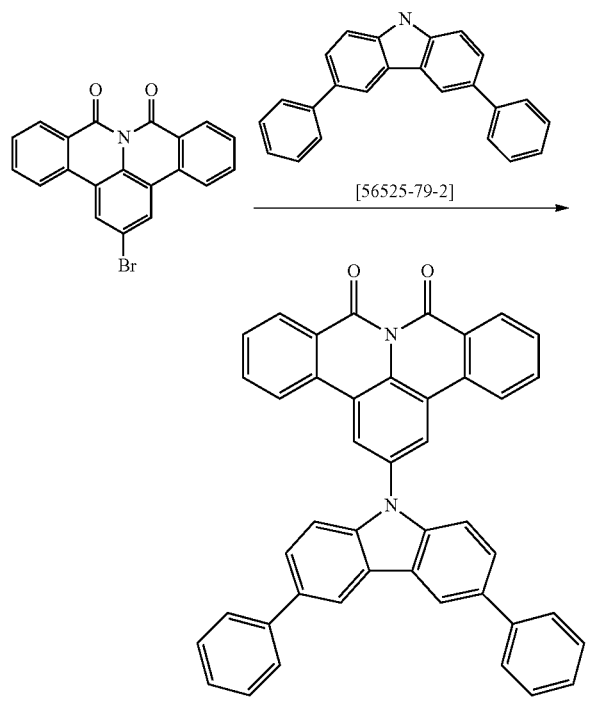
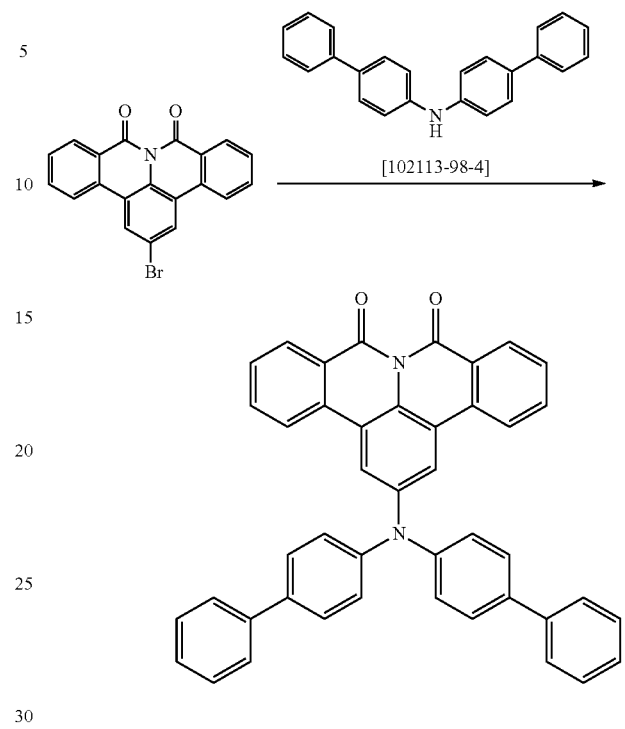

32 g (102-4 mmol) of 3,6-diphenyl-9H-carbazole, 42 g (112 mmol) of 2-bromo-8a-azabenzo[fg]naphthacene-8,9-dione and 2.3 (10-2 mmol) of 1,3-di[2-pyridyl]-1,3-propanedione, 28.3 g (204 mmol) of potassium carbonate and 1.9 g (10.2 mmol) of copper iodide are stirred under reflux in 1000 ml of DMF for 90 h. The solution is diluted with water and extracted twice with ethyl acetate, the combined organic phases are dried over $Na_2SO_4$ and evaporated in a rotary evaporator and purified by chromatography (EtOAc/hexane: 2/3). The residue is recrystallised from toluene and from dichloromethane and finally sublimed in a high vacuum, purity is 99.9%. The yield is 46 g (75 mmol), corresponding to 68% of theory.

The following compounds are obtained analogously:

Under protective gas, 24.5 g (79.8 mmol) of bisbiphenyl-4-ylamine, 32.7 g (87 mmol) of 2-bromo-8a-azabenzo[fg]naphthacene-8,9-dione, 15.9 ml (15.9 mmol) of 1 mol/l tri-tert-butylphosphine and 1.79 g (7.9 mmol) of palladium acetate are suspended in 120 ml of p-xylene. The reaction mixture is heated under reflux for 16 h. After cooling, the organic phase is separated off, washed three times with 200 ml of water and subsequently evaporated to dryness. The residue is extracted with hot toluene, recrystallised from toluene and finally sublimed in a high vacuum. The purity is 99.9%, yield 44 g (72 mmol), 83% of theory.

| Ex. | Starting material 1 | Starting material 2 | Product | Yield |
|---|---|---|---|---|
| 9a | (structure, Br) | (structure, [1257220-47-5]) | (structure) | 65% |

The following compounds are obtained analogously:

| Ex. | Starting material 1 | Starting material 2 | Product | Yield |
|---|---|---|---|---|
| 10a | 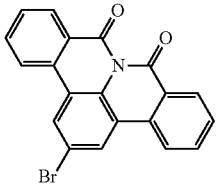 | 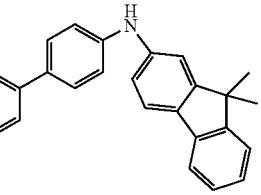  [597871-69-1] | 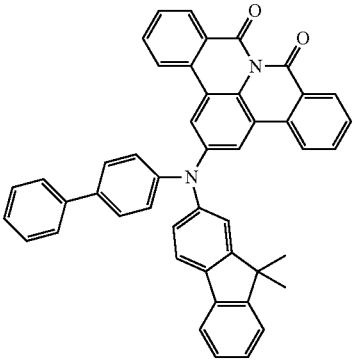 [SMILES: CC1(C)c2ccccc2-c2ccc(N(c3ccc(-c4ccccc4)cc3)c3cc4c5ccccc5c(=O)n5c(=O)c6ccccc6c(c3)c45)cc21] | 85% |
| 10b | 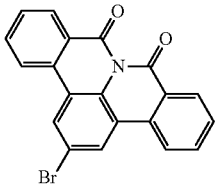 [SMILES: O=c1c2ccccc2c2cc(Br)cc3c4ccccc4c(=O)n1c23] | 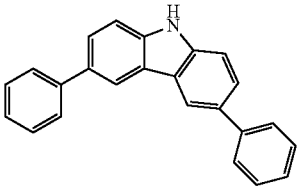  [58525-78-2] | 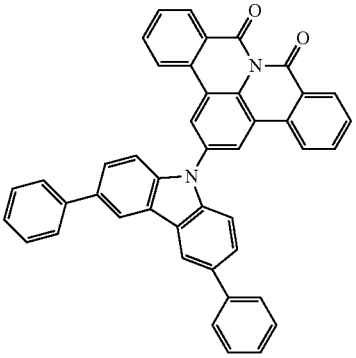 [SMILES: O=c1c2ccccc2c2cc(-n3c4ccc(-c5ccccc5)cc4c4cc(-c5ccccc5)ccc43)cc3c4ccccc4c(=O)n1c23] | 76% |

Example 11: 1-(2-Bromobenzyl)-3-phenyl-1,3-dihydrobenzoimidazol-2-one

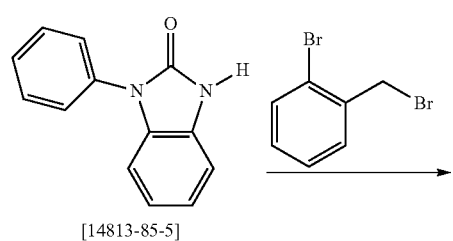

[14813-85-5]

1-Phenyl-1,3-dihydrobenzoimidazol-2-one 52 g (250 mmol) and 38 g (275 mmol) of $K_2CO_3$ are initially introduced in 100 ml of DMF. After 1 h at room temperature, a solution of 62 g (250 mmol) of 2-bromobenzyl bromide in 500 ml of DMF is added dropwise. The reaction mixture is then stirred at room temperature for 25 h. After this time, the reaction mixture is poured onto ice and extracted three times with dichloromethane. The combined organic phases are dried over $Na_2SO_4$ and evaporated. The residue is extracted with hot toluene and recrystallised from toluene/n-heptane. The yield is 65 g (70%).

The following compounds are obtained analogously:
| Ex. | Starting material 1 | Starting material 2 | Product | Yield |
|---|---|---|---|---|
| 11a | 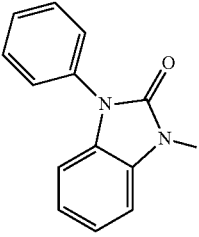 [1225484-71-8] | 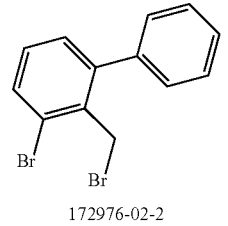 [SMILES: BrCc1c(Br)cccc1-c1ccccc1] 172976-02-2 | 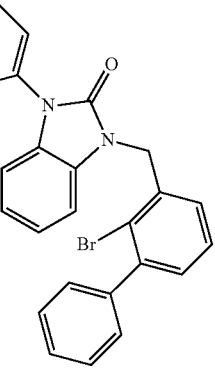 | 76% |
| 11b | 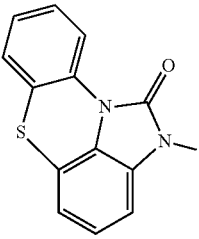 [30017-73-3] | 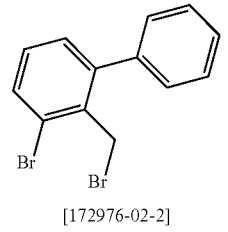 [SMILES: BrCc1c(Br)cccc1-c1ccccc1] [172976-02-2] | 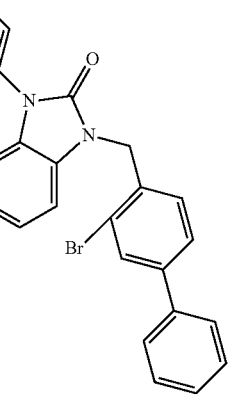 | 71% |
The following compounds are obtained analogously using 125 mmol of 1,3-dihydro-2H-benzimidazol-2-one [615-16-7]:
| Ex. | Starting material 1 | Starting material 2 | Product | Yield. |
|---|---|---|---|---|
| 11c | 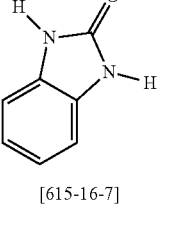 [615-16-7] | 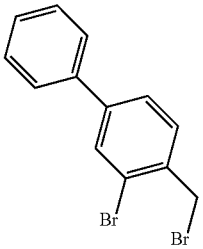 [1396865-04-5] | 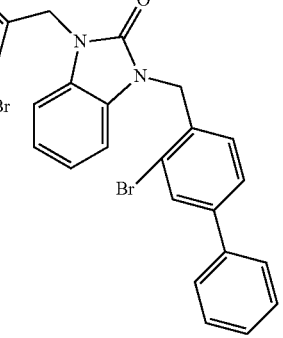 | 86% |
| 11d | 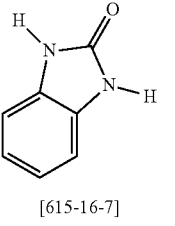 [615-16-7] | 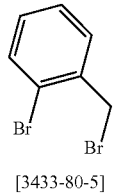 [3433-80-5] | 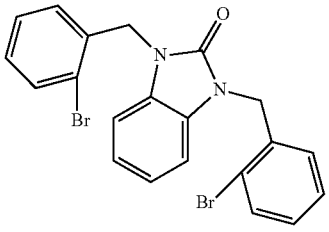 [SMILES: O=c1n(Cc2ccccc2Br)c2ccccc2n1Cc1ccccc1Br] | 82% |

The cyclisation is carried out analogously to Example 5:

| Ex. | Starting material 1 | Product | Yield |
|---|---|---|---|
| 5d | | | 62% |
| 5e | | | 63% |
| 5f | | | 74% |
| 5h | | | 66% |

-continued

| Ex. | Starting material 1 | Product | Yield |
|---|---|---|---|
| 5j | | | 64% |

The further oxidation is carried out analogously to Example 6:

| Ex. | Starting material 1 | Product | Yield |
|---|---|---|---|
| 6n | | | 60% |
| 6o | | | 69% |
| 6p | | | 71% |

-continued

| Ex. | Starting material 1 | Product | Yield |
|---|---|---|---|
| 6q | | | 70% |
| 6r | | | 67% |

The bromination is carried out analogously to Example 7:

| Ex. | Starting material 1 | Product | Yield |
|---|---|---|---|
| 7n | | | 60% |
| 7o | | | 69% |

-continued

| Ex. | Starting material 1 | Product | Yield |
|---|---|---|---|
| 7p | | | 71% |
| 7q | | | 70% |
| 7r | | | 67% |

The following compounds are prepared analogously to Example 9 via Ullmann reaction:

| Ex. | Starting material 1 | Starting material 2 | Product | Yield |
|---|---|---|---|---|
| 9b | | [1257220-47-5] | | 64% |

| Ex. | Starting material 1 | Starting material 2 | Product | Yield |
|---|---|---|---|---|
| 9c | | [1257220-47-5] | | 63% |
| 9d | | [1257220-47-5] | | 65% |
| 9e | | [1257220-47-5] | | 66% |
| 9f | | [58525-79-2] | | 71% |

Example 12: Production of OLEDs

The data of various OLEDs are presented in the following Examples E1 to 7 (see Tables 1 and 2). Glass plates coated with structured ITO (indium tin oxide) in a thickness of 50 nm are coated with 20 nm of PEDOT:PSS (poly(3,4-ethylenedioxythiophene) poly(styrenesulfonate), purchased as CLEVIOS™ P VP AI 4083 from Heraeus Precious Metals GmbH Germany, applied by spin coating from aqueous solution) for improved processing. These coated glass plates form the substrates to which the OLEDs are applied. The OLEDs have in principle the following layer structure: substrate/hole-transport layer (HTL)/interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is shown in Table 1. The materials required for the production of the OLEDs are shown in Table 3. A designation such as "8a" here refers to the corresponding compound from the above-mentioned Example 8a. This applies analogously to all materials according to the invention that are used.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by co-evaporation. An expression such as IC1:8c:TER1 (55%:35%:10%) here means that material IC1 is present in the layer in a proportion by volume of 55%, 8c is present in the layer in a proportion of 35% and TER1 is present in the layer in a proportion of 10%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m$^2$, and the CIE 1931 x and y colour coordinates are calculated therefrom. The term U1000 in Table 2 denotes the voltage required for a luminous density of 1000 cd/m$^2$. CE1000 and PE1000 denote the current and power efficiency respectively which are achieved at 1000 cd/m$^2$. Finally, EQE1000 denotes the external quantum efficiency at an operating luminous density of 1000 cd/m$^2$. The lifetime LT is defined as the time after which the luminous density drops from the initial luminous density to a certain proportion L1 on operation at constant current. An expression of L0;j0=4000 cd/m$^2$ and L1=80% in Table 2 means that the lifetime indicated in column LT corresponds to the time after which the initial luminous density drops from 4000 cd/m$^2$ to 3200 cd/m$^2$. Analogously, L0;j0=20 mA/cm$^2$, L1=70%, means that the luminous density drops to 70% of its initial value after time LT on operation at 20 mA/cm$^2$.

The data of the various OLEDs are summarised in Table 2. On use of the compounds according to the invention both on use as electron-transport material (Examples E1, E2, E13, E17, E18) and also as matrix material for phosphorescent emitters (remaining examples), very good values for efficiency, voltage and lifetime are obtained. This applies on use as single matrix and also in mixed-matrix systems in combination with various materials, such as IC1, IC2, Cbz1. In particular, the excellent voltages and thus power efficiencies at the same time as a very good lifetime should be emphasised (see, for example, E10).

TABLE 1

Structure of the OLEDs

| Ex. | HTL Thickness | IL Thickness | EBL Thickness | EML Thickness | HBL Thickness | ETL Thickness | EIL Thickness |
|---|---|---|---|---|---|---|---|
| E1 | SpA1 140 nm | HATCN 5 nm | SpMA1 20 nm | M1:D1 (95%:5%) 20 nm | — | 8k 30 nm | LiQ 3 nm |
| E2 | SpA1 140 nm | HATCN 5 nm | SpMA1 20 nm | M1:D1 (95%:5%) 20 nm | — | 8s:LiQ (50%:50%) 30 nm | — |
| E3 | SpA1 70 nm | HATCN 5 nm | SpMA1 90 nm | IC1:TEG1 (90%:10%) 30 nm | — | 8s:LiQ (50%:50%) 40 nm | — |
| E4 | SpA1 70 nm | HATCN 5 nm | SpMA1 90 nm | 8:TEG1 (90%:10%) 30 nm | — | ST1:LiQ (50%:50%) 40 nm | — |
| E5 | SpA1 90 nm | HATCN 5 nm | SpMA1 130 nm | 8a:TER1 (92%:8%) 40 nm | — | ST1:LiQ (50%:50%) 40 nm | — |
| E6 | SpA1 70 nm | HATCN 5 nm | SpMA1 90 nm | 8b:TEG1 (90%:10%) 30 nm | — | ST1:LiQ (50%:50%) 40 nm | — |
| E7 | SpA1 90 nm | HATCN 5 nm | SpMA1 130 nm | 8b:TER1 (92%:8%) 40 nm | — | ST1:LiQ (50%:50%) 40 nm | — |
| E8 | SpA1 90 nm | HATCN 5 nm | SpMA1 130 nm | IC1:8c:TER1 (55%:35%:10%) 40 nm | IC1 5 nm | ST1:LiQ (50%:50%) 35 nm | — |
| E9 | SpA1 70 nm | HATCN 5 nm | SpMA1 90 nm | 8e:TEG1 (90%:10%) 30 nm | — | ST1:LiQ (50%:50%) 40 nm | — |
| E10 | SpA1 70 nm | HATCN 5 nm | SpMA1 90 nm | 8e:IC2:TEG1 (45%:45%:10%) 40 nm | — | ST1:LiQ (50%:50%) 30 nm | — |

TABLE 1-continued

Structure of the OLEDs

| Ex. | HTL Thickness | IL Thickness | EBL Thickness | EML Thickness | HBL Thickness | ETL Thickness | EIL Thickness |
|---|---|---|---|---|---|---|---|
| E11 | SpA1 70 nm | HATCN 5 nm | SpMA1 90 nm | 8e:Cbz1:TEG1 (60%:35%:5%) 30 nm | IC1 10 nm | ST1:LiQ (50%:50%) 30 nm | — |
| E12 | SpA1 70 nm | HATCN 5 nm | SpMA1 90 nm | 8k:TEG1 (90%:10%) 30 nm | — | ST1:LiQ (50%:50%) 40 nm | — |
| E13 | SpA1 70 nm | HATCN 5 nm | SpMA1 90 nm | IC1:TEG1 (90%:10%) 30 nm | — | 8o 40 nm | LiQ 3 nm |
| E14 | SpA1 70 nm | HATCN 5 nm | SpMA1 90 nm | 8r:TEG1 (90%:10%) 30 nm | — | ST1:LiQ (50%:50%) 40 nm | — |
| E15 | SpA1 70 nm | HATCN 5 nm | SpMA1 90 nm | 8s:TEG1 (90%:10%) 30 nm | — | ST1:LiQ (50%:50%) 40 nm | — |
| E16 | SpA1 90 nm | HATCN 5 nm | SpMA1 130 nm | 8s:TER1 (92%:8%) 40 nm | — | ST1:LiQ (50%:50%) 40 nm | — |
| E17 | SpA1 70 nm | HATCN 5 nm | SpMA1 90 nm | IC1:TEG1 (90%:10%) 30 nm | — | 8s 40 nm | LiF 1 nm |
| E18 | SpA1 140 nm | HATCN 5 nm | SpMA1 20 nm | M1:D1 (95%:5%) 20 nm | — | 8v 30 nm | LiQ 3 nm |
| E19 | SpA1 90 nm | HATCN 5 nm | SpMA1 130 nm | 8w:TER1 (92%:8%) 40 nm | — | ST1:LiQ (50%:50%) 40 nm | — |
| E20 | SpA1 70 nm | HATCN 5 nm | SpMA1 90 nm | 8w:TEG1 (90%:10%) 30 nm | — | ST1:LiQ (50%:50%) 40 nm | — |
| E21 | SpA1 90 nm | HATCN 5 nm | SpMA1 130 nm | 8y:TER1 (92%:8%) 40 nm | — | ST1:LiQ (50%:50%) 40 nm | — |
| E22 | SpA1 90 nm | HATCN 5 nm | SpMA1 130 nm | 9:TER1 (92%:8%) 40 nm | — | ST1:LiQ (50%:50%) 40 nm | — |
| E23 | SpA1 90 nm | HATCN 5 nm | SpMA1 130 nm | 9a:TER1 (92%:8%) 40 nm | — | ST1:LiQ (50%:50%) 40 nm | — |
| E24 | SpA1 70 nm | HATCN 5 nm | SpMA1 90 nm | 9b:TEG1 (90%:10%) 30 nm | — | ST1:LiQ (50%:50%) 40 nm | — |
| E25 | SpA1 70 nm | HATCN 5 nm | SpMA1 90 nm | 9c:TEG1 (90%:10%) 30 nm | — | ST1:LiQ (50%:50%) 40 nm | — |
| E26 | SpA1 90 nm | HATCN 5 nm | SpMA1 130 nm | 9f:TER1 (92%:8%) 40 nm | — | ST1:LiQ (50%:50%) 40 nm | — |
| E27 | SpA1 90 nm | HATCN 5 nm | SpMA1 130 nm | IC2:10:TER1 (70%:20%:10%) 40 nm | IC1 5 nm | ST1:LiQ (50%:50%) 35 nm | — |

TABLE 2

Data of the OLEDs

| Ex. | U1000 (V) | CE1000 (cd/A) | PE1000 (lm/W) | EQE 1000 | CIE x/y at 1000 cd/M1 | L0; j0 | L1 % | LT (h) |
|---|---|---|---|---|---|---|---|---|
| E1 | 4.7 | 8.1 | 5.4 | 7.2% | 0.13/0.14 | 60 mA/cm$^2$ | 70 | 200 |
| E2 | 4.5 | 8.5 | 5.9 | 7.3% | 0.13/0.14 | 60 mA/cm$^2$ | 70 | 225 |
| E3 | 3.4 | 61 | 57 | 16.7% | 0.33/0.62 | 20 mA/cm$^2$ | 70 | 220 |
| E4 | 3.3 | 56 | 53 | 15.3% | 0.32/0.62 | 20 mA/cm$^2$ | 70 | 240 |
| E5 | 4.4 | 12.2 | 8.6 | 13.2% | 0.67/0.33 | 4000 cd/m$^2$ | 80 | 360 |
| E6 | 3.5 | 54 | 48 | 14.7% | 0.33/0.63 | 20 mA/cm$^2$ | 70 | 195 |
| E7 | 4.6 | 11.0 | 7.5 | 11.9% | 0.67/0.33 | 4000 cd/m$^2$ | 80 | 345 |
| E8 | 4.1 | 12.6 | 9.6 | 13.6% | 0.67/0.33 | 4000 cd/m$^2$ | 80 | 490 |
| E9 | 3.0 | 54 | 57 | 14.8% | 0.32/0.62 | 20 mA/cm$^2$ | 70 | 260 |
| E10 | 3.0 | 61 | 65 | 16.7% | 0.34/0.63 | 20 mA/cm$^2$ | 80 | 310 |
| E11 | 3.3 | 63 | 61 | 17.4% | 0.32/0.62 | 20 mA/cm$^2$ | 80 | 265 |
| E12 | 3.4 | 52 | 48 | 14.4% | 0.33/0.61 | 20 mA/cm$^2$ | 80 | 180 |
| E13 | 3.6 | 57 | 50 | 15.6% | 0.32/0.62 | 10000 cd/m$^2$ | 70 | 220 |
| E14 | 3.2 | 55 | 54 | 15.0% | 0.32/0.62 | 20 mA/cm$^2$ | 70 | 230 |
| E15 | 3.3 | 54 | 51 | 14.7% | 0.33/0.61 | 20 mA/cm$^2$ | 80 | 145 |
| E16 | 4.6 | 10.6 | 7.3 | 11.4% | 0.67/0.33 | 4000 cd/m$^2$ | 80 | 310 |
| E17 | 3.4 | 59 | 55 | 16.1% | 0.33/0.62 | 20 mA/cm$^2$ | 70 | 245 |
| E18 | 4.9 | 7.0 | 4.9 | 6.7% | 0.13/0.14 | 60 mA/cm$^2$ | 70 | 230 |
| E19 | 3.1 | 56 | 56 | 15.5% | 0.34/0.61 | 20 mA/cm$^2$ | 80 | 160 |
| E20 | 3.8 | 10.1 | 8.4 | 10.9% | 0.67/0.33 | 4000 cd/m$^2$ | 80 | 385 |
| E21 | 4.5 | 12 | 8.4 | 13.0% | 0.67/0.33 | 4000 cd/m$^2$ | 80 | 405 |
| E22 | 4.8 | 11 | 7.2 | 11.9% | 0.67/0.33 | 4000 cd/m$^2$ | 80 | 370 |
| E23 | 4.3 | 12.8 | 9.3 | 13.8% | 0.67/0.33 | 4000 cd/m$^2$ | 80 | 420 |
| E24 | 3.0 | 61 | 63 | 17.0% | 0.33/0.62 | 20 mA/cm$^2$ | 80 | 165 |
| E25 | 3.2 | 59 | 58 | 16.4% | 0.32/0.62 | 20 mA/cm$^2$ | 80 | 150 |
| E26 | 4.6 | 11.1 | 7.6 | 12.0% | 0.67/0.33 | 4000 cd/m$^2$ | 80 | 405 |
| E27 | 4.3 | 12.2 | 8.9 | 13.2% | 0.67/0.33 | 4000 cd/m$^2$ | 80 | 520 |

TABLE 3
Structural formulae of the materials for the OLEDs
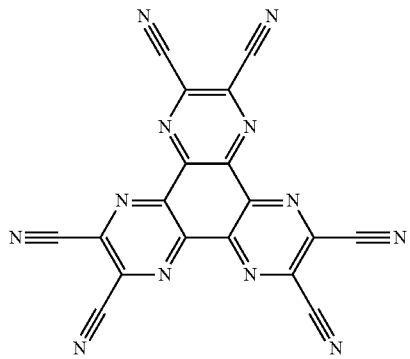 [SMILES: N#Cc1nc2c3nc(C#N)c(C#N)nc3c3nc(C#N)c(C#N)nc3c2nc1C#N]
HATCN
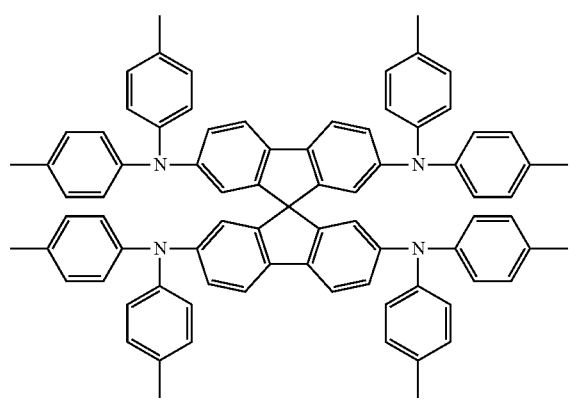
SpA1
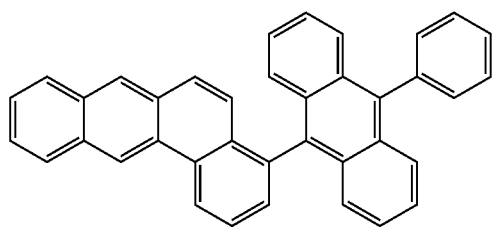 [SMILES: c1ccc(-c2c3ccccc3c(-c3cccc4c3ccc3cc5ccccc5cc34)c3ccccc23)cc1]
M1
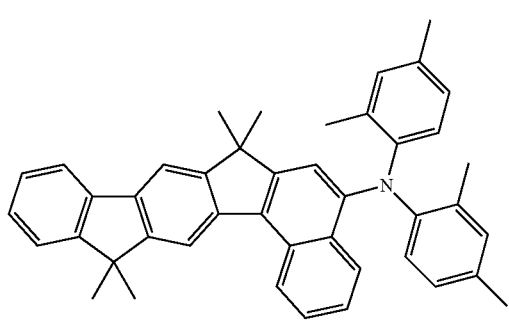 [SMILES: Cc1ccc(N(c2ccc(C)cc2C)c2cc3c(c4ccccc24)-c2cc4c(cc2C3(C)C)-c2ccccc2C4(C)C)c(C)c1]
D1
TABLE 3-continued
Structural formulae of the materials for the OLEDs
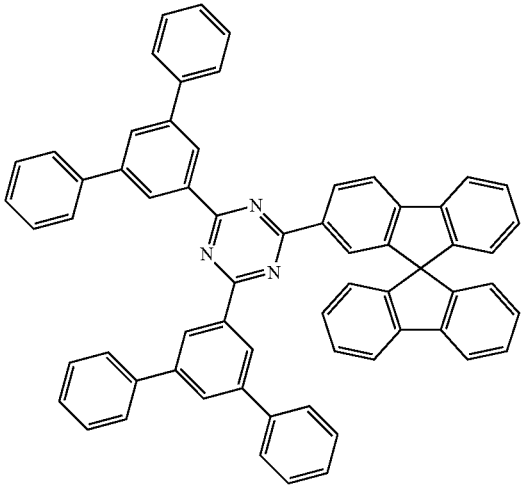 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST1
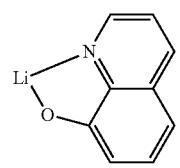
LiQ
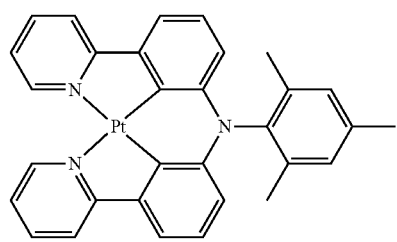
TER1
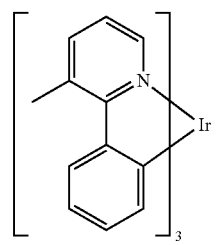
TEG1

TABLE 3-continued

Structural formulae of the materials for the OLEDs

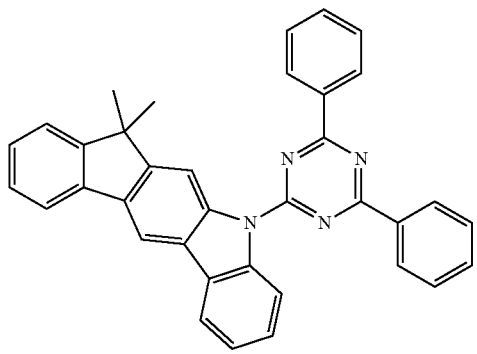 [SMILES: CC1(C)c2ccccc2-c2cc3c4ccccc4n(-c4nc(-c5ccccc5)nc(-c5ccccc5)n4)c3cc21]

IC1

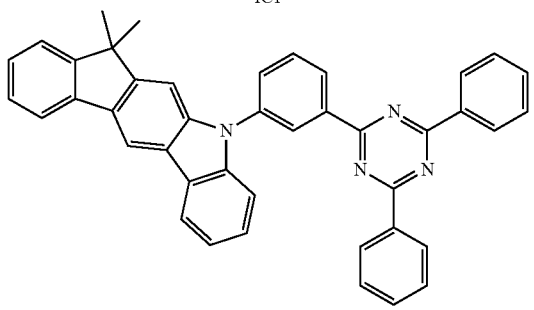

IC2

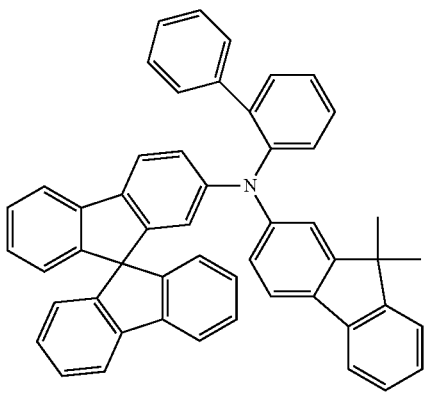 [SMILES: CC1(C)c2ccccc2-c2ccc(N(c3ccc4c(c3)C3(c5ccccc5-c5ccccc53)c3ccccc3-4)c3ccccc3-c3ccccc3)cc21]

SpMA1

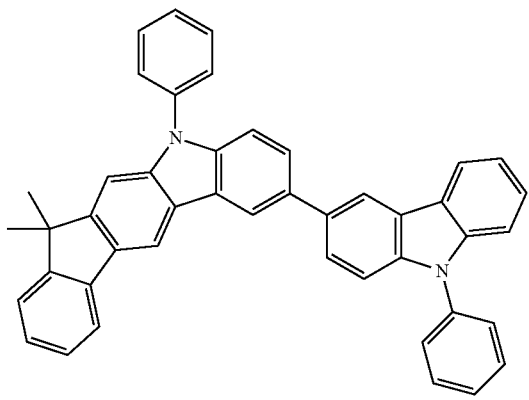 [SMILES: CC1(C)c2ccccc2-c2cc3c4cc(-c5ccc6c(c5)c5ccccc5n6-c5ccccc5)ccc4n(-c4ccccc4)c3cc21]

Cbz1

The invention claimed is:

1. A compound of formula (1),

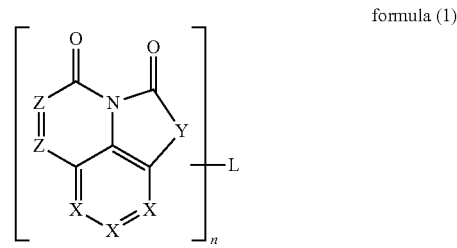

formula (1)

wherein:
X is on each occurrence, identically or differently, CR or N; or two adjacent groups X together stand for a group selected from NR, O or S, resulting in the formation of a five-membered ring;
Y is on each occurrence, identically or differently, Z=Z, O, S or NR, where R is not H;
Z is on each occurrence, identically or differently, CR or N or the adjacent groups Z=Z together stand for a group of formula (2),

formula (2)

where X has the meanings given above and the dashed bonds indicate the linking of this group;
L is not present for n=1 and is a single bond or a divalent group for n=2 and a trivalent group for n=3 and a tetravalent group for n=4 and a pentavalent group for n=5 and a hexavalent group for n=6; L here is bonded at any desired point of the basic structure instead of a group R;
R is selected on each occurrence, identically or differently, from the group consisting of H, D, F, Cl, Br, I, CN, $NO_2$, $N(Ar^1)_2$, $N(R^1)_2$, $C(=O)Ar^1$, $C(=O)R^1$, $P(=O)(Ar^1)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^1$, where one or more non-adjacent $CH_2$ groups may be replaced by $R^1C=CR^1$, $Si(R^1)_2$, C=O, C=S, $C=NR^1$, $P(=O)(R^1)$, SO, $SO_2$, $NR^1$, O, S or $CONR^1$ and where one or more H atoms optionally is replaced by D, F, Cl, Br, I, CN or $NO_2$, an aromatic or heteroaromatic ring system having 5 to 60 aromatic ring atoms, which is optionally in each case substituted by one or more radicals $R^1$, an aryloxy or heteroaryloxy group having 5 to 60 aromatic ring atoms, which is optionally substituted by one or more radicals $R^1$, an aralkyl or heteroaralkyl group having 5 to 60 aromatic ring atoms, which is optionally substituted by one or more radicals $R^1$, or a combination of these systems, where two or more adjacent substituents R may optionally form a monocyclic or polycyclic, aliphatic, aromatic or heteroaromatic ring system, which is optionally substituted by one or more radicals $R^1$;
$Ar^1$ is on each occurrence, identically or differently, an aromatic or heteroaromatic ring system having 5-30 aromatic ring atoms, which is optionally substituted by one or more non-aromatic radicals $R^1$; two radicals $Ar^1$ here which are bonded to the same N atom or P atom may also be bridged to one another by a single bond or a bridge selected from $N(R^1)$, $C(R^1)_2$ or O;

$R^1$ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms is optionally replaced by D, F, Cl, Br, I, CN or an alkyl group having 1 to 10 C atoms or an alkenyl group having 2 to 10 C atoms, where two or more adjacent substituents $R^1$ may form a mono- or polycyclic, aliphatic, aromatic or heteroaromatic ring system with one another;

n is 1, 2, 3, 4, 5 or 6;

where the following compound is excluded from the invention:

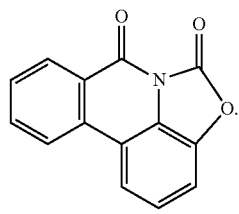 [SMILES: O=c1oc2cccc3c4ccccc4c(=O)n1c23]

2. The compound according to claim 1, selected from the compounds of formula (5) and formula (9), formula (5)

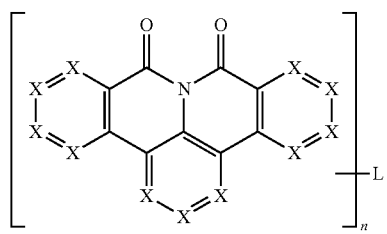

formula (9)

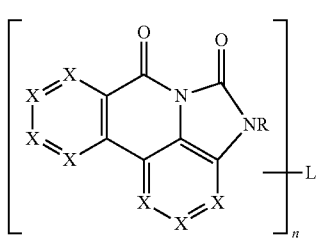

where the radical R on the nitrogen in formula (9) is not equal to H.

3. The compound according to claim 1, selected from compounds of formula (6), formula (6)

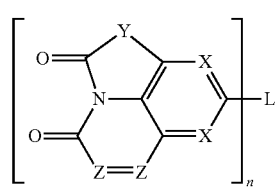

where n=2 or 3.

4. The compound according to claim 1, selected from compounds of formulae (7), (8), (10) and (11), formula (7)

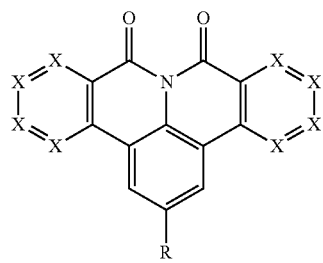

formula (8)

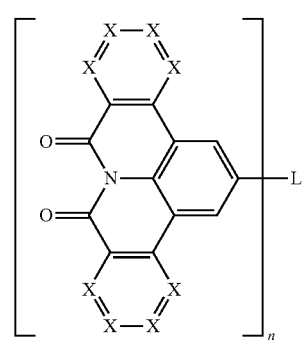

formula (10)

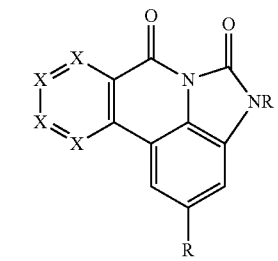

formula (11)

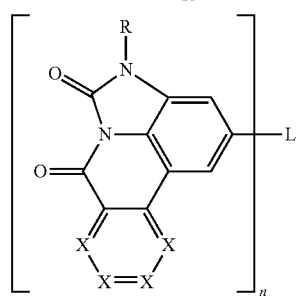

where n stands for 2 or 3, a maximum of one group X per ring stands for N and the other groups X stand for CR and the radical R on the nitrogen in formula (10) and (11) is not equal to H.

5. The compound according to claim 1, selected from compounds of formulae (7a), (8a), (10a) and (11a), formula (7a)

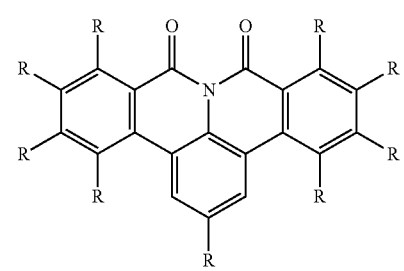

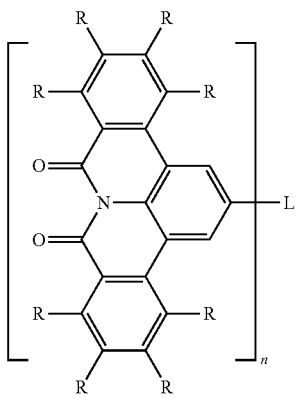

formula (10a)

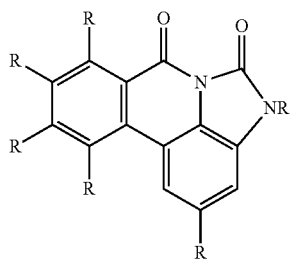

formula (11a)

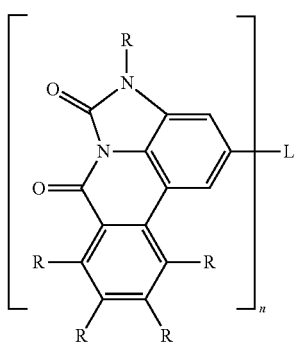

where n stands for 2 or 3, and the radical R on the nitrogen in formula (10a) and (11a) is not equal to H.

6. The compound according to claim 1, selected from compounds of formulae (7c), (8c), (10c) and (11c), formula (7c)

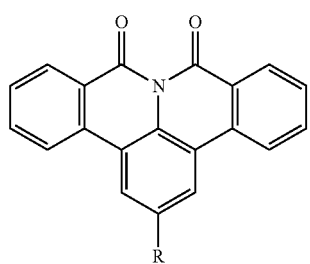

formula (8c)

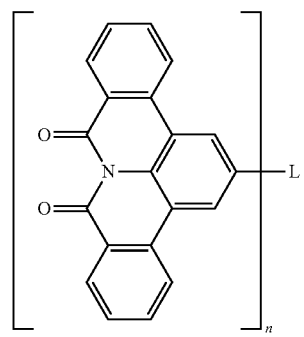

formula (10c)

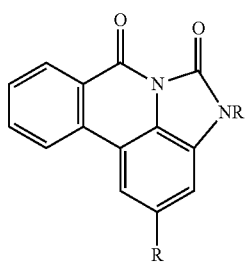

formula (11c)

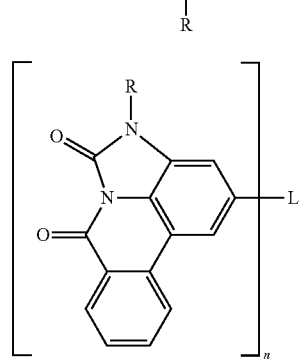

where n stands for 2 or 3, and the radical R on the nitrogen in formula (10c) and (11c) is not equal to H.

7. The compound according to claim 1, selected from compounds of formula (12), formula (12)

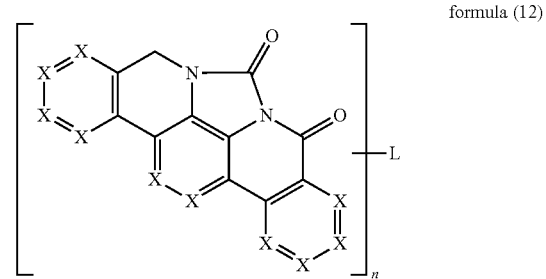

8. The compound according to claim 1, characterised in that L, for n=2, is selected from a single bond, $CR_2$, O, NR or C(=O) or, for n=3, stands for N or, for n>2, is selected from an aromatic or heteroaromatic ring system having 5 to 24 aromatic ring atoms, which is optionally substituted by one or more radicals R.

9. The compound according to claim 1, characterised in that at least one radical R is selected from the group consisting of an aromatic or heteroaromatic ring system having 5 to 24 aromatic ring atoms, which is optionally substituted by one or more radicals R$^1$, and/or in that at least one radical R is selected from —C(=O)Ar$^1$ or —P(=O)(Ar$^1$)$_2$ and/or in that at least one radical R is selected from triaryl- or heteroarylamine derivatives and/or at least one substituent R stands for —N(Ar$^1$)$_2$.

10. The compound according to claim 1, characterised in that at least one group R is selected from the group consisting of benzene, biphenyl, terphenyl, quaterphenyl, fluorene, spirobifluorene, naphthalene, pyrrole, furan, thiophene, indole, benzofuran, benzothiophene, carbazole, dibenzothiophene, dibenzofuran, 1,3,5-triazine, pyridine, pyrimidine, pyrazine, pyridazine, indenocarbazole, bridged carbazole, indolocarbazole, anthracene, phenanthrene, pyrene, triphenylene, benzanthracene, quinoline, isoquinoline, phenanthridine, phenanthroline, azacarbazole, imidazole, pyrazole, thiazole, oxazole, oxadiazole, triazole, benzimidazole and combinations of two, three or four of these groups, where the groups are each optionally substituted by one or more radicals R$^1$.

11. A formulation comprising at least one compound according to claim 1 and at least one further compound.

12. The formulation according to claim 11, wherein the at least one further compound is an organic solvent.

13. A method comprising incorporating the compound according to claim 1 in an electronic device.

14. An electronic device comprising at least one compound according to claim 1.

15. The electronic device according to claim 14, wherein the electronic device is an organic electroluminescent device, characterised in that the at least one compound is employed as matrix material for a fluorescent or phosphorescent emitter and/or in a hole-blocking layer and/or in an electron-transport layer.

16. The electronic device according to claim 14, wherein the electronic device is selected from the group consisting of organic electroluminescent devices, organic integrated circuits, organic field effect transistors, organic thin film transistors, organic light-emitting transistors, organic solar cells, organic dye sensitised solar cells, organic optical detectors, organic photo receptors, organic field-quench devices, light-emitting electrochemical cells, organic laser diodes and organic plasmon emitting devices.

* * * * *